US007635741B2

(12) United States Patent
Niu et al.

(10) Patent No.: US 7,635,741 B2
(45) Date of Patent: Dec. 22, 2009

(54) MULTIFUNCTIONAL MONOMERS AND THEIR USE IN MAKING CROSS-LINKED POLYMERS AND POROUS FILMS

(75) Inventors: Q. Jason Niu, Midland, MI (US); Robert E. Hefner, Jr., Lake Jackson, TX (US); James P. Godschalx, Midland, MI (US); James T. Pechacek, Indianapolis, IN (US); Kim E. Arndt, Carmel, IN (US)

(73) Assignee: Dow Global Technologies Inc.

( * ) Notice: Subject to any disclaimer, the term of this patent is extended or adjusted under 35 U.S.C. 154(b) by 1132 days.

(21) Appl. No.: 10/365,938

(22) Filed: Feb. 12, 2003

(65) Prior Publication Data

US 2004/0053033 A1     Mar. 18, 2004

(51) Int. Cl.
C08F 32/08 (2006.01)
C08F 36/00 (2006.01)
C08F 2/16 (2006.01)
B05D 3/02 (2006.01)
B05D 5/00 (2006.01)
B05D 3/12 (2006.01)

(52) U.S. Cl. .................. 526/281; 526/283; 524/804; 427/226; 427/243; 427/241

(58) Field of Classification Search ................ 427/226, 427/243, 241; 526/281, 283; 524/804
See application file for complete search history.

(56) References Cited

U.S. PATENT DOCUMENTS

| | | | |
|---|---|---|---|
| 4,400,540 A | 8/1983 | Reinhardt et al. | 568/31 |
| 5,965,679 A | 10/1999 | Godschalx et al. | 526/281 |
| 6,093,636 A | 7/2000 | Carter et al. | 438/623 |
| 6,121,495 A | 9/2000 | Babb et al. | 568/17 |
| 6,156,812 A | 12/2000 | Lau et al. | 521/77 |
| 6,172,128 B1 | 1/2001 | Lau et al. | 521/77 |
| 6,313,185 B1 | 11/2001 | Lau et al. | 521/77 |
| 6,359,091 B1 * | 3/2002 | Godschalx et al. | 526/285 |
| 6,391,932 B1 | 5/2002 | Gore et al. | 521/61 |
| 2001/0040294 A1 | 11/2001 | Hawker et al. | 257/758 |
| 2003/0008989 A1 | 1/2003 | Gore et al. | 526/227 |

FOREIGN PATENT DOCUMENTS

| | | |
|---|---|---|
| DE | 40 35 300 A1 | 5/1992 |
| DE | 43 21 197 A1 | 1/1995 |
| JP | 2001-19724 | 1/2001 |
| JP | 2001-348422 | 12/2001 |
| WO | WO 98/11149 | 3/1998 |
| WO | WO 00/31183 | 6/2000 |
| WO | WO 01/38417 A1 | 5/2001 |

OTHER PUBLICATIONS

Kumar, et al., "Hybrid Polyimide-Pholyphenylenes by the Diels-Alder POlymerizatio Betwene Biscyclopentadienones and Ehtynyl- Temrinated Imides," *American Chemical Society Symposium Series*, vol. 614, Chapter 34, pp. 518-526.

Baker et al., "Hexaarylbenzene Units as Cross-Linking Sites for Polyguinolines," *Macromolecules*, vol. 12, No. 3, pp. 369-373 (1979).

Braham et al., "Polyphenylenes via Bis(2-pyrones) and Diethynylbenzenes. The Effect of m- and p-Phenylene Units in the Chain," *Macromolecules*, vol. 11, No. 2, pp. 343-346 (1978).

Charlier et al., "High temperature polymer nanofoams based on amorphous, high $T_g$ polyimides," *Polymer*, vol. 36, No. 5, pp. 987-1002 (1995).

Feldman et al., "Synthesis of a Chiral Binaphthyldisulfide: A Potentially Useful Reagent for Catalytic Asymmetric Synthesis," *Tetrahedron Letters*, vol. 33, No. 47, pp. 7101-7102 (1992).

Hedrick et al., "Polyimide Nanofoams from Aliphatic Polyester-Based Copolymers," *Chem. Mater.*, vol. 10, pp. 39-49(1998).

Hedrick et al., "High temperature polymer foams," *Polymer*, vol. 34, No. 22, pp. 4717-4726 (1993).

Kalantar et al., "Nanoscale Polymerized Hydrocarbon Particles and Methods of Making and Using Such Particles," U.S. Appl. No. 10/077,642, filed Feb. 15, 2002.

Keshtov et al., "A new method of preparing poly(phenylene ethynylenes)," *Vysokomol. Soedin., Ser. A Ser. B*, vol. 43, No. 6, pp. 957-962(2001)—Abstract Only.

Kumar et al., "Diets-Alder Polymerization between Bis(cyclopentadienones and Acetylenes. A versatile Route to New Highly Aromatic Polymers," *Macromolecules*, vol. 28, pp. 124-130 (1995).

Liu et al., "5-(Trimethylstannyl)-2-*H*-pyran-2-one and 3-(Trimethylstannyl)-2-*H*pyran-2-one: New 2-*H*-Pyran-2-one Synthons," *J. Org. Chem.*, vol. 61, pp. 6693-6699 (1996).

McDonald et al., "Diels-Alder Reactivity of Oxygenated Dienes and Furans. Synthesis of Oxygenated Biphenyls," *J. Chem. Soc. Perkin Trans.*, vol. 1, pp. 1893-1900(1979).

Ogliaruso et al., "Bistetracyclones and Bishexaphenylbenzenes," *J. Org. Chem.*, vol. 30, pp. 3354-3360(1965).

Ogliaruso et al., "'Bistetracyclones' and 'Bishexaphenylbenzenes,'" vol. 28, pp. 2725-2728(1963).

Rusanov et al., "New synthetic approach to the preparation of polyphenyleneethynylenes and polyheteroaryleneethynylenes," *High Perform. Polym.*, vol. 13, pp. S153-S168 (2001).

(Continued)

*Primary Examiner*—William K Cheung

(57) ABSTRACT

This invention is a monomer comprising at least two dienophile groups and at least two ring structures which ring structures are characterized by the presence of two conjugated carbon-to-carbon double bonds and the presence of a leaving group L, wherein L is characterized that when the ring structure reacts with a dienophile in the presence of heat or other energy sources, L is removed to form an aromatic ring structure. This invention is also curable oligomers and polymers and highly cross-linked polymers made with such monomers. Moreover, this invention is a method of making porous films by combining such monomers or their oligomers with a porogen, curing the polymer and removing the porogen.

10 Claims, No Drawings

OTHER PUBLICATIONS

Rusanov et al., "Phenylated polyphenylenes based on 4,4'-diethynylbenzophenone," *Vysokomol. Soedin., Ser. A Ser. B*, vol. 42, No. 11, pp. 1931-1935 (2000)—Abstract Only.

Rusanov et al., "New phenylated: fluoro-containing poly(phenylenes)," *Vysokomol. Soedin, Ser. A Ser. B*, vol. 43, No. 4, pp. 581-587 (2001)—Abstract Only.

Rusanov et al., "Phenylated polyphenylenes containing hexafluoroisopropylidene groups," *Polym. Prepr.*, vol. 39, No. 2, pp. 794-795 (1998)—Abstract Only.

Rusanov et al., "Acetylene-containing phenytated polyphenylenes," *Vysokomol. Soedin., Ser. A. Ser. B*, vol. 42, No. 3, pp. 399-403 (2000)—Abstract Only.

Rusanov et al., "Poly(arylene oxides) based on new types of activated difluoroaromatic compounds," *Vysokomol. Soedin., Ser. A Ser. B*, vol. 41, No. 1, pp. 27-54(1999)—Abstract Only.

Schilling et al., "Diels-Alder Polymerization. VI. Phenylated Polyphenylenes from Bis-2-pyrones and *p*-Diethynylbenezene," *Macromolecules*, vol. 2, No. 1, pp. 85-88 (1969).

So et al., "Method of Making Nanoporous Film," U.S. Appl. No. 10/077,646, filed Feb. 15, 2002.

Tong et al., "The Albatrossenes: Large, Cleft-Containing, Polyphenyl Polycylic Aromatic Hydrocarbons," *J. Am. Chem. Soc.*, vol. 119, pp. 7291-7302(1997).

Turchi et al.,"Reactions of 4,5-Dicyanopyridazine with Alkynes and Enamines: a New Straightforward Complementary Route to 4-Mono- and 4,5-Disubstituted Phthalonitriles," *Tetrahedron*, vol. 64, pp. 1809-1816(1998).

VanKerckhoven et al., "Poly(*p*-phenylene). The Reaction of 5,5'-*p*-Phenylenebis-2-pyrone with *p*-Diethynyibenzene," *Macromolecules*, vol. 5, No. 5, pp. 541-546(1972).

Wiesler et al., "Divergent Synthesis of Polyphenylene Dendrimers: The Role of Core and Branching Reagents upon Size and Shape," *Macromolecules*, vol. 34, pp. 187-199(2001).

Xu et al., "Preparation of PMDA/ODA Polyimide Foams Using Polystyrene Nanospheres as Templates," *Polymer Materials: Science & Engineering*, vol. 85, pp. 502-503 (2001).

\* cited by examiner

MULTIFUNCTIONAL MONOMERS AND THEIR USE IN MAKING CROSS-LINKED POLYMERS AND POROUS FILMS

This invention was made with United States Government support under Cooperative Agreement No. 70NANB8H4013 awarded by NIST. The United States Government has certain rights in the invention.

FIELD OF THE INVENTION

This invention relates to monomers having at least two different reactive functional groups and to aromatic polymers made from these monomers. More particularly, these polymers are useful as dielectric materials in making microelectronic devices.

BACKGROUND OF THE INVENTION

Crosslinked or crosslinkable polyarylenes that are stable at high temperatures and have good electrical insulative properties have been taught for use in the manufacture of microelectronic devices. U.S. Pat. No. 5,965,679 (Godschalx et al.) taught the manufacture of such materials by reacting polyfunctional compounds having two or more cyclopentadienone groups with polyfunctional compounds having two or more aromatic acetylene groups, at least some of the polyfunctional compounds having three or more reactive groups. These materials are useful as interlayer dielectrics in manufacture of integrated circuits and as dielectrics in manufacture of other microelectronic devices. Godschalx et al. also taught monomers which contained one cyclopentadienone group together with two aromatic acetylene groups and polymers made from such monomers. Typically, these materials are spin coated onto a substrate followed by a hotplate baking step and a subsequent curing at about 400° C. in an oven to complete the cure.

In WO 01/38417, it was taught that it may be desirable to adjust the modulus of polymers as taught in Godschalx et al., by adjusting the ratio of the reactants in Godschalx or by adding other reactive species to the monomers or to the partially polymerized product of Godschalx.

U.S. Pat. No. 6,172,128 teaches aromatic polymers containing cyclopentadienone groups that may react with aromatic polymers containing phenylacetylene groups to provide branched or cross-linked polymers. U.S. Pat. No. 6,156,812 shows polymers which contain both cyclopentadienone groups and phenyl acetylene groups in the backbone of the polymer.

SUMMARY OF THE INVENTION

The present inventors have discovered a new class of monomers and polymers made from the monomers which possess some or all of the following remarkable benefits. These monomers generally display rapid but easily controlled reactivity enabling a partial polymerization or oligomerization, followed by subsequent processing and ultimately cure or cross-linking of the composition. When these monomers polymerize, there is generally a rapid increase in modulus up to a plateau value indicating that the polymer can reach the gel point and/or the vitrification point fairly rapidly. These monomers polymerize to provide aromatic polymers that have high crosslink density. These polymers display excellent thermal stability at high temperatures. Beneficially, these materials can be cured past their gel point at temperatures in the range of about 200-300° C. Thus, less rigorous heating steps and/or shorter times are required before one is able to solvent coat additional layers over the film. In addition, since the systems do not require use of comonomers, manufacture of the curable oligomers or polymers is simplified by reducing the risk of incorrect addition or improper ratio of reactants. Finally, for several of the preferred embodiments, the partially polymerized species have sufficient solubility to enable use of a single solvent system thereby again simplifying manufacturing processes and potentially avoiding coating problems which may occur when using mixed solvent systems.

Thus, according to a first embodiment this invention is a monomer comprising at least two dienophile groups and at least two ring structures which ring structures are characterized by the presence of two conjugated carbon-to-carbon double bonds and the presence of a leaving group L, wherein L is characterized that when the ring structure reacts with a dienophile in the presence of heat or other energy sources, L is removed to form an aromatic ring structure.

According to a second embodiment, this invention is a branched, curable oligomer or polymer made from such monomers. Also this invention is a branched curable oligomer or polymer comprising the reactive functional groups as pendant groups, terminal groups and as groups within the backbone of the oligomer or polymer.

According to a third embodiment this invention is a highly crosslinked polymer made from such monomers or made by curing the curable oligomers or polymers.

According to a fourth embodiment, this invention is a composition comprising the branched, curable oligomer of the second embodiment and a porogen. As used herein, porogens are components which may be removed from the gelled polymer or, more preferably, the vitrified (i.e. fully cured or cross-linked) polymer by solvents or, more preferably, by thermal decomposition resulting in the formation of porosity. Other embodiments are the method of using this composition to form a porous film and the article made by such a method.

According to a fifth embodiment, the invention is a method of forming a film comprising a highly cross-linked aromatic polymer which method comprises providing the above monomer, partially polymerizing the monomer to form a curable oligomer or polymer containing dienophile groups and the ring structures as pendant groups, terminal groups and as groups within the backbone of the oligomer or polymer; coating a composition comprising the oligomer or curable polymer onto a substrate and curing to form a cross-linked aromatic polymer.

According to a sixth embodiment, this invention is an article made by the above method.

DETAILED DESCRIPTION OF THE INVENTION

The Monomers and their Syntheses

The monomers of the present invention preferably comprise from two to four, more preferably two or three, and most preferably two of the ring structures having two conjugated carbon to carbon double bonds and have the leaving group, L. Examples of suitable ring structures include cyclopentadienones, pyrones, furans, thiophenes, and pyridazines. The monomers of the present invention preferably comprise two, three, four, five, six, seven eight, nine or ten, of the dienophile groups. Examples of suitable dienophile groups are acetylene groups, preferably phenyl acetylene groups, nitrile groups, and the like.

Preferably, the ring structure is a five-membered ring where L is —O—, —S—, —(CO)—, or —(SO$_2$)—, or a six membered ring where L is —N=N—, or —O(CO)—.

Optionally, two of the carbon atoms of the ring structure and their substituent groups taken together may form an aromatic ring—i.e. the 5 or 6 membered ring structures may be fused to an aromatic ring. Most preferably, L is —(CO)— such that the ring is a cyclopentadienone group.

The monomers preferably have two or three of the ring structures. Preferred monomers that have two ring structures may be conveniently represented by the formula Z-X-Z wherein Z is selected from

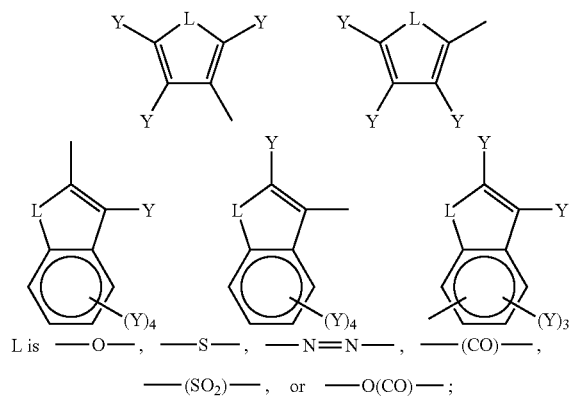

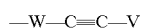
L is —O—, —S—, —N=N—, —(CO)—,

—(SO$_2$)—, or —O(CO)—;

Y is independently in each occurrence hydrogen, an unsubstituted or inertly substituted aromatic group, an unsubstituted or inertly substituted alkyl group or

—W—C≡C—V

X is an unsubstituted or inertly substituted aromatic group or is

—W—C≡C—W— and

W is an unsubstituted or inertly substituted aromatic group, and V is hydrogen, an unsubstituted or inertly substituted aromatic group, or an unsubstituted or inertly substituted alkyl group;

provided that at least two of the X and Y groups comprise an acetylene group.

By inertly-substituted as used herein, applicants mean a substituent group which does not interfere with the polymerization reaction of the monomer.

Preferred monomers that have three ring structures may be represented by the formula Z-X-Z'-X-Z, wherein Z' is selected from

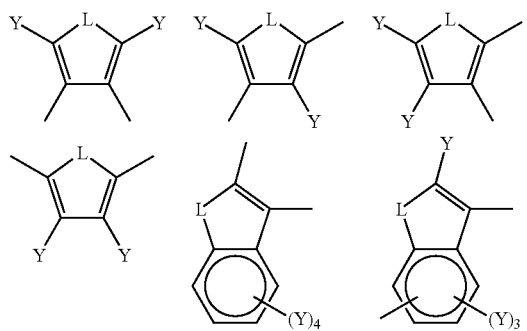

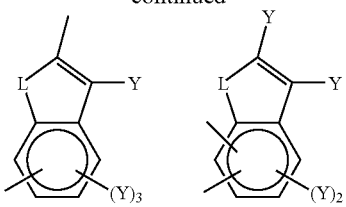

and L, Y, Z, and X are as defined above.

One class of preferred monomers are of the Formula I:

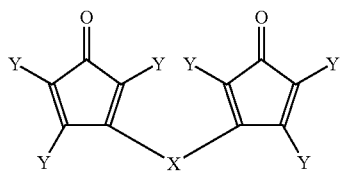

wherein X and Y are as defined above. Preferably, two, four or six of the Y groups comprise acetylene groups.

Non-limiting examples of divalent unsubstituted or inertly-substituted aromatic moieties include:

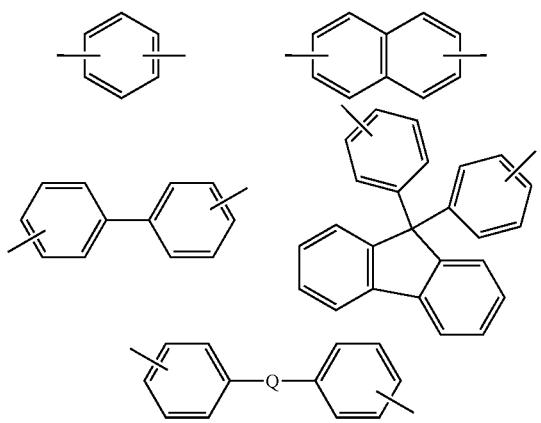

wherein Q can be —O—, —S—, alkylene, —CF$_2$—, —CH$_2$—, and the following inert groups,

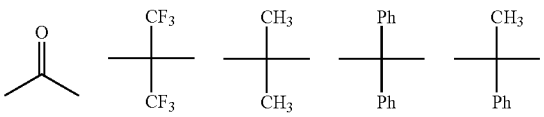

and Ph is a phenyl group. Similarly, monovalent unsubstituted or inertly-substituted aromatic moieties would include the above species where one of the bonds shown connects to hydrogen, an alkyl group of one to ten carbon atoms, or the like. Unsubstituted or inertly-substituted alkyl moieties may include but are not limited to alkyls having one to twenty, preferably one to ten, carbon atoms.

Specific preferred monomers include Formula II:
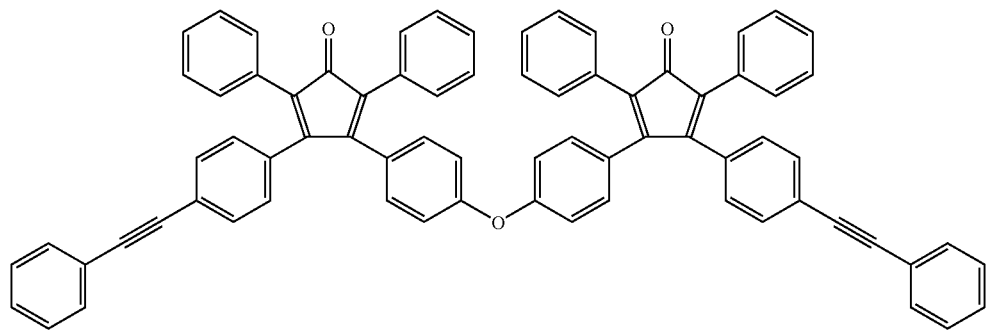
Formula III (a mixture of):
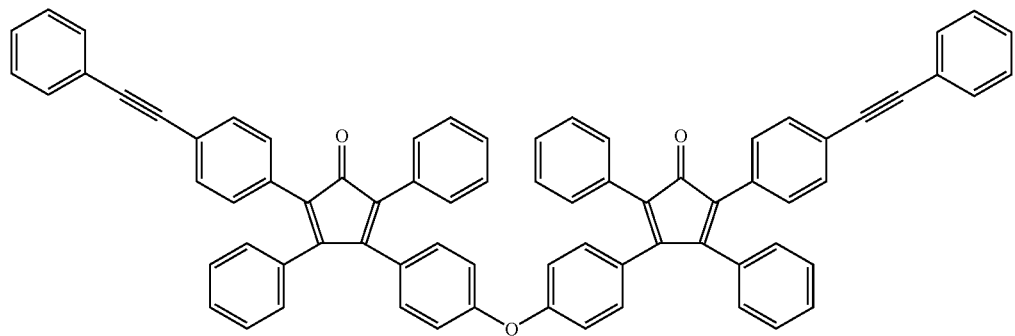
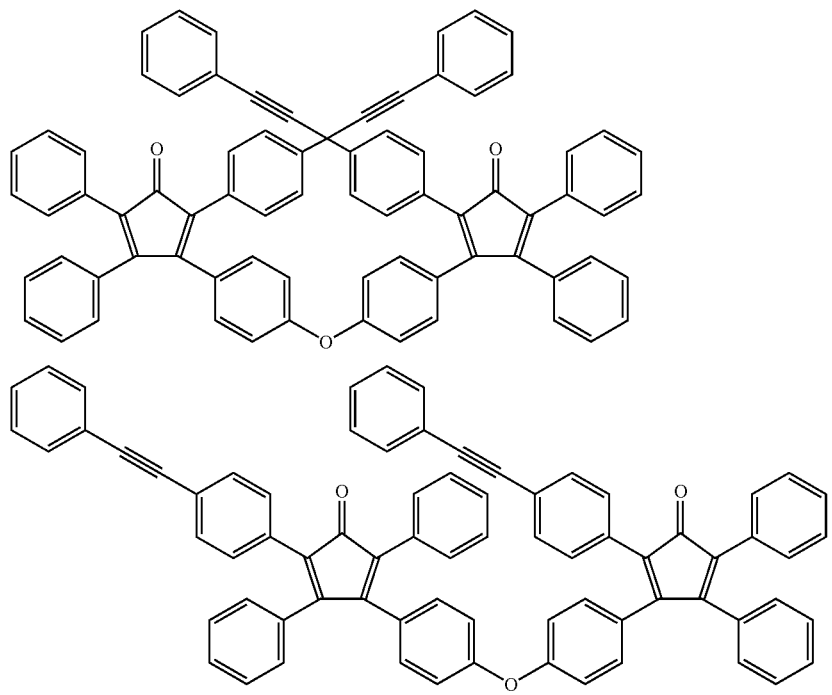

-continued
Formula IV:
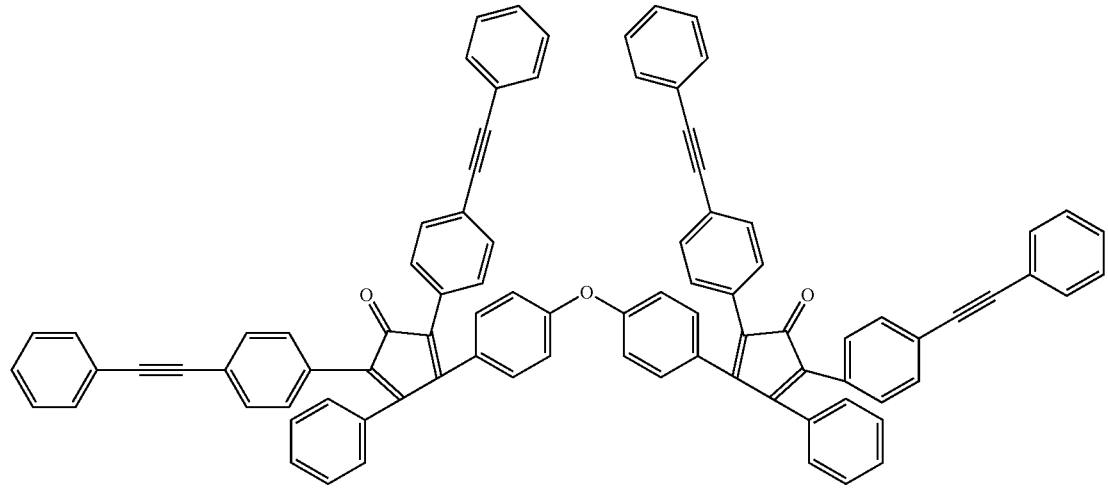
Formula V:
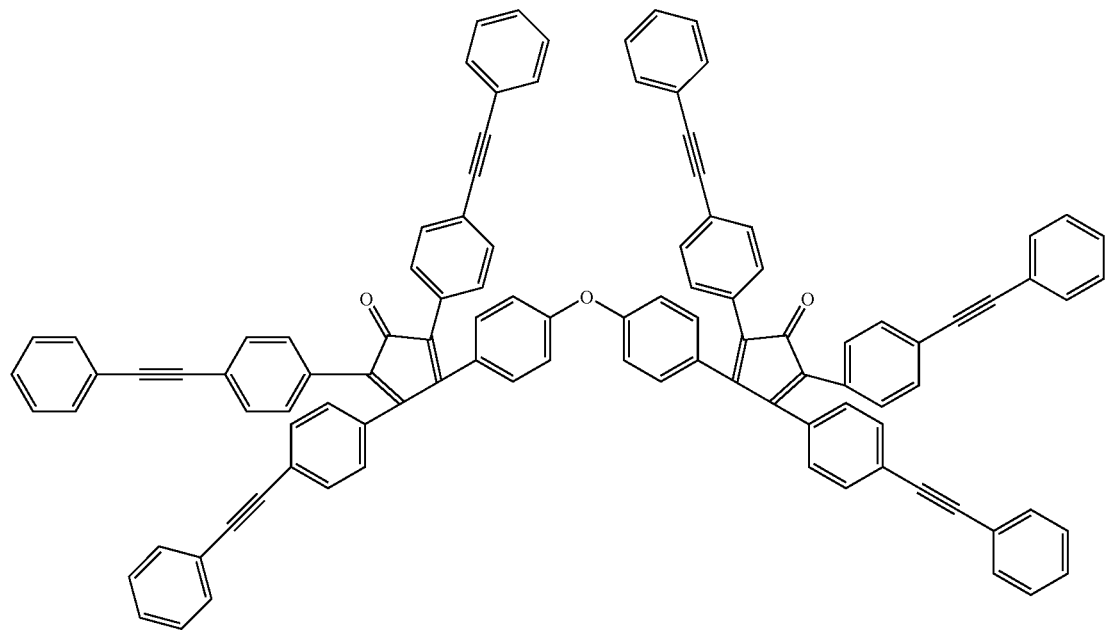
Formula VI:
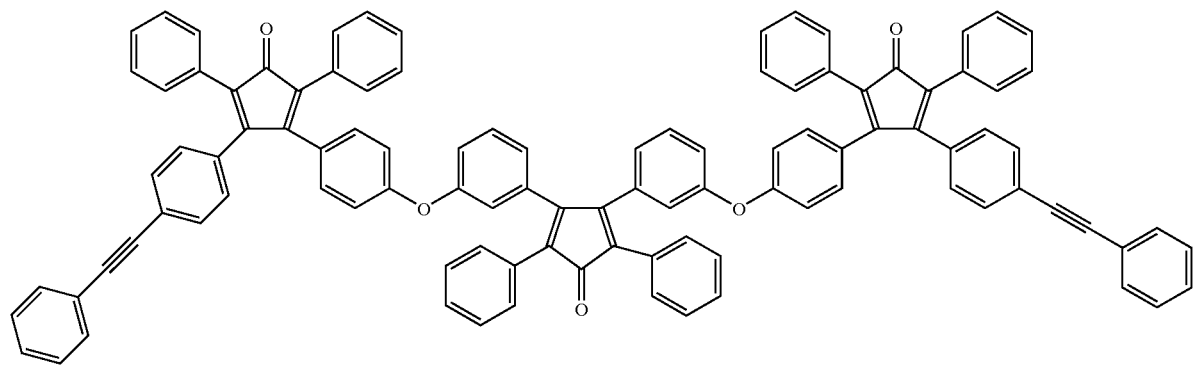

-continued
Formula VII:
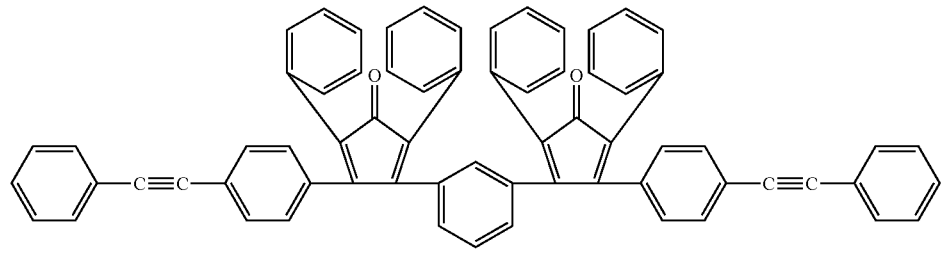
Formula VIII:
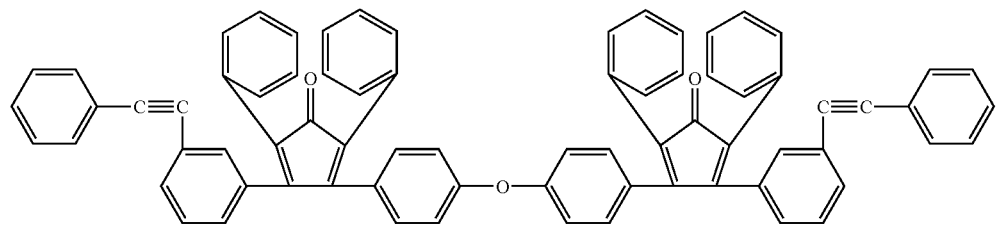
Formula IX:
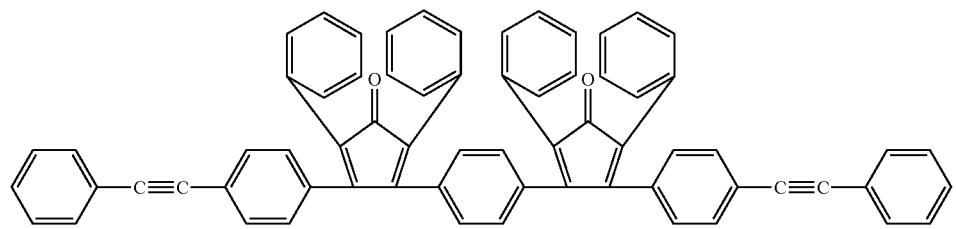
Formula X:
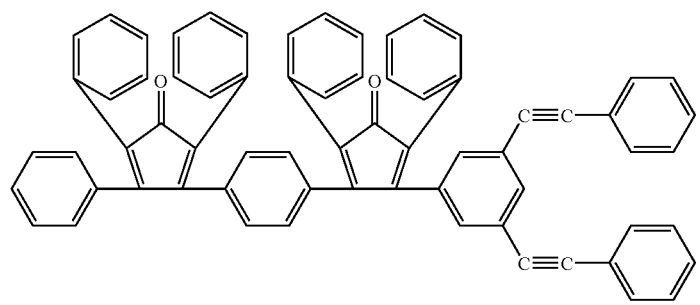
Formula XI:
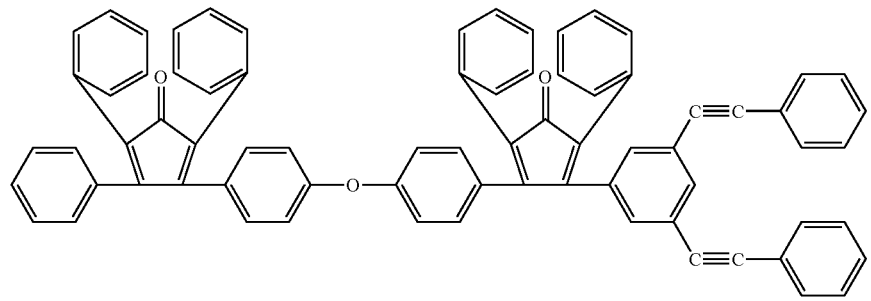

-continued
Formula XII:
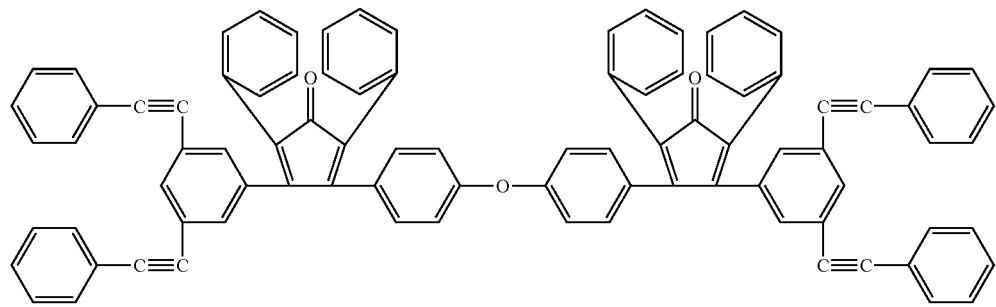
Formula XIII:
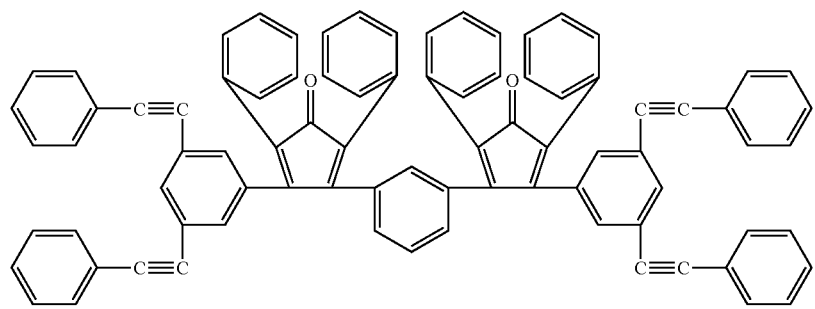
Formula XIV:
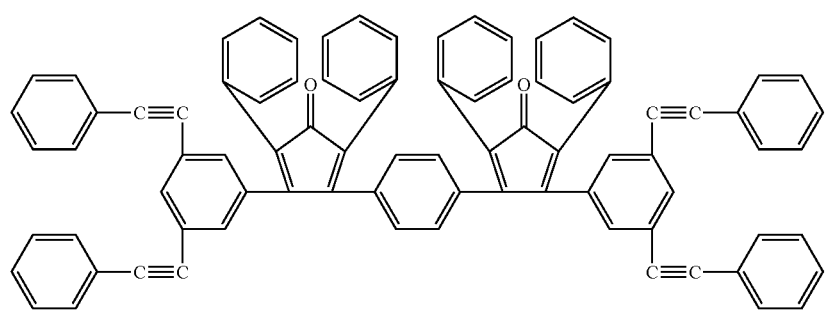
Formula XV:
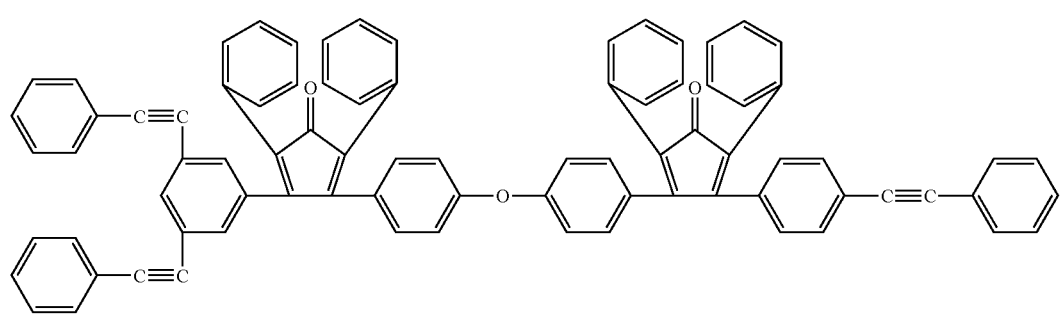
Formula XVI:
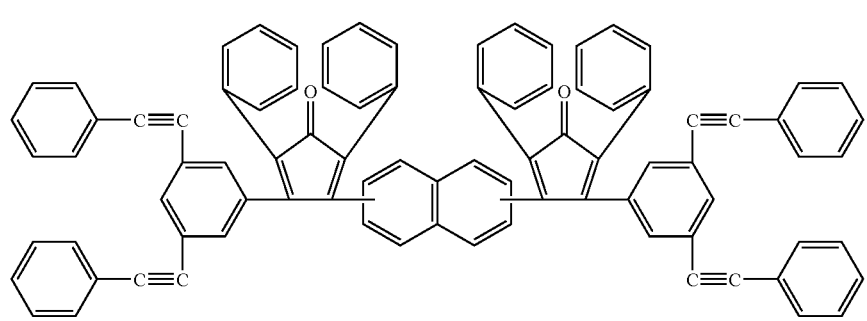

Formula XVII:
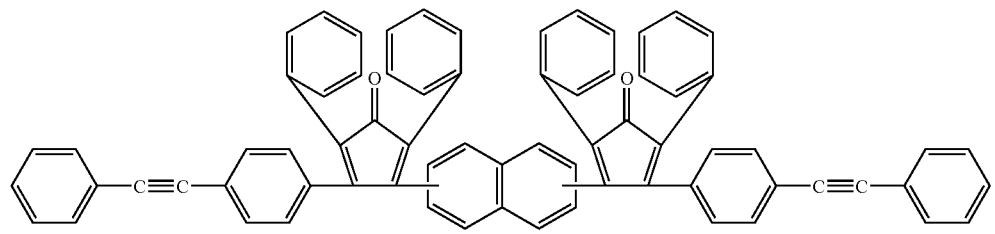
Formula XVIII:
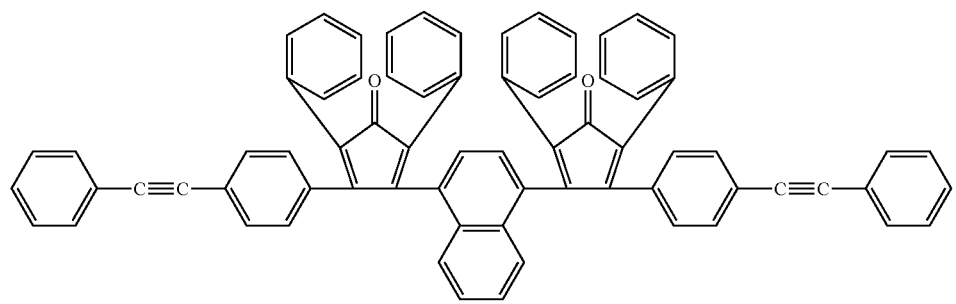
Formula XIX:
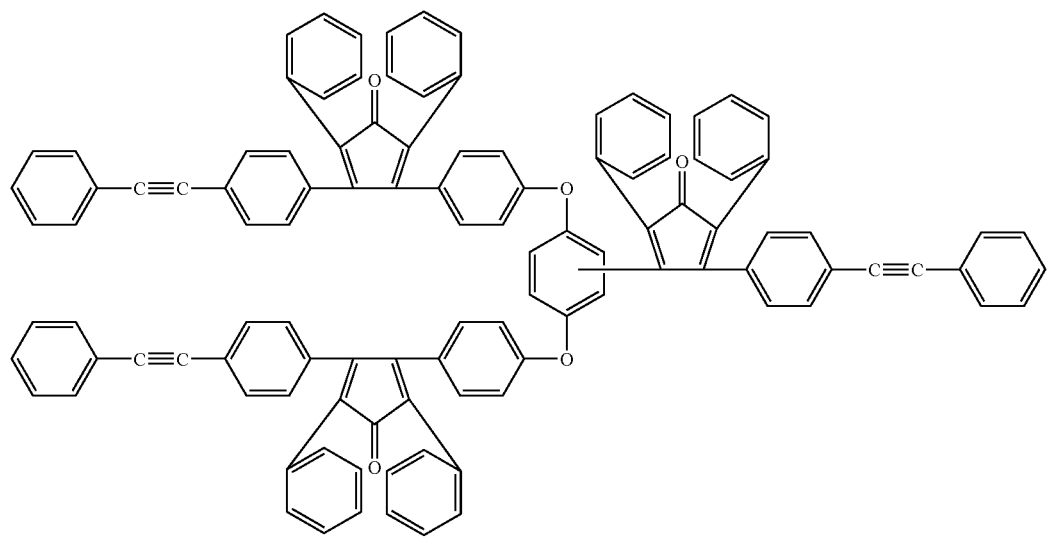
Formula XX (a mixture of):
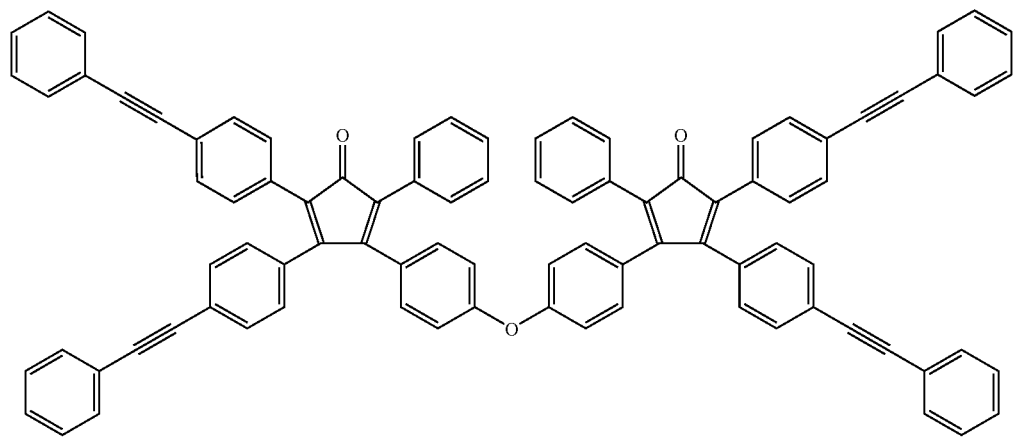

-continued
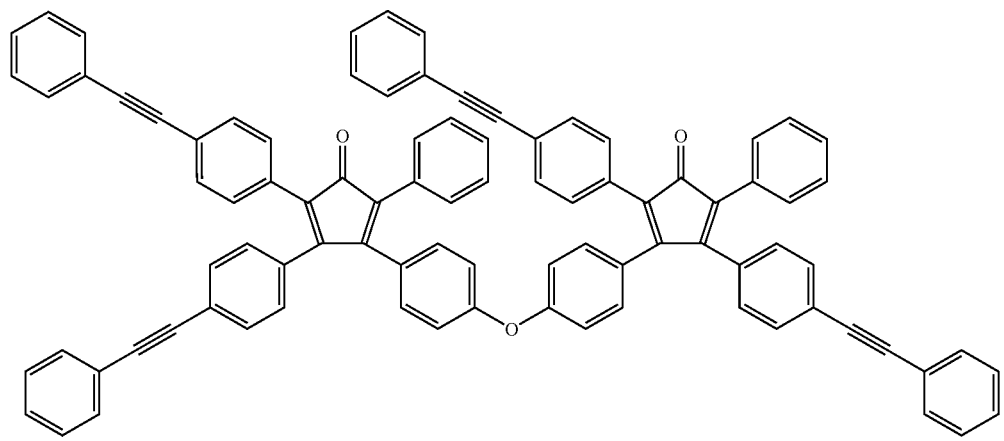
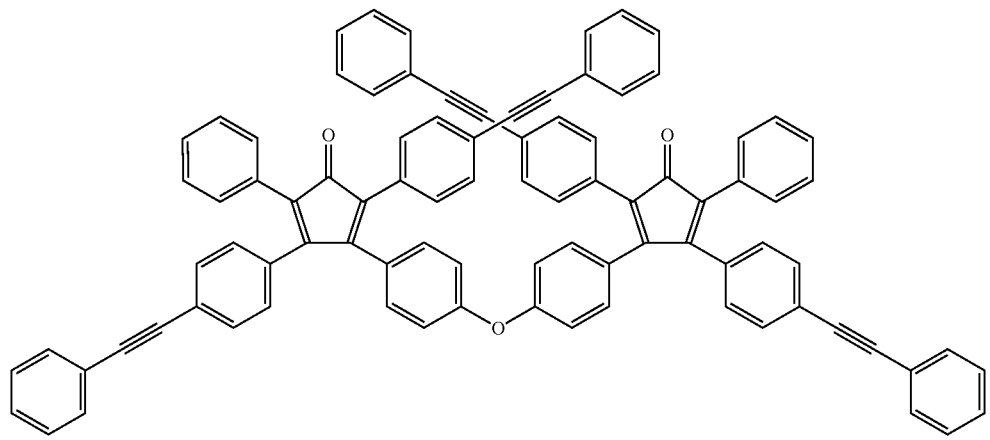
Formula XXI (a mixture of):
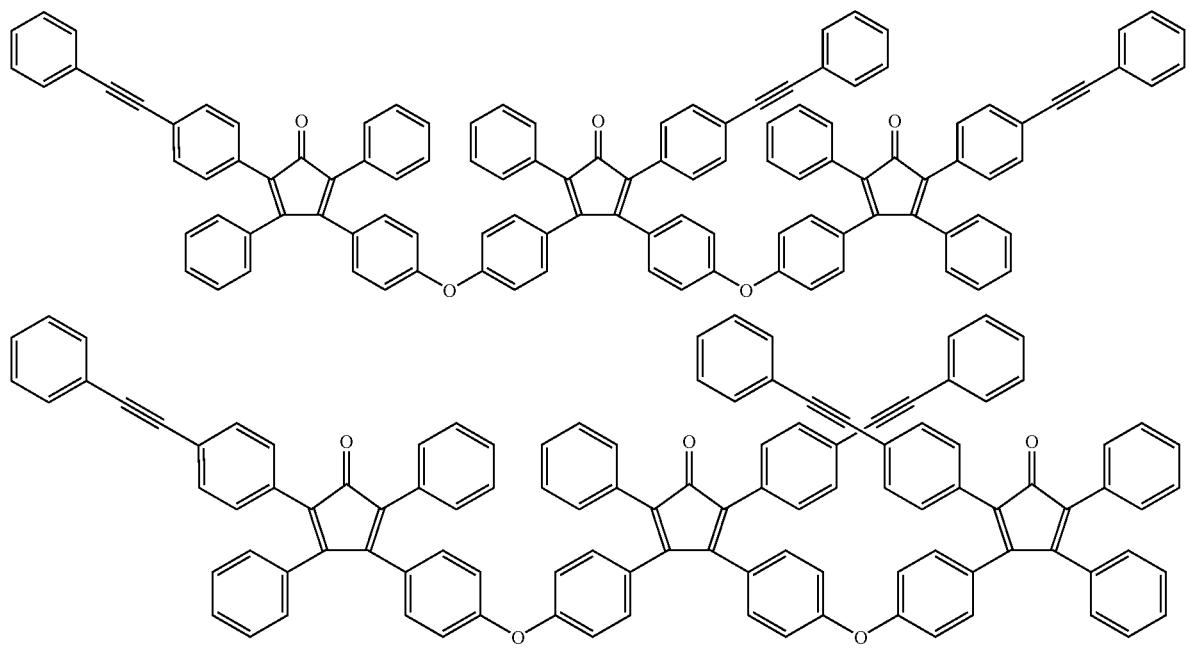

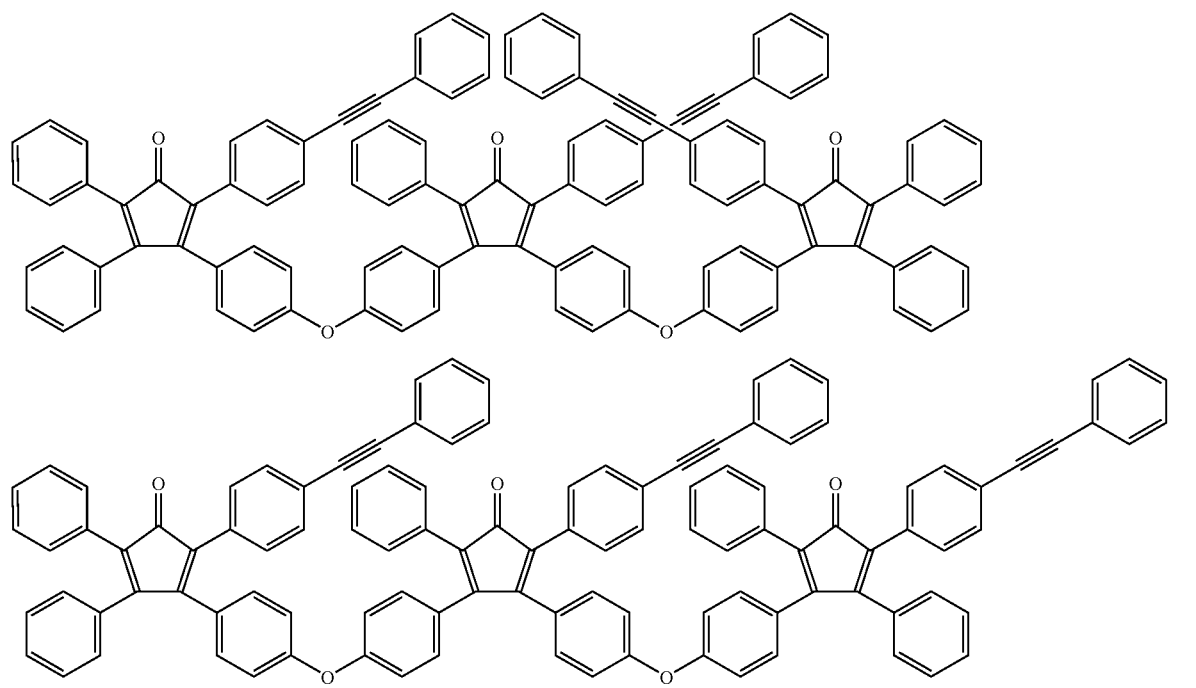
Formula XXII (a mixture of):
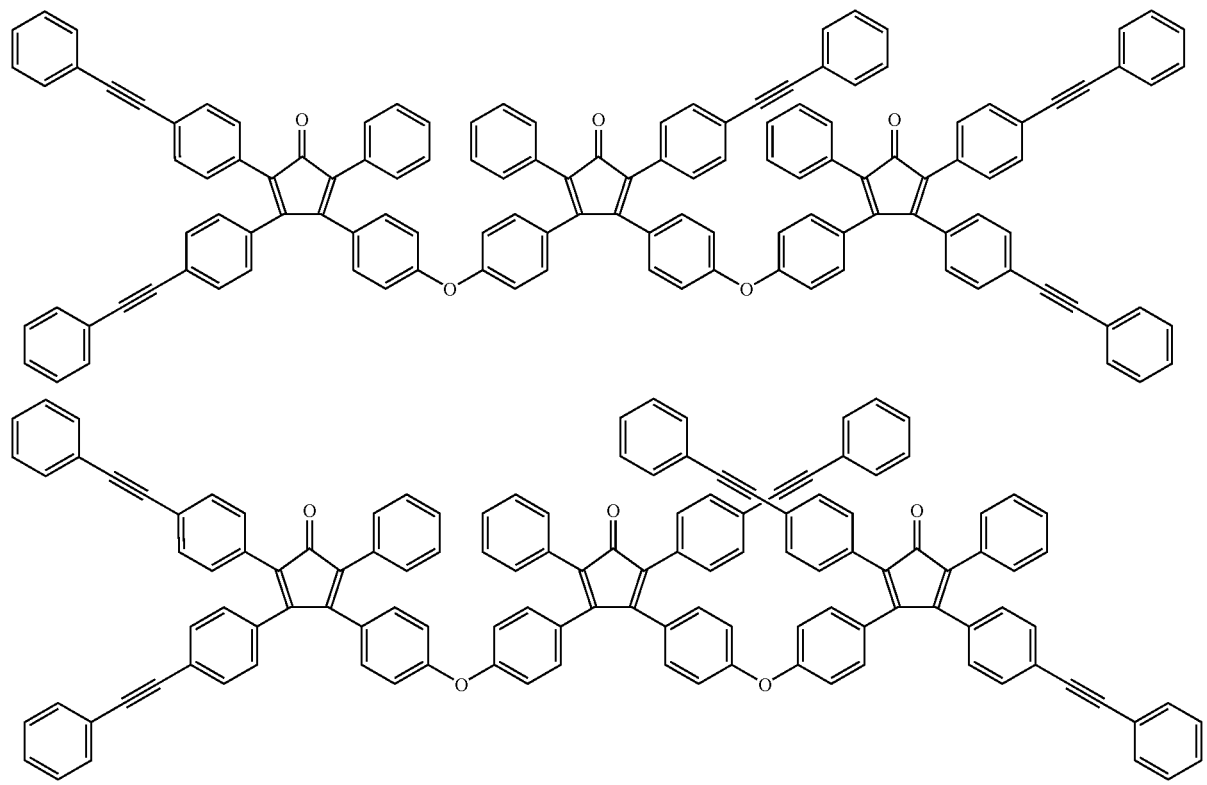

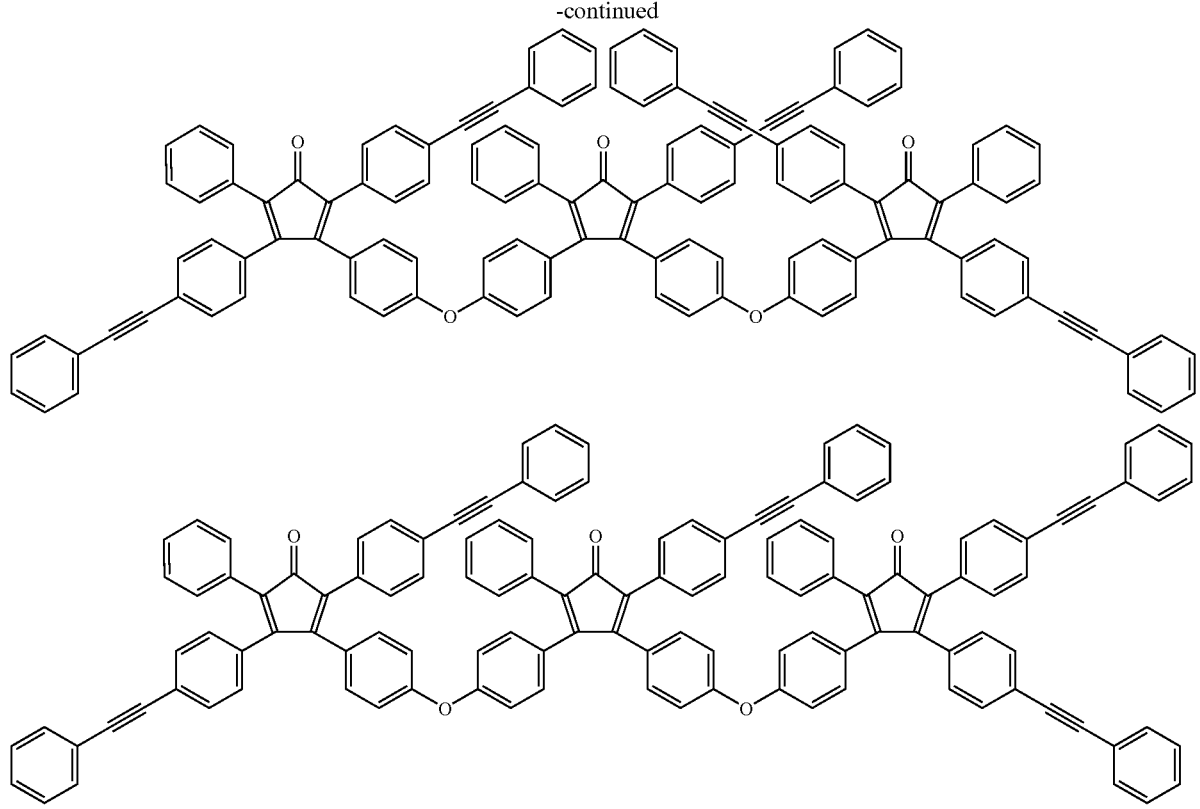
Formula XXIII:
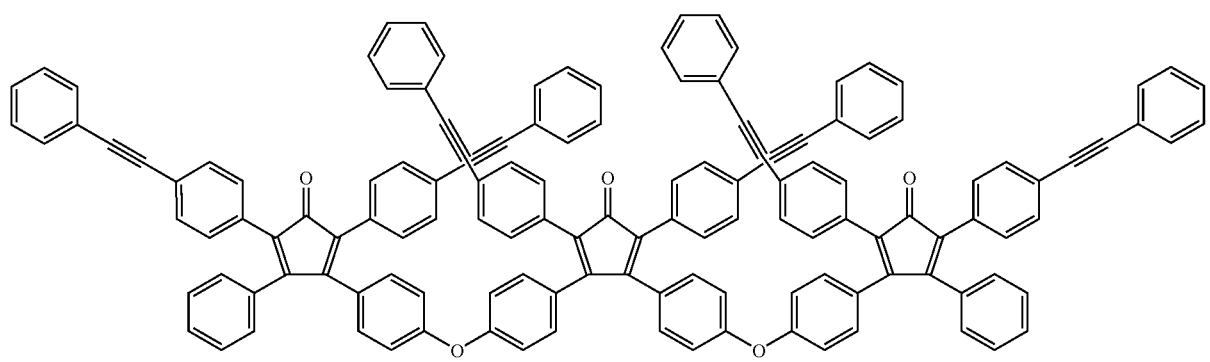
Formula XXIV:
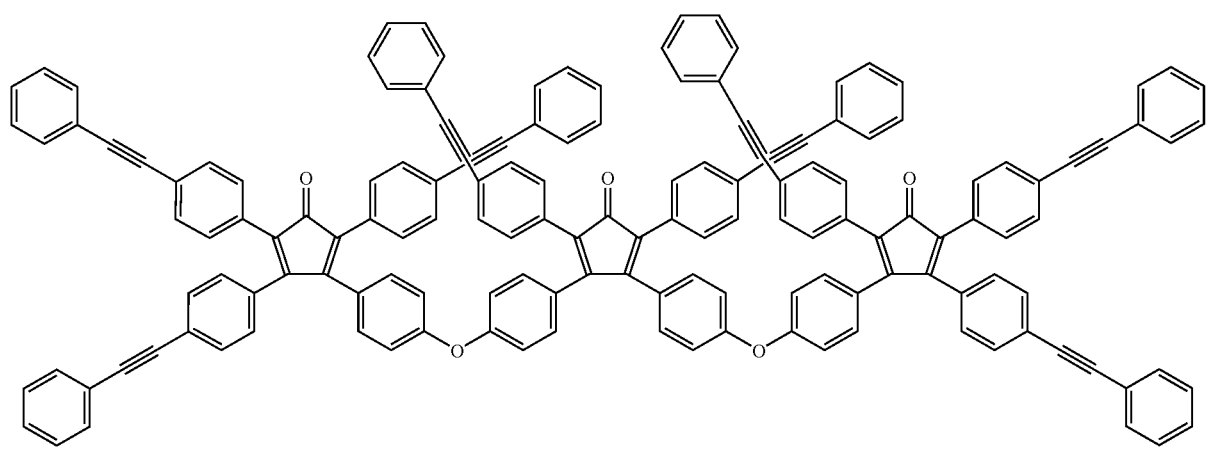

Formula XXV:

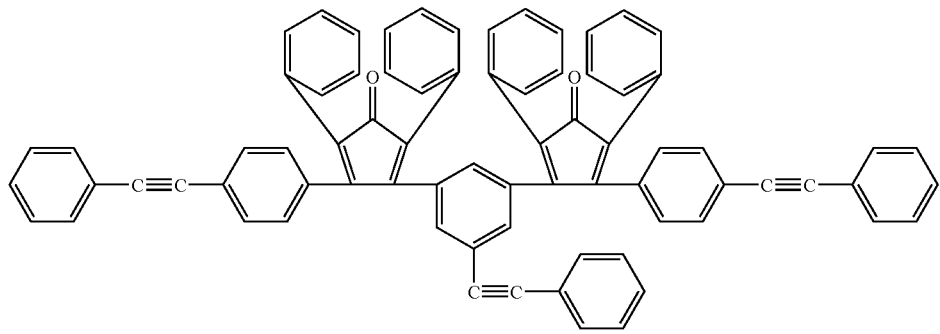

Formula XXVI:

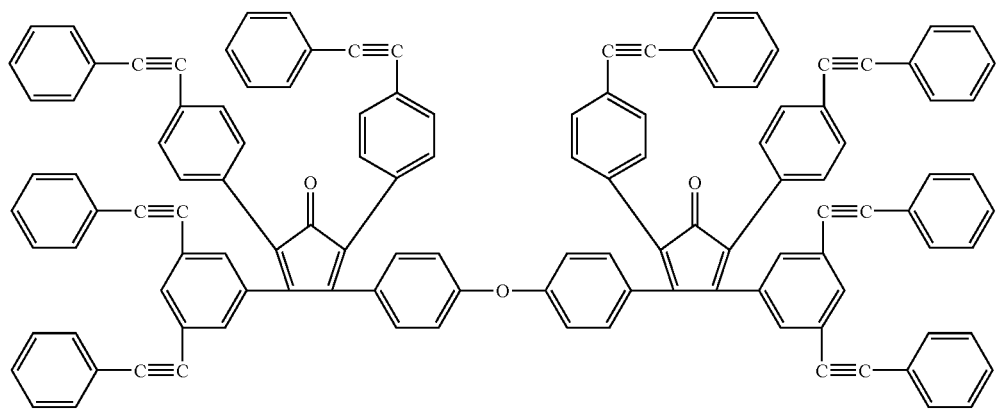

Formula XXVII

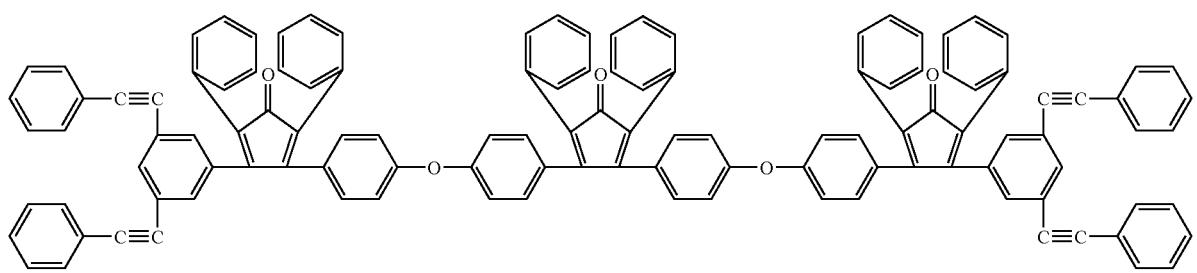

Formula XXVIII

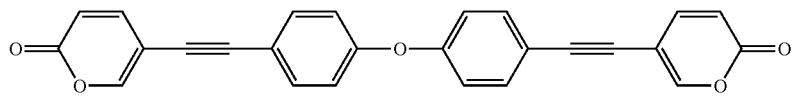

Monomers of this invention where the ring structure is a cyclopentadienone may be made, for example, by condensation of substituted or unsubstituted benzils with substituted or unsubstituted benzyl ketones (or analogous reactions) using conventional methods. See e.g. Kumar, et al. Macromolecules, 1995, 28, 124-130. Ogliaruso et al, J. Org. Chem, 1965, 30, 3354: Ogliaruso, et al., J. Org. Chem., 1963, 28, 2725, Wiesler, et al, Macromolecules, 2001, 34, 187, Baker, et al, Macromolecules, 1979, 12, 369, Tong, et al, J. Am. Chem. Soc. 1997, 119, 7291, and U.S. Pat. No. 4,400,540, all of which are incorporated herein by reference. Monomers having the other structures may be prepared as follows: Pyrones can be prepared using conventional methods such as those shown in the following references and references cited therein: Braham et. al. Macromolecules 11, 343 (1978); Liu et. al. J. Org. Chem. 61, 6693-99 (1996); van Kerckhoven et. al. Macromolecules 5, 541 (1972); Schilling et. al. Macromolecules 2, 85 (1969); Puetter et. al. J. Prakt. Chem. 149, 183 (1951). Furans can be prepared using conventional methods such as those shown in the following references and references cited therein: Feldman et. al. Tetrahedron Lett. 47, 7101 (1992); McDonald et. al. J. Chem. Soc. Perkin Trans. 1 1893 (1979). Pyrazines can be prepared using conventional methods such as those shown in the following references and references cited therein: Turchi et. al. Tetrahedron 1809 (1998). All citations listed above are incorporated herein by reference.

For example, the following reaction is exemplary of the synthesis that may be used in making the preferred monomers of Formulas II-V:

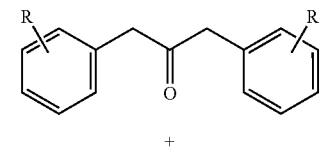

+

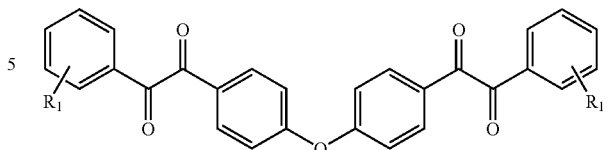

↓

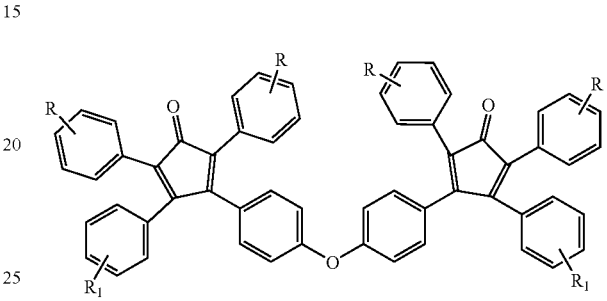

wherein R and $R_1$ are hydrogen or phenylethynyl groups. These synthons are

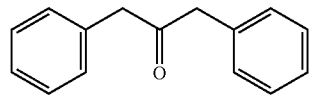

DPA-1

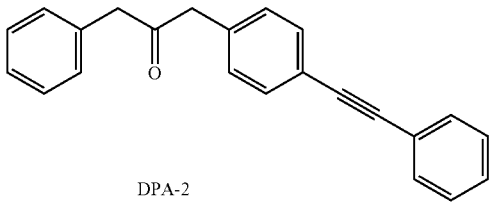

DPA-2

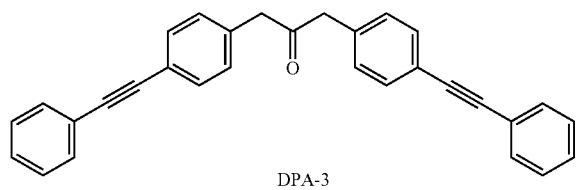

DPA-3 and

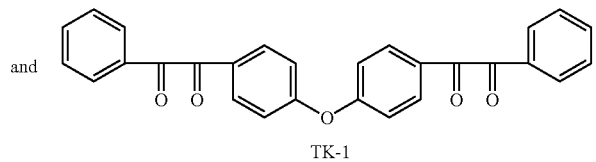

TK-1

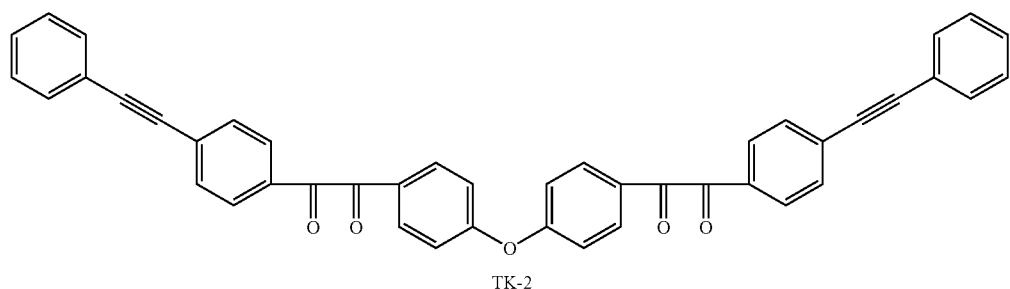

TK-2

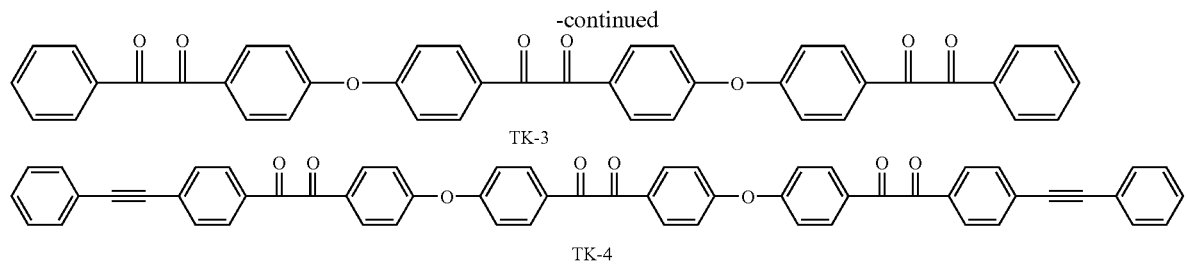

When DPA-1 is reacted with TK-2 the monomer of formula II is formed. When DPA-2 is reacted with TK-1 the monomers of formula III are formed. When DPA-3 is reacted with TK-1 monomer of formula IV is formed. When DPA-3 is reacted with TK-2, compound of formula V is formed. When DPA-1 is reacted with TK-4 monomer of formula VI is formed. When DPA-2 is reacted with TK-2, a mixture of three compounds is formed, they are regioisomers and all have 2 cyclopentadienone groups and 4 acetylene groups (formula XX). DPA-2 reacted with TK-3 yields a mixture of monomers having 3 cyclopentadienone groups and 3 acetylene groups (formula XXI). DPA-2 reacted with TK-4 yields a mixture of monomers having 3 cyclopentadienone groups and 5 acetylene groups (formula XXII). DPA-3 reacted with TK-3 yields a monomer having 3 cyclopentadienone groups and 6 acetylene groups (formula XXIII). DPA-3 reacted with TK-4 yields a monomer having 3 cyclopentadienone groups and 8 acetylene groups (formula XXIV).

As further example, DPA-1 and TK-1 are known compounds, DPA-2, DPA-3, and TK-2 can be synthesized by following the attached examples in this application. TK-3 may be synthesized as follows:

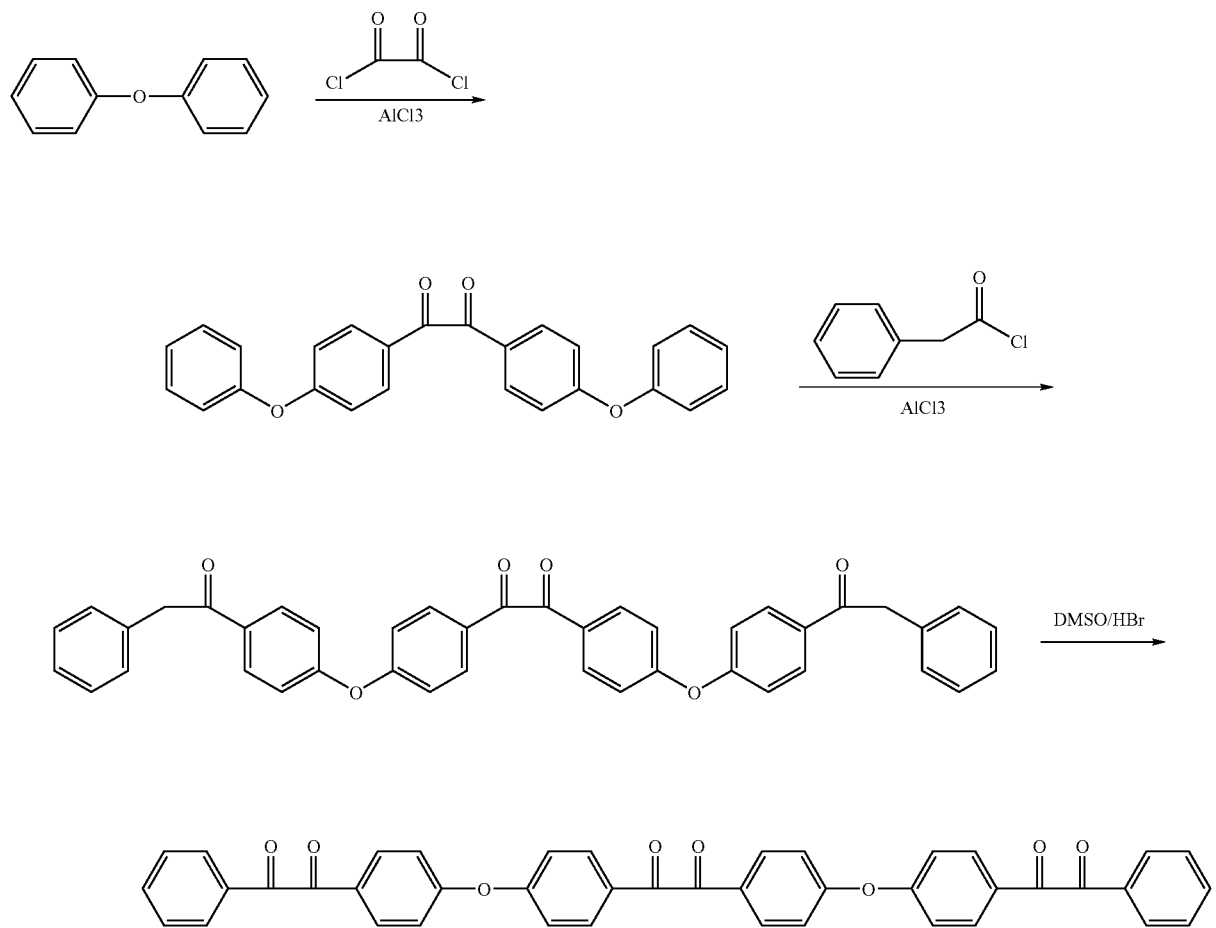

And TK-4 may be synthesized as follows:

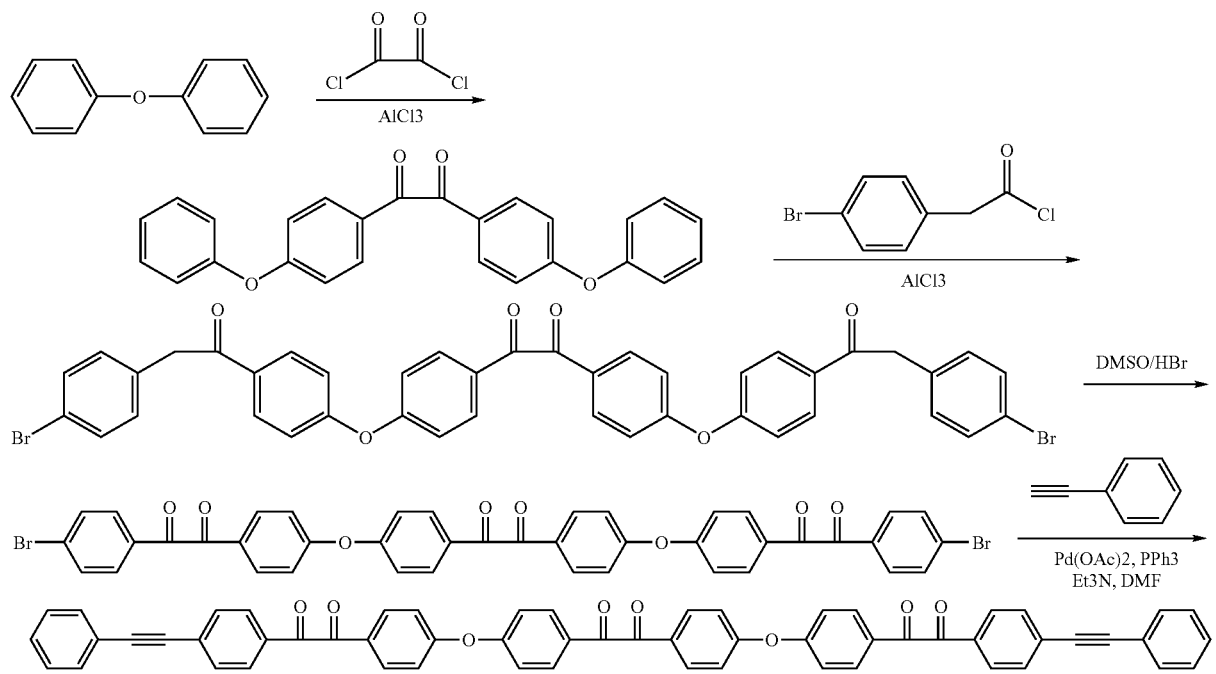

In more detail, the monomer of Formula II may be conveniently prepared using those methods delineated in Examples 1 or 13 herein. Briefly, said methods comprise: (a) chlorination of 4-bromophenylacetic acid with thionyl chloride to provide 4-bromophenylacetyl chloride, (b) Friedel-Crafts diacylation of phenyl ether with 4-bromophenylacetyl chloride using aluminum chloride and a solvent which is essentially inert to both reactants and product, (c) modified Kornblum oxidation of the diacylation product using dimethylsulfoxide and hydrobromic acid, (d) bis(phenylethynylation) of the bis(4-bromophenyl) tetraketone product with phenylacetylene using palladium catalysis, a tertiary amine, and a solvent which is essentially inert to both reactants and product (e) bis(cyclopentadienone) formation via double Aldol reaction of the bis(phenylethynyl) tetraketone with 1,3-diphenylacetone using a quaternary ammonium hydroxide catalyst and one or more solvents which are essentially inert to both reactants and product. The purity of the monomer may be widely varied depending on the reaction conditions utilized in the final synthetic step, (e) bis(cyclopentadienone) formation. Thus, in Example 1 E, the reactants and reaction conditions employed provide a product containing approximately 75 area % monomer II (by HPLC analysis). In Example 13 D, the reactants and reaction conditions are adjusted to provide high purity AABB monomer containing in excess of 98.5 area % monomer II (by HPLC analysis). Higher purity monomer II is generally most preferred for the applications taught by the present invention.

The monomer of Formula VIII may also be conveniently prepared using those methods given in Examples 1 or 13 herein. Said methods essentially comprise those methods used for the preparation of the monomer of Formula II, with the substitution of 3-bromophenylacetyl chloride for the 4-bromophenylacetyl chloride used therein. A specific synthesis of the monomer of Formula VIII is delineated in Example 18 of the present invention.

The monomer of Formula XII likewise may be conveniently prepared using those methods given in Examples 1 or 13 herein. Said methods essentially comprise those methods used for the preparation of the monomer of Formula II, with the substitution of 3,5-dibromophenylacetyl chloride for the 4-bromophenylacetyl chloride used therein. Additionally, it is understood that the (d) bis(phenylethynylation) now becomes a tetrakis(phenylethynylation) due to the stoichiometric presence of 2 additional aryl bromide groups in the tetraketone precursor.

The non-ether linked monomer of Formula VII may be conveniently prepared using those methods delineated in Example 5 herein. Briefly, said methods comprise: (a) chlorination of potassium 1,3-phenylenediacetate with thionyl chloride to provide 1,3-phenylenediacetyl chloride, (b) Friedel-Crafts acylation of bromobenzene with 1,3-phenylenediacetyl chloride using aluminum chloride and a solvent which is essentially inert to both reactants and product, (c) modified Kornblum oxidation of the acylation product using dimethylsulfoxide and hydrobromic acid, (d) bis(phenylethynylation) of the bis(4-bromophenyl) tetraketone product with phenylacetylene using palladium catalysis, a tertiary amine, and a solvent which is essentially inert to both reactants and product (e) bis(cyclopentadienone) formation via double Aldol reaction of the bis(phenylethynyl) tetraketone with 1,3-diphenylacetone using a quaternary ammonium hydroxide catalyst and one or more solvents which are essentially inert to both reactants and product.

The non-ether linked monomer of Formula IX may also be conveniently prepared using those methods given in Example 5 herein. Said methods essentially comprise those methods used for the preparation of the monomer of Formula VII, with the substitution of 1,4-phenylenediacetyl chloride for the 1,3-phenylenediacetyl chloride used therein.

The non-ether linked monomers of Formulas XIII and XIV likewise may be conveniently prepared using those methods given in Example 5 herein. Said methods essentially comprise those methods used for the preparation of the non-ether linked monomer of Formula VII, with the substitution of 1,3-dibromobenzene for the bromobenzene used therein for the (b) acylation with 1,3- or 1,4-phenylenediacetyl chloride. Additionally, it is understood that the (d) bis(phenylethynylation) now becomes a tetrakis(phenylethynylation) due to the stoichiometric presence of 2 additional aryl bromide groups in the tetraketone precursor.

The dissymmetric monomers of Formulas X and XI may be conveniently prepared using those methods previously given herein. As a specific example, the dissymmetric monomer of Formula XI may be prepared via Friedel-Crafts monoacylation of phenyl ether with 3,5-dibromophenylacetyl chloride, wherein said monoacylation product is recovered from the product mixture via, for example, silica gel chromatography. The resultant monoacylation product, 4-[(3,5-dibromophenyl)acetyl]phenyl ether, is then monoacylated using phenylacetyl chloride, providing 4-[(3,5-dibromophenyl)acetyl]-4'-(phenylacetyl)phenyl ether. It is also operable to perform modified Kornblum oxidation of the 4-[(3,5-dibromophenyl)acetyl]phenyl ether monoacylation product to give the corresponding diketone prior to performing the second monoacylation. The aforementioned synthetic steps of (c) modified Kornblum oxidation of the acylation product using dimethylsulfoxide and hydrobromic acid, (d) bis(phenylethynylation) of the 3,5-dibromophenyl tetraketone product with phenylacetylene using palladium catalysis, a tertiary amine, and a solvent which is essentially inert to both reactants and product (e) bis(cyclopentadienone) formation via double Aldol reaction of the bis(phenylethynyl) tetraketone with 1,3-diphenylacetone using a quaternary ammonium hydroxide catalyst and one or more solvents which are essentially inert to both reactants and product, are then performed to provide the dissymmetric monomer of Formula XI.

The monomer of Formula XV may be conveniently prepared using those methods previously given herein. Specifically, Friedel-Crafts monoacylation of phenyl ether with 3,5-dibromophenylacetyl chloride is completed, wherein said monoacylation product is recovered from the product mixture via, for example, silica gel chromatography. The resultant monoacylation product, 4-[(3,5-dibromophenyl)acetyl]phenyl ether, is then monoacylated using 4-bromophenylacetyl chloride, providing 4-[(3,5-dibromophenyl)acetyl]-4'-[(4-bromophenyl)acetyl]phenyl ether. It is also operable to perform modified Kornblum oxidation of the 4-[(3,5-dibromophenyl)acetyl]phenyl ether monoacylation product to give the corresponding diketone prior to performing the second monoacylation. The aforementioned synthetic steps of (c) modified Kornblum oxidation of the acylation product using dimethylsulfoxide and hydrobromic acid, (d) phenylethynylation of the three bromophenyl groups in the tetraketone product with phenylacetylene using palladium catalysis, a tertiary amine, and a solvent which is essentially inert to both reactants and product (e) bis(cyclopentadienone) formation via double Aldol reaction of the tris(phenylethynyl) tetraketone with 1,3-diphenylacetone using a quaternary ammonium hydroxide catalyst and one or more solvents which are essentially inert to both reactants and product, are then performed to provide the monomer of Formula XV.

The monomer of Formula XXV may be conveniently prepared using those methods previously given herein. Specifically, Friedel-Crafts diacylation of bromobenzene with 5-bromo-1,3-phenylenediacetyl chloride is performed, followed by the aforementioned synthetic steps of (c) modified Kornblum oxidation of the diacylation product using dimethylsulfoxide and hydrobromic acid, (d) tris(phenylethynylation) of the tribromo tetraketone product with phenylacetylene using palladium catalysis, a tertiary amine, and a solvent which is essentially inert to both reactants and product (e) bis(cyclopentadiene) formation via double Aldol reaction of the tris(phenylethynyl) tetraketone with 1,3-diphenylacetone using a quaternary ammonium hydroxide catalyst and one or more solvents which are essentially inert to both reactants and product.

The monomer of Formula XXVI can be made via double alkdol condensation reaction of 4,4'-bis {[3,5,-bis(phenylethynyl)phenyl]glyoxalyl]} phenyl ether and 1,3-bis(4-phenylethynylphenyl-2-propanone.

The monomer of Formula XXVII can be made with (a) diacylation of a stoichiometric excess of diphenyl oxide with oxalyl chloride (b) diacylation with 3,5-dibromphenylacetyl chloride, (c) oxidation (d) tetra(phenylethynylation) and (e) condensation.

A monomer of Formula XXVIII can be made as shown in Example 40.

Additional exemplary monomers of the present invention, such as those given by Formulas from XVI to XIX are prepared using the synthetic methods given herein plus any other methods that may be apparent to the skilled artisan.

Once the monomers have been synthesized, they are preferably purified. In particular, in preparation for use as the organic polymer dielectrics for electronics applications, metal and ionic species must be removed. Preferably, these impurities can be removed by any known purification method including aqueous wash and recrystallizations.

Forming Curable Oligomers and Polymers

While not being bound by theory, it is believed that the polyphenylene oligomers and polymers are formed through the Diels-Alder reaction of a diene containing ring structure (e.g. cyclopentadienone group or pyrrone group) with a dienophile (e.g. an acetylene group) when the mixture of monomer and a suitable solvent are heated. The reaction temperature and time required for reaction will depend upon the degree of polymerization desired. In addition, at higher temperatures shorter reaction times are needed. Preferably, the B-staging (or partial polymerization) reaction occurs at a temperature of 100 to 300° C. for one to seventy-two hours. Careful monitoring of the B-staging (partial polymerization) reaction is advised to avoid premature gel formation. Depending upon when the B-staging reaction is terminated, there may be residual monomer left in the mixture after B-staging. One may determine the percentage of unreacted monomer by visible spectra analysis or SEC analysis. The number average molecular weight of the B-staged materials is preferably in the range of 2000 to 10,000.

Non-limiting examples of suitable solvents include mesitylene, methyl benzoate, ethyl benzoate, dibenzylether, diglyme, triglyme, diethylene glycol ether, diethylene glycol methyl ether, dipropylene glycol methyl ether, dipropylene glycol dimethyl ether, propylene glycol methyl ether, dipropylene glycol monomethyl ether acetate, propylene carbonate, diphenyl ether, cyclohexanone, butyrolactone and mixtures thereof. The preferred solvents are mesitylene, gamma-butyrolactone, cyclohexanone, diphenyl ether and mixtures of two or more of such solvents.

Alternatively, the monomers can be polymerized in one or more solvents at elevated temperature and the resulting solution of oligomers can be cooled and formulated with one or more additional solvents to aid in processing. In another approach, the monomer can be polymerized in one or more solvents at elevated temperature to form oligomers which can be isolated by precipitation into a non-solvent. These isolated oligomers can then be redissolved in a suitable solvent for processing.

Because of the unique structure of the monomers used, these B-staged or partially polymerized oligomers or polymers are characterized by being highly branched and by having the reactive groups (i.e. the dienophile and the ring structure comprising the conjugated carbon to carbon double bonds and the leaving group, preferably acetylene groups and cyclopentadienone groups) found in the backbone of the polymer as well as in pendant groups and as terminal groups. The benefit of this is that it may lead to relatively high cross-link density.

The monomers of this invention may also be useful as comonomers with other monomers capable of being copolymerized with these monomers e.g. by undergoing Diels-Alder reaction or acetylene acetylene reactions.

Processing of Curable Oligomer Formulations and Formation of Highly Cross-linked Structures The formulations with or without additives may be solvent coated, e.g. by spin-coating, onto a suitable substrate. These oligomers, particularly the preferred oligomers derived from cyclopentadienone and aromatic acetylene functional monomers, are useful in forming very low dielectric constant films in the manufacture of integrated circuit devices. Thus, it may be desirable to coat these oligomers onto a substrate comprising transistors and/or metal interconnects, although other types of substrates may be used as well.

Upon further heating, preferably to temperatures in the range of 200 to 450° C., of the solution or an article coated with the solution, additional reaction (e.g. crosslinking or chain extension) can occur through the Diels-Alder reaction of the remaining reactive ring groups (e.g. cyclopentadienone groups) with the remaining dienophile groups (e.g. acetylene groups) resulting in an increase in molecular weight. Additional cross-linking may also occur by reaction of the dienophile groups with each other—e.g. via acetylene/acetylene reactions. The cure reaction optionally may be performed on a hotplate or in an oven bake depending upon manufacturing plant design and efficiencies.

Other components that may be added to the formulations include fillers, such as glass beads, glass fibers, hollow spheres, graphite fibers, carbon black, polymeric powders; adhesion promoters, such as aromatic and aliphatic alkoxy or acyloxy silanes including silanes having reactive vinyl groups, and porogens.

Porogens are components which may be removed from the gelled polymer or, more preferably, the vitrified (i.e. fully cured or cross-linked) polymer by solvents or, more preferably, by thermal decomposition resulting in the formation of porosity. Suitable porogens include polystyrenes such as polystyrene and poly-α-methylstyrene; polyacrylonitriles, polyethylene oxides, polypropylene oxides, polyethylenes, polylactic acids, polysiloxanes, polycaprolactones, polyurethanes, polymethacrylates, polyacrylates, polybutadienes, polyisoprenes, polyamides, polytetrahydrofurans, polyvinyl chlorides, polyacetals, amine-capped alkylene oxides, random or block copolymers of such polymers, and hydrogenated or partially hydrogenated variations of such polymers. The porogens may be linear, branched, hyperbranched, dendritic, or star like in nature. Porogens preferably are characterized in that they form discrete domains in the matrix material. Some materials that are particularly suitable for forming such domains include: hyperbranched polymeric particles, dendrimers, and cross-linked particles as may be made for example by emulsion polymerization. Cross-linked, styrene based polymeric particles (preferably copolymers of styrene and a second monomer having at least two ethylenically unsaturated groups—e.g. divinyl benzene or di-isopropenyl benzene) having particle sizes of less than 30 nm, more preferably less than 20 nm are particularly suitable for use as porogens with the polymers of this invention as the matrix materials. See copending U.S. application Ser. No. 10/077,642 and 10/077,646, respectively. While the porogens may be added after B-staging it is also possible to add the porogens to the monomers prior to the B-staging reaction. In the latter case, without wishing to be bound by theory, it is believed that the porogens react with the monomers. However, whether a chemical bond is formed or whether other interaction (e.g. formation of interpenetrating network) occur, a graft between the particle and the monomer/oligomer is formed and is detected by SEC analysis. By grafting, it means matrix is either chemically bonded to the porogen or permanently entangled with porogen. Porogens may also be grafted to the B-staged material if added after some b-staging has already occurred by suitable heating provided the mixture does not gel.

Preferably, for substrates coated with films of the polymer of this invention, the film thickness is in the range of 50-1000 nm. For the preferred porous films, the percent porosity is preferably five to eighty percent, more preferably greater than 10 percent, most preferably greater than 15 percent, and more preferably less than 70 percent, most preferably less than 50 percent with pore sizes of 5-30, preferably 5-20, more preferably 5-15 nm.

EXAMPLES

Example 1

Synthesis of Product Containing Monomer of Formula II

A. Synthesis of 4-bromophenylacetyl Chloride

4-Bromophenylacetic acid (99.5 grams, 0.46 mole) and N,N-dimethylformamide (2 milliliters) were added under a dry nitrogen atmosphere to a predried one liter glass single neck round bottom Schlenk reactor containing a predried magnetic stirring bar. After sealing under dry nitrogen, the reactor was placed on a Schlenk line under slightly positive nitrogen pressure. Thionyl chloride (300 milliliters) was added under a dry nitrogen atmosphere to a predried glass addition funnel which was outfitted with a Schlenk adaptor, then sealed under dry nitrogen and placed on the Schlenk line. The reactor and addition funnel were coupled under dynamic nitrogen flow, after which the thionyl chloride was added dropwise to the stirred reactor. Nitrogen flow was maintained into the Schlenk reactor, while gas from the reaction vented through the Schlenk adaptor on the addition funnel and into a scrubber system. At the completion of the thionyl chloride addition, the addition funnel was replaced under dynamic nitrogen flow with a condenser capped with a Schlenk adaptor vented into the scrubber system, then a thermostatically controlled heating mantle was used to gently heat the reactor contents to 60° C. After holding for 2.5 hours at 60° C., the excess thionyl chloride was stripped from the product by applying vacuum from the Schlenk manifold until 60° C. and 159 microns was achieved. The resulting 4-bromophenylacetyl chloride product (105.95 grams, 98.1% isolated yield) was maintained under dry nitrogen until use.

B. Synthesis of 4,4'-bis[(4-bromophenyl)acetyl]phenyl Ether

Diphenyl ether (38.61 grams, 0.227 mole), aluminum chloride (60.53 grams, 0.454 mole) and anhydrous dichloromethane (250 milliliters) were added under a dry nitrogen atmosphere to a predried one liter glass single neck round bottom Schlenk reactor containing a predried magnetic stirring bar. After sealing under dry nitrogen, the reactor was placed on a Schlenk line under slightly positive nitrogen pressure. An ice bath was then placed under the reactor. 4-Bromophenylacetyl chloride (105.95 grams, 0.454 mole) from A. above dissolved in dichloromethane (100 milliliters) was added under a dry nitrogen atmosphere to a predried glass addition funnel which was outfitted with a Schlenk adaptor, then sealed under dry nitrogen and placed on the Schlenk line. The reactor and addition funnel were coupled under dynamic nitrogen flow, then the 4-bromophenylacetyl chloride solution was added dropwise to the stirred reactor over a 3 hour period. After 2 hours of post reaction, the reactor was removed from the Schlenk line and the contents poured over cracked ice contained in a 4 liter beaker. After complete melting of the ice, the precipitated product was dissolved into dichloromethane (14 liters) with the water layer removed using a separatory funnel. The dichloromethane solution was washed with deionized water (2 liters), then dried over anhydrous sodium sulfate. The resulting slurry was filtered through a medium fritted glass funnel, then the dry filtrate was passed through a column of silica gel, using additional dichloromethane (2 liters) eluent, as needed. The dichloromethane solution was rotary evaporated to dryness, giving 119.1 grams of white powder. High pressure liquid chromatographic (HPLC) analysis revealed the presence of the desired product at 94 area % accompanied by a single coproduct present at 6 area %. Recrystallization from boiling acetonitrile (14 liters) was completed (allowed to cool to room temperature and held therein for 16 hours) to provide, after recovery via filtration and drying in a vacuum oven, 96.0 grams (75.0% isolated yield) of 4,4'-bis[(4-bromophenyl)acetyl] phenyl ether as shimmering white platelike crystals with the HPLC analysis demonstrating complete removal of the coproduct (100 area % product). 1H Nuclear magnetic resonance (NMR) analysis confirmed the structure of the product.

C. Synthesis of 4,4'-bis[(4-bromophenyl)glyoxalyl]phenyl Ether 4,4'-bis[(4-Bromophenyl)acetyl]phenyl ether (95.5 grams, 0.169 mole) from B. above and dimethylsulfoxide (1.8 liters) were added to a two liter glass three neck round bottom reactor outfitted with a glass mechanical stirring rod with teflon paddles. The reactor was additionally outfitted with a chilled (2° C.) condenser vented into a scrubber system and a thermometer with thermostatically controlled heating mantle. Aqueous 48% hydrobromic acid (199.7 grams) was added as a stream over a 3 minute period to the stirred slurry in the reactor, inducing an exotherm to 45° C. Heating to 100° C. then commenced, with the formation of a clear light orange colored solution noted once 92° C. was achieved. After 2 hours at the 100° C. reaction temperature, the hot product solution was diluted into 8.2 liters of toluene followed by washing of the toluene solution five times with 1.6 liter portions of deionized water. The washed toluene solution was rotary evaporated to dryness, giving 99.2 grams (99.1% isolated yield) of light yellow colored powder. HPLC analysis revealed the presence of the desired product at 100 area %. 1H NMR analysis confirmed the structure of the product.

D. Synthesis of 4,4'-bis[(4-phenylethynylphenyl)glyoxalyl] phenyl Ether 4,4'-bis[(4-Bromophenyl)glyoxalyl]phenyl ether (99.2 grams, 0.1675 mole) from C above, phenylacetylene (41.37 grams, 0.405 mole), triethylamine (92.5 grams, 0.914 mole) which had been sparged with dry nitrogen, triphenylphosphine (2.22 grams, 0.00847 mole, palladium (II) acetate (0.31 gram, 0.00137 mole) and N,N-dimethylformamide (1063 milliliters), which had been sparged with dry nitrogen, were added under a dry nitrogen atmosphere to a predried two liter glass three neck round bottom reactor containing a predried magnetic stirring bar. The reactor was additionally outfitted with a fan cooled spiral condenser and a thermometer with a thermostatically controlled heating mantle. Stirring and heating commenced, and after 13 minutes, when a temperature of 45° C. was achieved, a clear light yellow colored solution formed. After a cumulative 1.2 hours, a temperature of 80° C. was achieved and maintained for the next 14.7 hours. At this time, HPLC analysis indicated that full conversion of the 4,4'-bis[(4-bromophenyl)glyoxalyl]phenyl ether reactant had been achieved. The reactor contents were poured over cracked ice contained in a pair of 4 liter beakers. After complete melting of the ice, the precipitated product was recovered via filtration through a medium fritted glass funnel. The product cake on the funnel was washed with two 500 milliliter portions of deionized water, then directly recrystallized, as a damp product, from boiling acetonitrile (22.5 liters). The recrystallization solution was allowed to cool to room temperature and held therein for 16 hours to provide 92.2 grams (86.7% isolated yield) of 4,4'-bis[(4-phenylethynyphenyll) glyoxalyl]phenyl ether as a light yellow crystalline product. HPLC analysis revealed the presence of the desired product at 100 area %. NMR analysis and electron ionization mass spectroscopic analysis (EI MS) both confirmed the structure of the product.

E. Synthesis of Product Containing 3,3'-(oxy-di-1,4-phenylene)-4,4'-bis [4-phenylethynylphenyl]-2,5-diphenylcyclopentadienone (Formula II)

A portion of the 4,4'-bis[(4-phenylethynylphenyl)glyoxalyl]phenyl ether (11.05 grams, 0.0174 mole) from D above, 1,3-diphenylacetone (7.76 grams, 0.0369 mole), anhydrous 1-propanol (1319 milliliters) and anhydrous toluene (70 milliliters), both of which had been sparged with dry nitrogen, were added under a dry nitrogen atmosphere to a predried two liter three-necked flask equipped with a magnetic stirrer. The reactor was additionally outfitted with a chilled (2° C.) condenser and a thermometer with a thermostatically controlled heating mantle. Stirring and heating commenced, and once the solution reached refluxing temperature, benzyltrimethylammonium hydroxide (40% in methanol, 1.86 grams) was added, immediately inducing a deep red purple color. After maintaining the reflux for 30 minutes, HPLC analysis indicated that full conversion of the 4,4'-bis[(4-phenylethynylphenyl)glyoxalyl]phenyl ether reactant had been achieved. At this time, heating ceased, the heating mantle was removed from the reactor, and the reaction mixture was allowed to cool to room temperature. The product was recovered via filtration through a medium fritted glass funnel. The crystalline product on the funnel was washed with two 50 milliliter portions of 1-propanol, then dried in a vacuum oven at 80° C. to provide 11.31 grams (66.1% isolated yield) of 3,3'-(oxy-di-1,4-phenylene)-4,4'-bis[4-phenylethynylphenyl]-2,5-diphenylcyclopentadienone (Formula II) as a deep purple red colored crystalline product. HPLC analysis demonstrated the presence of 75 area % of the monomer of Formula II accompanied by two minor coproducts. Electrospray ionization liquid chromatographic mass spectroscopic analysis (ESI LC MS) confirmed the structure of the peak comprising 75 area % in the HPLC analysis as that of Formula II.

Example 2

Synthesis of Monomer of Formula II

A. Synthesis of 4,4'-bis[(4-bromophenyl)glyoxalyl]phenyl Ether 4,4'-bis[(4-Bromophenyl)acetyl]phenyl ether (44 grams, 0.078 mole) from the similar procedure as shown in 1 B and dimethylsulfoxide (600 ml) were added to a two liter glass three neck round bottom reactor with magnetic stirring. Aqueous 48% hydrobromic acid (100 grams) was added with an additional funnel in three minutes. Heating to 90° C. then commenced, with the formation of a clear light orange colored solution noted once this temperature was achieved. After 3 hours at the 90° C. reaction temperature, the hot product solution was diluted into 3 liters of toluene followed by washing of the toluene solution twice with 300 ml portions of deionized water. The washed toluene solution was rotary evaporated to dryness, giving 30 grams (65% isolated yield) of light yellow colored powder. HPLC analysis revealed the presence of the desired product at 100 area %. 1H NMR analysis confirmed the structure of the product.

B. Synthesis of 4,4'-bis[(4-phenylethynylphenyl)glyoxalyl] phenyl Ether

In a 500 ml flask were placed 29.6 grams (0.05 mole) of 4,4'-bis[(4-bromophenyl)glyoxalyl]phenyl ether from 2 A above, 29 grams (0.29 mole) of triethylamine, 12.2 grams (0.12 mole) of phenylacetylene, and 120 milliliters of N,N-dimethylformamide. The reaction mixture was purged with nitrogen for 15 minutes and then 0.60 gram (0.0023 mole) of triphenylphosphine and 0.10 gram (0.00045 mole) of palladium acetate were added. After heating the reaction mixture at 80° C. under nitrogen atmosphere for 3 hours, the flask was allowed to cool to room temperature, and water (200 milliliters) was added. The solid product was filtered and dissolved into 2 liters of toluene. The organic solution was washed with 10% aqueous HCl, water and saturated aqueous NaCl then dried with anhydrous $Na_2SO_4$. The toluene solution was then passed through a silica gel filter and the pure product (23.3 grams, 73% isolated yield) was obtained upon removal of the toluene and recrystallization from toluene/hexanes.

C. Synthesis of Monomer of Formula II 4,4'-bis[(4-Phenylethynylphenyl)glyoxalyl]phenyl ether (12.7 grams, 0.01 mole) from 2 B above, and 1,3-diphenylacetone (9.45 grams, 0.045 mole) were added to 300 milliliters of anhydrous 1-propanol. Stirring and heating commenced, and once the suspension reached refluxing temperature, benzyltrimethylammonium hydroxide (40% in methanol, 3 ml) was added in 1.5 milliliter portions, immediately inducing a deep red purple color. After maintaining the reflux for 2 hours, HPLC analysis indicated that full conversion of the 4,4'-bis [(4-phenylethynylphenyl)glyoxalyl]phenyl ether reactant had been achieved. At this time, the oil bath was removed from the reactor, and the reaction mixture was allowed to cool to room temperature. The product was recovered via filtration through a medium fritted glass funnel. The crystalline product on the funnel was washed with two 100 milliter portions of 1-propanol, then dried in a vacuum oven to provide 16.1 grams (91% isolated yield) of monomer with greater than 91% purity by HPLC analysis.

Example 3

Synthesis of Monomer of Formula III

A. Synthesis of Ethyl 4-bromophenylacetate

A solution of 63 grams (0.29 mole) of 4-bromophenyl acetic acid and 50 milliliters of concentrated sulfuric acid in 500 milliliters of absolute ethanol was refluxed for 8 hours then allowed to stand overnight. After pouring over 600 grams of ice, the mixture was extracted with ether/hexanes. The ether extracts were washed thoroughly with water and sodium bicarbonate solution then dried over anhydrous sodium sulfate. Removal of the solvent by rotary evaporation yielded 57 grams (0.24 mole, 80% isolated yield) of an oil which crystallized upon cooling. Filtration and washing with hexane afforded pure product.

B. Synthesis of γ-(4-bromophenylaceto)-α-phenylacetonitrile

Sodium (6.0 grams, 0.26 mole) was added to 90 milliliters of absolute ethanol in a 250 milliliter three necked flask equipped with a stirrer, a condenser and a dropping funnel. While this solution was refluxing with stirring, a mixture of 30.37 grams of ethyl 4-bromophenyl acetate (0.125 mole) and benzyl cyanide (17.5 grams, 0.15 mole) was added through the dropping funnel over a period of 1 hour. The solution was refluxed for 3 hours, cooled then poured into 400 milliliters of cold water. The aqueous alkaline solution was extracted three times with 100 milliliter portions of diethylether and the ether extracts discarded. The aqueous solution was acidified with cold 10% aqueous hydrochloric acid then extracted three times with 100 milliliter portions of ether. The ether solution was then extracted once with 100 milliliters of water, twice with 100 milliliter portions of 10% aqueous sodium bicarbonate solution and once with 100 milliliters of water, the aqueous extracts being discarded in turn. The organic phase was dried over anhydrous sodium sulfate, filtered through a fluted filter and the ether removed by rotary evaporation. The desired product (33 grams) was recovered in 89% isolated yield.

C. Synthesis of 1-(4-bromophenyl)-3-phenyl-2-propanone

In a 250 three-necked flask equipped with a stirrer and a condenser were placed 75 milliliters of 60% aqueous sulfuric acid and 30 grams of the acetonitrile derivative prepared in B. above. While being stirred, the mixture was heated at reflux until the evolution of carbon dioxide ceased. The mixture was cooled, poured into 200 milliliters of ice water then extracted three times with 150 milliter portions of diethylether. The ether extract was washed once with 50 milliliters of water, twice with 100 milliliters portions of 10% aqueous sodium hydroxide, and then with 50 milliliters of water. After drying over anhydrous sodium sulfate and filtering, the ether was removed by rotary evaporation, affording crude product. Recrystallization from 160 milliliters of hexanes gave 11.5 grams (42% isolated yield) of product as a colorless solid.

D. Synthesis of 1-(4-phenylethynylphenyl)-3-phenyl-2-propanone

In a 250 ml flask was placed 10.9 grams (0.04 mole) of 1-(4-bromophenyl) 3-phenyl-2-propanone, 10 grams (0.10 mole) of triethylamine, 4.6 grams (0.045 mole) of phenylacetylene, and 50 milliliters of N,N-dimethylformamide. The reaction mixture was purged with nitrogen for 15 minutes, then 0.47 gram (0.0018 mole) of triphenylphosphine and 0.067 gram (0.0003 mole) of palladium acetate were added. After heating the reaction mixture at 80° C. under a nitrogen atmosphere for 2 hours, the flask was allowed to cool to room temperature, and water (200 milliliters) and diethylether (200 milliliters) were added. The resulting organic layer was washed with 10% aqueous HCl, water and saturated aqueous NaCl then dried over anhydrous $Na_2SO_4$. The pure product (8.5 grams, 72% isolated yield) was obtained upon removal of the ether and recrystallization from toluene/hexanes.

E. Synthesis of Monomer of Formula III 4,4'-bis (Phenylglyoxalyl)phenyl ether (2.9 grams, 0.0068 mole) and 4.0 grams (0.0135 mole) of 1-(4-phenylethynylphenyl)-3-phenyl-2-propanone from D. above were added to 100 milliliters of anhydrous 1-propanol. Stirring and heating commenced, and once the suspension reached reflux temperature, benzyltrimethylammonium hydroxide (40% in methanol, 0.7 milliter) was added, immediately inducing a deep red purple color. After maintaining at reflux for 1 hour, HPLC analysis indicated that full conversion of the 4,4'-bis (phenylgloxalyl)phenyl ether reactant had been achieved. At this time, the oil bath was removed from the reactor, and the reaction mixture was allowed to cool to room temperature. The product was recovered via filtration through a medium fritted glass funnel. The crystalline product on the funnel was washed with two 100 milliter portions of 1-propanol, then dried in a vacuum oven to provide 6.1 grams (93% isolated yield) of monomer of Formula III, which is a mixture of 3 isomers in a ratio of 1:2:1.

Example 4

Synthesis of Monomer of Formula IV

A. Synthesis of 1,3-bis(4-bromophenyl)-2-propanone

To a slurry of sodium hydride (9.17 grams, 0.23 mole) in 50 milliliters of toluene was added dropwise, a solution of ethyl 4-bromophenylacetate (50 grams, 0.21 mole) in toluene (50 milliliters) at 30-32° C. After addition was completed, the reaction mixture was slowly warmed to 50° C. where the reaction began to rapidly exotherm with evolution of hydrogen gas. The reaction mixture was further heated to 78° C. for 2 hours, cooled to room temperature and then HCl (45 grams) in water (22.5 grams) was slowly added dropwise to neutralize the solution. The layers were separated and the aqueous phase was extracted with diethylether. The combined organic extracts were dried and the solvent was removed to leave a yellow oil. This oil was refluxed for 24 hours in a mixture of glacial acid (60 milliliters) and concentrated HCl (30 milliliters). After cooling, the layers were separated, and the organic layer solidified to provide a yellow solid. This crude product was recrystallized from n-heptane to give a pure product as a white solid (31.2 grams, 82% isolated yield).

B. Synthesis of 1,3-bis(4-phenylethynylphenyl)-2-propanone

In a 250 ml flask was placed 18.4 grams (0.05 mole) of 1,3-bis-(4-bromophenylphenyl)-2-propanone, 24 grams (0.24 mole) of triethylamine, 12 grams (0.12 mole) of phenylacetylene, and 60 milliliters of N,N-dimethylformamide. The reaction mixture was purged with nitrogen for 15 minutes then 0.60 gram (0.0023 mole) of triphenylphosphine and 0.08 gram (0.00036 mole) of palladium acetate were added. After heating the reaction mixture at 80° C. under a nitrogen atmosphere for 20 hours, the flask was allowed to cool to room temperature, then water (200 milliliters) and toluene (200 milliliters) were added. The resulting organic layer was washed with 10% aqueous HCl, water and saturated aqueous NaCl then dried over anhydrous $Na_2SO_4$. The pure product (14.5 grams) was obtained upon removal of the toluene and recrystallization from toluene/hexanes in 71% isolated yield.

C. Synthesis of Monomer of Formula IV 4,4'-bis(Phenylglyoxalyl)phenyl ether (TK-1, 4.4 grams, 0.01 mole) and 8.2 grams (0.02 mole) of 1,3-bis(4-phenylethynylphenyl)-2-propanone from B above were added to a reactor containing 200 milliliters of anhydrous 1-propanol. Stirring and heating commenced, and once the suspension reached reflux temperature, benzyltrimethylammonium hydroxide (40% in methanol, 1.0 milliter in two 0.5 milliter portions) was added, immediately inducing a deep red purple color. After maintaining at reflux for 2 hours, HPLC analysis indicated that full conversion of the 4,4'-bis(phenylgloxalyl) phenyl ether reactant had been achieved. At this time, the oil bath was removed from the reactor, and the reaction mixture was allowed to cool to room temperature. The product was recovered via filtration through a medium fritted glass funnel. The crystalline product on the funnel was washed with two 100 milliter portions of 1-propanol, then dried in a vacuum oven to provide 10.3 grams (87% isolated yield) of the monomer of Formula IV.

Example 5

Synthesis of a Non-Ether Linked Monomer of Formula VII

A. Synthesis of 1,3-phenylenediacetyl Chloride Via Potassium 1,3-phenylenediacetate Potassium hydroxide (99.99%) (7.41 grams, 0.132 mole) was added to deionized water (300 milliliters) and stirred to form a solution. 1,3-Phenylenediacetic acid (11.65 grams, 0.06 mole, 0.12-COOH equivalent) was added to the aqueous potassium hydroxide solution, followed by gentle heating of the slurry until a solution formed. The resultant solution was rotary evaporated to dryness, followed by drying in the vacuum oven for 16 hours at 80° C. and 1 mm Hg. Additional drying was completed on a high vacuum line at 24° C. until a vacuum of 400 millitorr was achieved. The white powder product (16.0 grams) was recovered and held under a dry nitrogen atmosphere. In the dry nitrogen glovebox, the dipotassium salt was loaded into a 500 milliliter single neck round bottom Schlenk flask containing a magnetic stirring bar. All glassware and equipment used in the glove box had been previously dried to remove any moisture. Anhydrous dichloromethane (100 milliliters) was then added. After sealing under dry nitrogen, the reactor was removed from the glovebox, then placed on a Schlenk line under slightly positive nitrogen pressure. Thionyl chloride (100 grams) was added under a dry nitrogen atmosphere to a glass addition funnel which was outfitted with a Schlenk adaptor, then sealed and placed on the Schlenk line. The reactor and addition funnel were coupled under dynamic nitrogen flow, after which all thionyl chloride was added over a 24 minute period to the stirred slurry in the reactor. After an additional 55 minutes, N,N-dimethylformamide (0.35 milliliter) was injected into the fine white stirred slurry. During the entire reaction, dynamic nitrogen flow was maintained in the Schlenk reactor, while gases from the reaction vented through the Schlenk adaptor on the addition funnel and into a scrubber system. After an additional 83 minutes, the reactor was sealed under nitrogen, then placed in the glovebox. Using a thermostatically controlled heating mantle, the reactor contents were gently heated to 30° C. and the excess thionyl chloride and dichloromethane solvent were stripped from the product by applying vacuum from the glovebox vacuum line until 30° C. and 710 millitorr was achieved. The product in the reactor was extracted with 3 portions (100 milliliters) of anhydrous (chromatographically purified on alumina under dry nitrogen) diethyl ether, with each extract being passed through a medium fritted glass funnel into a one liter single neck round bottom Schlenk flask containing a magnetic stirring bar. Using a thermostatically controlled heating mantle, the reactor contents were gently heated to 30° C. and the diethyl ether solvent was stripped from the combined extract by applying vacuum from the glovebox vacuum line until 32° C. and 730 millitorr was achieved. The resulting 1,3-phenylenediacetyl chloride (13.0 grams, 0.0562 mole, 0.1125-COCl equivalent, 93.7% isolated yield) was maintained under dry nitrogen until use.

B. Synthesis of 1,3-bis[(4-bromophenyl)acetyl]benzene

In the dry, nitrogen glovebox, bromobenzene (157.0 grams, 1.0 mole) was added to the reactor containing 1,3-phenylenediacetyl chloride (13.0 grams, 0.0562 mole, 0.1125 COCl equivalent) from A above. Stirring commenced and aluminum chloride (18.0 grams, 0.135 mole) was added to the stirred solution in 0.5 gram aliquots every 3 minutes. At the end of the aluminum chloride addition, the dark amber stirred solution was held for one hour at 24° C. then analyzed by HPLC. The HPLC analysis demonstrated full conversion of the 1,3-phenylenediacetyl chloride. The reactor was removed from the glovebox and the contents poured over cracked ice contained in a 4 liter beaker. After complete melting of the ice, the precipitated product was dissolved into dichloromethane (1 liter) with the water layer removed using a separatory funnel. The dichloromethane solution was washed with deionized water (500 milliliters), then dried over anhydrous sodium sulfate. The resulting slurry was filtered through a medium fritted glass funnel, then the dry filtrate was rotary evaporated to give 30.2 grams of yellow powder (still damp with bromobenzene). Recrystallization from boiling acetonitrile was completed (allowed to cool to room temperature and held therein for 16 hours) to provide 17.54 grams (0.0372 mole, 66.1% isolated yield) of 1,3-bis[(4-bromophenyl) acetyl]benzene with the HPLC analysis demonstrating complete removal of impurities (100 area % product). Chilling the acetonitrile filtrate provided an additional 2.1 grams of product.

C. Synthesis of 1,3-bis[(4-bromophenyl)glyoxalyl]benzene 1,3-bis[(4-Bromophenyl)acetyl]benzene (17.54 grams, 0.0372 mole) from B above and dimethylsulfoxide (473 milliliters) were added to a one liter glass three neck round bottom reactor containing a magnetic stirring bar. The reactor was additionally outfitted with a chilled (2° C.) condenser and a thermometer with thermostatically controlled heating mantle. Aqueous 48% hydrobromic acid (43.8 grams) was added as a stream over a one minute period to the stirred slurry in the reactor, inducing an exotherm to 37° C. Heating to 100° C. then commenced, with the formation of a clear light amber solution noted once 72° C. was achieved. After 2.8 hours at the 100° C. reaction temperature, the bright yellow slurry was diluted while still hot into 3.4 liters of toluene followed by washing of the toluene solution five times with 400 milliliter portions of deionized water. The washed toluene solution was rotary evaporated to dryness, followed by further drying in the vacuum oven (80° C. and 1 mm Hg) giving 18.7 grams (100% isolated yield) of light yellow crystalline powder. HPLC analysis revealed the presence of the desired product at 100 area %.

D. Synthesis of 1,3-bis[(4-phenylethynylphenyl)glyoxalyl]benzene

A portion of the 1,3-bis[(4-bromophenyl)glyoxalyl]benzene (8.7 grams, 0.0174 mole, 0.0348 Br-equivalent) from C above, phenylacetylene (4.30 grams, 0.0421 mole), triethylamine (9.61 grams, 0.095 mole), triphenylphosphine (0.23 gram, 0.00088 mole), palladium (II) acetate (0.032 gram, 0.00014 mole) and N,N-dimethylformamide (174 milliliters), were added under a dry nitrogen atmosphere to a predried glass two liter three neck round bottom reactor containing a predried magnetic stirring bar. Both the triethylamine and the N,N-dimethylformamide had been sparged with dry nitrogen prior to use. The reactor was additionally outfitted with fan cooled spiral condenser and a thermometer with thermostatically controlled heating mantle. Stirring and heating commenced, and after 24 minutes, when a temperature of 78° C. was achieved, a clear light amber solution formed. After a cumulative 47 minutes, a temperature of 80° C. was achieved and maintained for the next 19.5 hours. At this time, HPLC analysis indicated that full conversion of the 1,3-bis[(4-bromophenyl)glyoxalyl]benzene reactant had been achieved. The reactor contents were poured over cracked ice contained in a 4 liter beaker. After complete melting of the ice and dilution to 2 liters volume with deionized water, the precipitated product was recovered via filtration through a medium fritted glass funnel. The product cake on the funnel was washed with 200 milliliters of deionized water, then a portion was analyzed by HPLC demonstrating the presence of 91.6 area % of the desired product. After boiling as a slurry in acetonitrile (1.8 liters), then holding for 18 hours at room temperature with stirring, 8.55 grams (90.6% isolated yield) of 1,3-bis[(4-phenylethynylphenyl)glyoxalyl]benzene was recovered as a light yellow powder after filtration on a medium fritted glass funnel followed by drying in the vacuum oven (40° C. and 1 mm Hg). HPLC analysis revealed the presence of the desired product at 100 area %. EI MS confirmed the structure of the product.

E. Synthesis of 3,3'-(1,3-phenylene)-4,4'-bis[(4-phenylethynyl)phenyl]-2,5-diphenylcyclopentadienone (Non-Ether Linked Monomer) (Formula VII)

A portion of the 1,3-bis[(4-phenylethynylphenyl)glyoxalyl]benzene (8.47 grams, 0.0156 mole) from D above, 1,3-diphenylacetone (6.96 grams, 0.0331 mole), anhydrous 1-propanol (1400 milliliters) and anhydrous toluene (80.5 milliliters), both of which had been sparged with dry nitrogen, were added under a dry nitrogen atmosphere to a predried 2 liter glass three neck round bottom reactor containing a predried magnetic stirring bar. The reactor was additionally outfitted with fan cooled spiral condenser and a thermostatically controlled heating mantle using a thermocouple for direct reading of the heating mantle surface temperature. Stirring and heating commenced, and once a refluxing clear light yellow colored solution formed, benzyltrimethylammonium hydroxide (40% in methanol) (1.43 grams) was added, immediately inducing a deep red solution. After maintaining the reflux for 45 minutes, HPLC analysis indicated that full conversion of the 1,3-bis[(4-phenylethynylphenyl)glyoxalyl] benzene reactant had been achieved. At this time, the heating mantle was removed from the reactor, and the stirred contents were maintained at 24° C. for the next 18 hours. The product was recovered via filtration through a medium fritted glass funnel. The product cake on the funnel was washed with two 20 milliliter portions of 1-propanol, then dried in a vacuum oven to provide 12.60 grams (90.6% isolated yield) of 3,3'-

(1,3-phenylene)-4,4'-bis[4-phenylethynylphenyl]-2,5-diphenylcyclopentadienone (Formula VII) as a deep purple red colored crystalline product.

Example 6

B-Staging of Product Containing Monomer of Formula II from Example 1 and Monomer of Formula II from Example 2

In a dry nitrogen glove box, a portion (5.94 grams) of the product containing the monomer of Formula II from Example 1 E above and γ-butyrolactone (13.86 grams), which had been sparged with dry nitrogen, were added to a 100 milliliter glass three neck round bottom reactor containing a 17 mm starhead TFE magnetic stirrer. The reactor was additionally outfitted with fan cooled spiral condenser and a thermometer with thermostatically controlled heating mantle. The heating mantle surface additionally possessed a thermocouple for direct reading of the surface temperature. Stirring commenced, and a sample of the homogeneous slurry was taken for gel permeation chromatography (GPC). All GPC analysis was completed using tetrahydrofuran as the eluent and polystyrene calibration standards. Heating commenced, and after 38 minutes, a temperature of 200° C. was achieved and maintained. The heating mantle surface temperature required to maintain the 200° C. internal temperature for the B-stage reaction ranged between 207° C. and 214° C. After 4, 6, and 7.5 hours of B-stage reaction, samples of the solution were taken and analyzed by GPC, with the following results:

| Sample (hr.) | Mn | Mw | Polydispersity |
|---|---|---|---|
| Initial | 1,000 | 910 | 0.91 |
| 4 | 3,170 | 7,940 | 2.50 |
| 6 | 5,040 | 30,400 | 6.03 |
| 75 | 6,640 | 137,200 | 20.66 |

At the 7.5 hour B-stage time, the reaction was stopped due to viscosity building which precluded adequate stirring. All samples were free of any visually observable gels.

In a similar procedure, a portion (4.0 grams) of the monomer from Example 2 C above and mesitylene (9.3 grams) were mixed and heated at reflux temperature (~170° C.) under nitrogen. After 2, 5, 12, 21, 26, 30 hours of B-stage reaction, samples of the solution were taken and analyzed by GPC, with the following results. All GPC analysis was completed using tetrahydrofuran as the eluent and polystyrene calibration standards.

| Sample (hr.) | Mn | Mw | Polydispersity |
|---|---|---|---|
| 2 | 1100 | 1250 | 1.13 |
| 5 | 1240 | 1550 | 1.25 |
| 12 | 1740 | 2560 | 1.47 |
| 21 | 2350 | 4470 | 1.87 |
| 26 | 2680 | 5850 | 2.18 |
| 30 | 3340 | 8550 | 2.56 |

Example 7

Differential Scanning Calorimetry of Monomer of Formula II

Differential scanning calorimetry (DSC) was completed using 3.2 and 3.0 milligram portions, respectively, of the monomer of Formula II from Example 2 C above. A DSC 2910 Modulated DSC (TA Instruments) was employed, using a heating rate of 7° C. per minute from 25° C. to 400° C. under a stream of nitrogen flowing at 45 cubic centimeters per minute. The results represent the average from the pair of analyses. A single endothermic transition was observed with a minimum at 240.9° C. (13.55 joules per gram). A single exothermic transition, attributable to Diels Alder reaction of phenylethynyl groups with cyclopentadienone groups, was observed with a maximum at 254.0° C. (158.0 joules per gram). The onset temperature for the exothermic transition was 242.0° C., while the ending temperature was 285.3° C. A second scanning using the aforementioned conditions revealed no glass transition temperature or any other transitions. The samples recovered from the DSC analysis were rigid light yellow colored fused transparent solid.

Example 8

Differential Scanning Calorimetry of Non-Ether Linked Monomer of Formula VII Differential scanning calorimetry (DSC) was completed using 4.2 and 4.0 milligram portions, respectively, of the non-ether linked monomer from Example 5 E above. A DSC 2920 Modulated DSC (TA Instruments) was employed, using a heating rate of 7° C. per minute from 25° C. to 500° C. under a stream of nitrogen flowing at 45 cubic centimeters per minute. The results represent the average from the pair of analyses. A single exothermic transition was observed with a maximum at 351.2° C. (169.3 joules per gram). The onset temperature for the exothermic transition was 308.8° C., while the ending temperature was 384.1° C. A second scanning using the aforementioned conditions revealed no glass transition temperature or any other transitions. The samples recovered from the DSC analysis were a non-fused, powdery solid.

Example 9

TICA Experiments to Determine the Modulus Profile of B-Staged Samples

The modulus profile of B-staged monomer of the type disclosed in Example 1 E and with or without porogens during cure were determined by evaluation of the formulation using torsional impregnated cloth analysis (TICA). In this technique a woven glass cloth (18×6.4×0.40 mm) was mounted in a dynamic mechanical analyzer, such as a TA DMA 2980. The ends of the cloth were wrapped in aluminum foil leaving 18 mm in length exposed. The cloth was then mounted in the vertical clamps of the dynamic mechanical analyzer and impregnated using a solution comprising the B-staged oligomers at 10 to 30% solids via a pipet. The cloth was thoroughly soaked and any excess was removed using the pipet. A heat deflector and oven were attached and a nitrogen flow of about 3 standard cubic feet per hour was established. The sample was heated to 430° C. at 7° C. per minutes, held there for 40 minutes, and then allowed to cool. Data analysis was performed to obtain temperature versus flexural modulus values for the composite of glass and formulation. Both B-staged monomer and B-staged monomer with porogen samples show in the TICA data that the solution was plasticized by solvent to give a mixture with very low modulus. Initial heating and solvent evaporation maintain the same glass modulus profile until the temperature reached 200° C., then modulus began to increase because of the Diels-Alder reaction between phenylacetylene and cyclopentadienone groups. At 300° C., the modulus of this glassy thermoset leveled out as cure was completed. There was no modulus increase or drop after 300° C. for this resin, as indicated by TICA plots.

Example 10

Preparation of Porous Matrix from Monomer of Formula II and Cross-Linked Polystyrene Porogens A. 20% 26 nm Cross-Linked Polystyrene Porogen To a 50 milliter round bottom flask was added 4 grams of monomer of Formula II, 1.0 gram crosslinked polystyrene nanoparticles (average particle size of 26 nm as measured by size exclusion chromatography employing a laser light scattering detector, made from microemulsion polymerization as discussed in copending application Ser. No. 10/077,642, and 9.3 grams of γ-butyrolactone (GBL). The resulting mixture was purged under nitrogen for 15 minutes and then heated to 200° C. with an oil bath under nitrogen for 8 hours. The mixture was then cooled to 145° C. and diluted with an equal amount of cyclohexanone. The mixture was finally allowed to cool to room temperature to give a 17.5% polymer mixture in GBL/cyclohexanone. Analysis of the final mixture by GPC demonstrated a Mn=3,588 and a Mw=24,905 relative to polystyrene standards and the graft ratio (i.e. weight of matrix which is grafted to porogen divided by weight of porogen) was 0.24.

The mixture was applied to a silicon wafer and cast by spin-coating to form a ~1.0 micron thick film. The film was baked on an MTI hotplate at 150° C. for 2 minutes, then the coated wafer was transferred to a vacuum oven. The oven temperature was ramped at 7° C./minute to 430° C. under nitrogen, then held for 40 minutes to allow the decomposition of polystyrene porogen before cooling. An estimate of the average spherical pore size based on visual inspection of a transmission electron micrograph (TEM) of the film was about 20 nm in diameter with the pore size ranging from 8 to 36 nm. The refractive index of the resulting film was 1.52.

B. 30% 26 nm Cross-Linked Polystyrene Porogen

To a 50 milliter round bottom flask was added 4 grams of monomer of Formula II, 1.72 grams of crosslinked polystyrene nanoparticles (average particle size of 26 nm as measured by size exclusion chromatography employing a laser light scattering detector, made from microemulsion polymerization) and 9.3 grams of GBL. The resulting mixture was purged under nitrogen for 15 minutes and then heated to 200° C. with an oil bath under nitrogen for 6 hours. The mixture was then cooled to 145° C. and diluted with an equal amount of cyclohexanone. The mixture was further cooled to room temperature to give a 17.5% polymer mixture in GBL/cyclohexanone. GPC analysis of the final mixture demonstrated a Mn=3,100 and a Mw=19,600 relative to polystyrene standards and the graft ratio was 0.19.

The mixture was applied to a silicon wafer and cast by spin-coating to form a ~1.0 micron thick film. The film was baked on an MTI hotplate at 150° C. for 2 minutes, then the coated wafer was transferred to a vacuum oven. The oven temperature was ramped at 7° C./minute to 430° C. under nitrogen, then held for 40 minutes to allow the decomposition of polystyrene porogen before cooling. An estimate of the average spherical pore size based on visual inspection of a TEM of the film was about 19 nm in diameter with the pore size ranging from 4 to 33 nm. The refractive index of the resulting film was 1.46 and the dielectric constant was 2.14.

C. 30% 30 nm Cross-Linked Polystyrene Porogen

To a 50 milliter round bottom flask was added 4 grams of monomer of Formula II, 1.72 grams of crosslinked polystyrene nanoparticles (average particle size 30 nm as measured by size exclusion chromatography employing a laser light scattering detector, made from microemulsion polymerization) and 9.3 grams of GBL. The resulting mixture 10 was purged under nitrogen for 15 minutes and then heated to 200° C. with an oil bath under nitrogen for 6 hours. The mixture was then cooled to 145° C. and diluted with an equal amount of cyclohexanone. The mixture was further cooled to room temperature to give a 17.5% polymer mixture in GBL/cyclohexanone. GPC analysis of the final mixture demonstrated a Mn=3,100 and a Mw=38,800 relative to polystyrene standards and the graft ratio was 0.19.

The mixture was applied to a silicon wafer and cast by spin-coating to form a ~1.0 micron thick film. The film was baked on an MTI hotplate at 150° C. for 2 minutes, then the coated wafer was transferred to a vacuum oven. The oven temperature was ramped at 7° C./minute to 430° C. under nitrogen, then held for 40 minutes to allow the decomposition of polystyrene porogen before cooling. An estimate of the average spherical pore size based on visual inspection of a TEM of the film was about 20 nm in diameter with the pore size ranging from 6 to 32 nm. The refractive index was 1.47 and the dielectric constant was 2.13.

D. 30% 25 nm Cross-Linked Polystyrene Porogen

To a 50 milliter round bottom flask was added 4 grams of monomer of Formula II, 1.72 grams of crosslinked polystyrene/10% poly(t-butylstyrene) nanoparticles (average particle size of 25 nm as measured by size exclusion chromatography employing a laser light scattering detector, made from microemulsion polymerization) and 9.3 grams of GBL. The resulting mixture was purged under nitrogen for 15 minutes and then heated to 200° C. with an oil bath under nitrogen for 8 hours. The mixture was then cooled to 145° C. and diluted with an equal amount of cyclohexanone. The mixture was further cooled to room temperature to give a 17.5% polymer mixture in GBL/cyclohexanone. GPC analysis of the final mixture demonstrated a Mn=3,200 and a Mw=19,800 relative to polystyrene standards and the graft ratio was 0.21.

The mixture was applied to a silicon wafer and cast by spin-coating to form a ~1.0 micron thick film. The film was baked on an MTI hotplate at 150° C. for 2 minutes, and the coated wafer was transferred to a vacuum oven. The oven temperature was ramped at 7° C./minute to 430° C. under nitrogen, then held for 40 minutes to allow the decomposition of poylstyrene porogen before cooling. An estimate of the average spherical pore size based on visual inspection of a TEM of the film was about 19 nm in diameter with the pore size ranging from 4 to 35 nm. The refractive index was 1.46 and the dielectric constant was 2.11.

E. 30% 13 nm Cross-Linked Polystyrene Porogen

To a 50 milliter round bottom flask was added 4 grams of monomer of Formula II, 1.72 grams of crosslinked polystyrene nanoparticles (13 nm as measured by size exclusion chromatography employing a laser light scattering detector, made from microemulsion polymerization) and 9.3 grams of GBL. The resulting mixture was purged under nitrogen for 15 minutes and then heated to 200° C. with an oil bath under nitrogen for 6 hours. The mixture was then cooled to 145° C. and diluted with an equal amount of cyclohexanone. The mixture was further cooled to room temperature to give a 17.5% polymer mixture in GBL/cyclohexanone. GPC analysis of the final mixture demonstrated a Mn=43,000 and a Mw=82,600 relative to polystyrene standards and the graft ratio was 0.37.

The mixture was applied to a silicon wafer and cast by spin-coating to form a 1.0 micron thick film. The film was baked on an MTI hotplate at 150° C. for 2 minutes, and the coated wafer was transferred to a vacuum oven. The oven temperature was ramped at 7° C./minute to 430° C. under nitrogen, then held for 40 minutes to allow the decomposition of polystyrene porogen before cooling. An estimate of the average spherical pore size based on visual inspection of a TEM of the film was about 12 nm in diameter with the pore size ranging from 5 to 18 nm. The refractive index was 1.47 and the dielectric constant was 2.12.

F. 35% 26 nm Cross-Linked Polystyrene Porogen

To a 50 milliter round bottom flask was added 4 grams of monomer of Formula II, 2.2 grams of crosslinked polystyrene nanoparticles (average particle size of 26 nm as measured by size exclusion chromatography employing a laser light scattering detector, made from microemulsion polymerization) and 9.3 grams of GBL. The resulting mixture was purged under nitrogen for 15 minutes and then heated to 200° C. with an oil bath under nitrogen for 6 hours. The mixture was then cooled to 145° C. and diluted with an equal amount of cyclohexanone. The mixture was further cooled to room temperature to give a 17.5% polymer mixture in GBL/cyclohexanone. GPC analysis of the final mixture demonstrated a Mn=3,200 and a Mw=39,400 relative to polystyrene standards and the graft ratio was 0.24.

The mixture was applied to a silicon wafer and cast by spin-coating to form a ~1.0 micron thick film. The film was baked on an MTI hotplate at 150° C. for 2 minutes, and the coated wafer was transferred to a vacuum oven. The oven temperature was ramped at 7° C./minute to 430° C. under nitrogen, then held for 40 minutes to allow the decomposition of polystyrene porogen before cooling. An estimate of the average spherical pore size based on visual inspection of a TEM of the film was about 21 nm in diameter with the pore size ranging from 7 to 37 nm. The refractive index was 1.43 and the dielectric constant was 1.98.

Example 11

Preparation of Porous Matrix from Monomer of Formula III and a Cross-Linked Polystyrene Porogen 30% 26 nm Cross-Linked Polystyrene Porogen To a 50 milliter round bottom flask was added 4 grams of monomer of Formula III, 1.72 grams of crosslinked polystyrene nanoparticles (average particle size of 26 nm as measured by size exclusion chromatography employing a laser light scattering detector, made from microemulsion polymerization) and 9.3 grams of γ-butyrolactone (GBL). The resulting mixture was purged under nitrogen for 15 minutes and then heated to 200° C. with an oil bath under nitrogen for 6 hours. The mixture was then cooled to 145° C. and diluted with an equal amount of cyclohexanone. The mixture was further cooled to room temperature to give a 17.5% polymer mixture in GBL/cyclohexanone.

The mixture was applied to a silicon wafer and cast by spin-coating to form a ~1.0 micron thick film. The film was baked on an MTI hotplate at 150° C. for 2 minutes, and the coated wafer was transferred to a vacuum oven. The oven temperature was ramped at 7° C./minute to 430° C. under nitrogen, then held for 40 minutes to allow the decomposition of polystyrene porogen before cooling. An estimate of the average spherical pore size based on visual inspection of a TEM of the film was about 20 nm in diameter with the pore size ranging from 6 to 33 nm. The refractive index of the resulting film was 1.46 and the dielectric constant was 2.19.

Example 12

Preparation of Porous Matrix from Monomer of Formula IV and a Cross-Linked Polystyrene Porogen 30% 13 nm Cross-Linked Polystyrene Porogen To a 50 milliter round bottom flask was added 4 grams of monomer of Formula IV, 1.72 grams of crosslinked polystyrene nanoparticles (average particle size of 13 nm as measured by size exclusion chromatography employing a laser light scattering detector, made from microemulsion polymerization) and 9.3 grams of γ-butyrolactone (GBL). The resulting mixture was purged under nitrogen for 15 minutes and then heated to 200° C. with an oil bath under nitrogen for 2 hours. The mixture was then cooled to 145° C. and diluted with an equal amount of cyclohexanone. The mixture was further cooled to room temperature to give a 17.5% polymer mixture in GBL/cyclohexanone.

The mixture was applied to a silicon wafer and cast by spin-coating to form a ~1.0 micron thick film. The film was baked on an MTI hotplate at 150° C. for 2 minutes, and the coated wafer was transferred to a vacuum oven. The oven temperature was ramped at 7° C./minute to 430° C. under nitrogen, then held for 40 minutes to allow the decomposition of polystyrene porogen before cooling. An estimate of the average spherical pore size based on visual inspection of a TEM of the film was about 10 nm in diameter with the pore size ranging from 6 to 19 nm. The refractive index of the resulting film was 1.45 and the dielectric constant was 2.15.

Example 13

Synthesis of High Purity Monomer of Formula II

A. Synthesis of High Purity 4,4'-bis[(4-bromophenyl)acetyl] phenyl Ether Diphenyl ether (200.96 grams, 1.1805 moles), aluminum chloride (321.15 grams, 2.409 moles) and anhydrous 1,2-dichloroethane (2.1 liters) were added under a dry nitrogen atmosphere to a predried five liter glass three neck round bottom reactor containing a predried magnetic stirring bar. After sealing under dry nitrogen, the reactor was placed on a Schlenk line under slightly positive nitrogen pressure. An ice and salt bath was then placed under the reactor 25 minutes before starting the reaction. 4-Bromophenylacetyl chloride (556.26 grams, 2.361 moles) prepared in the manner of Example 1 A herein was added under a dry nitrogen atmosphere to a predried glass addition funnel which was outfitted with a Schlenk adaptor, then sealed under dry nitrogen and placed on the Schlenk line. The reactor and addition funnel were coupled under dynamic nitrogen flow, then the 4-bromophenylacetyl chloride solution was added dropwise to the stirred reactor over a 3.7 hour period. After 2 hours of post reaction, magnetic stirring was shut off, the center port of the reactor was opened and a glass stirring shaft with teflon paddles was inserted then coupled to a variable speed motor to provide mechanical stirring of the reactor contents. A second port was opened and outfitted with an addition funnel containing chilled deionized water. Dropwise addition of chilled deionized water commenced simultaneous with mechanical stirring, inducing a massive precipitation of light yellow colored product after addition of the first few drops of water. Water addition continued until all orange red color was gone with a stirred slurry of white solid in a purple colored liquid remaining. The stirred slurry was maintained until cooling to 23° C. had occurred, at which time, filtration through a coarse fritted glass funnel commenced. After washing the packed bed of white powder on the filter with deionized water, it was removed, divided into 6 approximately equal portions, then washed in a Waring-blender with 250 milliliters of deionized water per portion. The washed product was recovered via filtration on a medium fritted glass funnel and drying in the vacuum oven at 80° C. to provide 498.3 grams (74.8% isolated yield) of 4,4'-bis[(4-bromophenyl)acetyl]phenyl ether. HPLC analysis revealed the presence of the desired product at 100 area %.

B. Synthesis of High Purity 4,4'-bis[(4-bromophenyl)glyoxalyl]phenyl Ether 4,4'-bis[(4-Bromophenyl)acetyl]phenyl ether (212.48 grams, 0.3766 mole) from A above and dimethylsulfoxide (3.1 liters) were added to a five liter glass three neck round bottom reactor outfitted with a glass mechanical stirring rod with teflon paddles. The reactor was additionally outfitted with a condenser (not chilled) vented into a scrubber system and a thermometer. Aqueous 48% hydrobromic acid (444.4 grams) was added dropwise over a 32 minute period to the stirred slurry in the reactor, inducing an exotherm to 39° C. A thermostatically controlled heating mantle was placed under the reactor and gentle heating over a 3.2 hour period to 100° C. then commenced, with the formation of a clear light amber colored solution noted once 75° C. was achieved. Once 92° C. was achieved, a bright yellow slurry formed. After 2 hours at the 100° C. reaction temperature the hot product solution was diluted into 12.7 liters of deionized water, then stirred as a slurry for the next 16 hours, followed by filtration on a coarse fritted glass funnel. After washing the packed bed of light yellow powder on the filter with deionized water, it was removed and dried in the vacuum oven at 100° C. to provide 222.09 grams (99.6% isolated yield) of 4,4'-bis[(4-bromophenyl)glyoxalyl]phenyl ether. HPLC analysis revealed the presence of the desired product at 100 area %.

C. Synthesis of High Purity 4,4'-bis[(4-phenylethynylphenyl)glyoxalyl]phenyl Ether 4,4'-bis[(4-Bromophenyl)glyoxalyl]phenyl ether (266.51 grams, 0.45 mole) prepared in the manner of B above, phenylacetylene (16.67 grams, 0.1632 mole), triethylamine (248.6 grams, 2.457 moles) which had been sparged with dry nitrogen, triphenylphosphine (5.97 grams, 0.2276 mole), palladium (II) acetate (0.83 gram, 0.0037 mole) and N,N-dimethylformamide (2854.5 grams), which had been sparged with dry nitrogen, were added under a dry nitrogen atmosphere to a predried five liter glass three neck round bottom reactor. The reactor was additionally outfitted with an addition funnel topped with a fan cooled spiral condenser, a thermometer with thermostatically controlled heating mantle, and a glass stirring shaft with teflon paddles which was coupled to a variable speed motor to provide mechanical stirring. Additional phenylacetylene (94.45 grams, 0.9247 mole) was added to the addition funnel. Stirring and heating commenced, and after 25 minutes, when a temperature of 47° C. was achieved, a clear light amber colored solution formed. After a cumulative 1.85 hours, a temperature of 80° C. was achieved and dropwise addition of the phenylacetylene commenced and was completed after 2.3 hours. After a cumulative 17 hours, HPLC analysis indicated that full conversion of the 4,4'-bis[(4-bromophenyl)glyoxalyl]phenyl ether reactant had been achieved, with no detectable monobromomonophenyethynyl intermediate present. At this time, the additional funnel was charged with deionized water (450 milliliters) which was added dropwise to the stirred solution, while holding the temperature at 80° C. After completion of the water addition, heating ceased and the stirred solution was allowed to slowly cool and crystallize, followed by filtration on a coarse fritted glass funnel. After washing the packed bed of yellow powder on the filter with deionized water, it was removed and dried in the vacuum oven at 100° C. to provide 257.32 grams (90.1% isolated yield) of 4,4'-bis[(4-phenylethynylphenyl)glyoxalyl]phenyl ether. HPLC analysis revealed the presence of the desired product at 100 area %.

D. Synthesis of High Purity 3,3'-(oxy-di-1,4-phenylene)-4,4'-bis[4-phenylethynylphenyl]-2,5-diphenylcyclopentadienone (Formula II)

A portion of the 4,4'-bis[(4-phenylethynylphenyl)glyoxalyl]phenyl ether (100.08 grams, 0.1577 mole) from C above, 1,3-diphenylacetone (74.61 grams, 0.3548 mole), 2-propanol (1334 milliliters) and toluene (1001 milliliters), were added to a five liter four neck Morton flask. The reactor was additionally outfitted with a chilled (2° C.) condenser, a thermometer with thermostatically controlled heating mantle, a Claisen adaptor with addition funnel and nitrogen sparge tube, and a glass stirring shaft with a turbine-type teflon stirrer which was coupled to a variable speed motor to provide mechanical stirring. The addition funnel was charged under a dry nitrogen atmosphere with 1M tetrabutylammonium hydroxide in methanol (8.34 milliliters) diluted into 2-propanol (166.4 milliliters). Stirring, sparging with nitrogen (1 liter per minute) and heating commenced, and once the stirred slurry reached 80° C., the sparge tube was removed and replaced with an overhead inlet for the nitrogen. Dropwise addition of the solution in the addition funnel to the refluxing stirred slurry commenced and was completed over the next 33 minutes, during which time, the yellow slurry was transformed to a deep red solution. Forty minutes after the addition of the catalyst solution, the red solution became a hazy red slurry, with evidence of grainy precipitate at the glass-liquid interface in the reactor. At this time, HPLC analysis indicated that full conversion of the 4,4'-bis[(4-phenylethynylphenyl)glyoxalyl]phenyl ether reactant had been achieved, concurrent with optimum formation of the desired product and minimum coproduct formation. After an additional 12 minutes, heating ceased, the heating mantle was removed from the reactor, additional 2-propanol (1.5 liters) was added to the reactor and the reaction mixture was cooled to room temperature using a cooling fan on the reactor exterior. Once the stirred slurry was at 24° C., the product was recovered via filtration through a coarse fritted glass funnel. The crystalline product on the funnel was washed with 2-propanol (200 milliliters), then loaded back into the reactor which had been rinsed with 2-propanol. After additional 2-propanol (1.2 liters) was added to the reactor, stirring for one hour commenced, followed by filtration on a coarse fritted glass funnel, washing with additional (200 milliliters) of 2-propanol on the funnel, and drying in a vacuum oven at 80° C. to provide 140.1 grams (90.4% isolated yield) of 3,3'-(oxy-di-1,4-phenylene)-4,4'-bis[4-phenylethynylphenyl]-2,5-diphenylcyclopentadienone (Formula II) as a deep purple colored crystalline powder. HPLC analysis demonstrated the presence of 98.56 area % of the monomer of Formula II with the balance comprising two minor coproducts.

Example 14

Differential Scanning Calorimetry of High Purity Monomer of Formula II

Differential scanning calorimetry (DSC) was completed using a 3.6 milligram portion of the high purity monomer of Formula II from Example 13 D above. A DSC 2910 Modulated DSC (TA Instruments) was employed, using a heating rate of 7° C. per minute from 25° C. to 500° C. under a stream of nitrogen flowing at 45 cubic centimeters per minute. A minor endothermic transition was observed with a minimum at 244.2° C. (18.95 joules per gram), an onset temperature of 234.6° C. and an ending temperature of 255.0° C. This was immediately followed by a major exothermic transition, attributable to Diels Alder reaction of phenylethynyl groups with cyclopentadienone groups, with a maximum at 259.3° C. (232.4 joules per gram). The onset temperature for this exothermic transition was 255° C., while the ending temperature was 352.0° C. A second scanning using the aforementioned conditions revealed no glass transition temperature or any other transitions. The sample recovered from the DSC analysis was a rigid yellow colored fused transparent solid.

Example 15

Preparation of Reduced Palladium Content 4,4'-bis [(4-phenylethynylphenyl)glyoxalyl]phenyl Ether and Conversion to Reduced Palladium Content High Purity Monomer of Formula II The synthesis of Example 13 C herein was repeated, with the following modification used to crystallize and recover the product: After a cumulative 14.5 hours, HPLC analysis indicated that full conversion of the 4,4'-bis[(4-bromophenyl) glyoxalyl]phenyl ether reactant had been achieved, with no detectable monobromomonophenylethynyl intermediate present. At this time, the addition funnel was charged with deionized water (225 milliliters) which was added dropwise to the stirred solution, while holding the temperature at 80° C. After completion of this initial water addition, sodium diethyldithiocarbamate trihydrate (8.33 grams, 0.037 mole) was added to the solution in the reactor. After 1.1 hours at the 80° C. temperature, the addition funnel was charged with deionized water (225 milliliters) which was added dropwise to the stirred solution, while holding the temperature at 80° C. After completion of the water addition, heating ceased and the stirred solution was allowed to slowly cool and crystallize, followed by filtration on a coarse fritted glass funnel. After washing the packed bed of yellow powder on the filter with deionized water (400 milliliters), it was removed, divided into 8 approximately equal portions, then washed in a Waring blender with 400 milliliters of deionized water per portion. The washed product was recovered via filtration on a medium fritted glass funnel and drying in the vacuum oven at 100° C. to provide 250.64 grams of 4,4'-bis[(4-phenylethynylphenyl) glyoxalyl]phenyl ether. HPLC analysis revealed the presence of the desired product at 100 area %. Neutron activation analysis of an aliquot of the product revealed the presence of 70+/−4 ppm of Pd. A 106.6 gram aliquot of the 4,4'-bis[(4-phenylethynylphenyl)glyoxalyl]phenyl ether was dissolved in warm toluene (2800 milliliters), then passed through a bed of silica gel, using additional toluene (700 milliliters) as eluent. The effluent from the silica gel chromatography was rotary evaporated to provide 105.47 grams of product which was dissolved into N,N-dimethylformamide (1129.5 grams) and charged to a two liter 3 neck round bottom reactor with magnetic stirring bar. The reactor was additionally outfitted with an addition funnel, a thermometer with thermostatically controlled heating mantle, and a chilled (2° C.) condenser. The addition funnel was charged with 89.1 milliliters of deionized water. Stirring and heating to 80° C. commenced, then deionized water was added dropwise to the stirred solution, while holding the temperature at 80° C. After completion of this initial water addition, sodium diethyldithiocarbamate trihydrate (3.36 grams, 0.0149 mole) was added to the solution in the reactor. After 4 hours at the 80° C. temperature, the addition funnel was charged with deionized water (89.1 milliliters) which was added dropwise to the stirred solution, while holding the temperature at 80° C. After completion of the water addition, heating ceased and the stirred solution was allowed to slowly cool and crystallize, followed by filtration on a coarse fritted glass funnel. After washing the packed bed of yellow powder on the filter with deionized water the damp product cake (141.1 grams) was dissolved in warm toluene (2400 milliliters), then passed through a bed of silica gel, using additional toluene (650 milliliters) as eluent. The effluent from the silica gel chromatography was passed through a second bed of fresh silica gel using the aforementioned method, then the effluent from the silica gel was rotary evaporated to provide 86.74 grams of product. Neutron activation analysis of an aliquot of the product revealed that Pd was nondetectable at a 0.1 ppm limit of detection. Conversion of this product to 3,3'-(oxy-di-1,4-phenylene)-4,4'-bis[4-phenylethynylphenyl]-2,5-diphenylcyclopentadienone (Formula II) using the synthetic method of Example 13 D herein likewise produced a high purity product with reduced palladium content.

Example 16

Preparation of Reduced Palladium Content 4,4'-bis [(4-phenylethynylphenyl)glyoxalyl]phenyl Ether and Conversion to Reduced Palladium Content High Purity Monomer of Formula II Using Recrystallization A sample (88.28 grams) of 4,4'-bis[(4-phenylethynylphenyl)glyoxalyl]phenyl ether containing 8.5+/−0.4 ppm Pd by neutron activation analysis was dissolved in a mixture of boiling toluene (798.7 grams), 2-propanol (199.75 grams) and deionized water (5.0 milliliters). The resultant solution was allowed to recrystallize, then the crystalline product recovered on a coarse fritted glass funnel and dried in the vacuum oven at 80° C. to provide 79.7 grams of pale yellow crystalline product. Neutron activation analysis of an aliquot of the product revealed that Pd was nondetectable at a 0.1 ppm limit of detection. Conversion of this product to 3,3'-(oxy-di-1,4-phenylene)-4,4'-bis[4-phenylethynylphenyl]-2,5-diphenylcyclopentadienone (Formula II) using the synthesis of Example 13 D herein likewise produced a product with reduced palladium content.

Example 17

Preparation of Monomer of Formula II with Low Metal and Ionics Content

The synthesis of Example 13 D herein was repeated to give 170 grams of 3,3'-(oxy-di-1,4-phenylene)-4,4'-bis[4-phenylethynylphenyl]-2,5diphenylcyclopentadienone (Formula II)

of 97.2 area % purity by HPLC analysis. This product was processed via silica gel chromatography using an eluent comprising 25% by volume tetrahydrofuran and 75% by volume toluene. The column and all glassware used for the chromatography were freed of contaminating metals and ionic materials by sequentially washing with dilute aqueous acid, electronic grade water and electronic grade 2-propanol. The packed silica gel bed was prewashed with tetrahydrofuran. Plastic receivers and plastic tools free of metals and ionic materials were used. The resulting effluent from the silica-gel chromatography was induced to crystallize via the addition of electronic grade 2-propanol. The resultant crystalline product was recovered via filtration and dried in a vacuum oven to give 158 grams (92.9% recovery) of the monomer of Formula II. Trace metals analysis of an aliquot of the product provided the following results: aluminum=73 ppb, calcium=210 ppb, chromium=5 ppb, copper=19 ppb, iron=30 ppb, lead=2 ppb, magnesium=16 ppb, manganese=1 ppb, nickel=4 ppb, potassium=40 ppb, sodium=300 ppb, zinc=86 ppb, with barium, beryllium, bismuth, cadmium, cesium, cobalt, gallium, indium, lithium, molybdenum, rubidium, silver, strontium, thorium, tin, titanium, vanadium, and zirconium all being below the limit of detection (the practical quantitation limit for all of these undetected metals was 10 ppb or less). Neutron activation analysis of an aliquot of the product revealed that Pd was nondetectable at a 0.1 ppm limit of detection.

Example 18

Synthesis of a Monomer of Formula VIII

A. Synthesis of 3-bromophenylacetyl Chloride

3-Bromophenylacetic acid (28.13 grams, 0.1308 mole) and N,N-dimethylformamide (0.56 milliliter) were added under a dry nitrogen atmosphere to a predried one liter glass single neck round bottom Schlenk reactor containing a predried magnetic stirring bar. After sealing under dry nitrogen, the reactor was placed on a Schlenk line under slightly positive nitrogen pressure. Thionyl chloride (207 milliliters) was added under a dry nitrogen atmosphere to a predried glass addition funnel which was outfitted with a Schlenk adaptor, then sealed under dry nitrogen and placed on the Schlenk line. The reactor and addition funnel were coupled under dynamic nitrogen flow, after which the thionyl chloride was added dropwise to the stirred reactor. Nitrogen flow was maintained into the Schlenk reactor, while gas from the reaction vented through the Schlenk adaptor on the addition funnel and into a scrubber system. At the completion of the thionyl chloride addition, the addition funnel was replaced under dynamic nitrogen flow with a condenser capped with a Schlenk adaptor vented into the scrubber system, then a thermostatically controlled heating mantle was used to gently heat the reactor contents to 60° C. After holding for 2.5 hours at 60° C., the excess thionyl chloride was stripped from the product by applying vacuum from the Schlenk manifold until 60° C. and 632 millitorr was achieved. The resulting 3-bromophenylacetyl chloride product (30.55 grams, 100% isolated yield) was maintained under dry nitrogen until use.

B. Synthesis of 4,4'-bis[(3-bromophenyl)acetyl]phenyl Ether

Diphenyl ether (11.13 grams, 0.06539 mole), aluminum chloride (117.79 grams, 0.1334 mole) and anhydrous 1,2-dichloroethane (1115 milliliters) were added under a dry nitrogen atmosphere to a predried 500 milliliter glass three neck round bottom reactor containing a predried magnetic stirring bar. After sealing under dry nitrogen, the reactor was placed on a Schlenk line under slightly positive nitrogen pressure. An ice and salt bath was then placed under the reactor 22 minutes before starting the reaction. 3-Bromophenylacetyl chloride (556.26 grams, 2.361 moles) from A above was added under a dry nitrogen atmosphere to a predried glass addition funnel which was outfitted with a Schlenk adaptor, then sealed under dry nitrogen and placed on the Schlenk line. The reactor and addition funnel were coupled under dynamic nitrogen flow, then the 3-bromophenylacetyl chloride solution was added dropwise to the stiffed reactor over an 83 minute period. After 3.8 hours of post reaction, the reactor was removed from the Schlenk line and the contents poured over cracked ice contained in a 4 liter beaker. After complete melting of the ice, the product was diluted with sufficient deionized water to bring the volume to one liter, then dichloromethane (1.15 liters) was added. The water layer was removed using a separatory funnel and the remaining dichloromethane solution was washed with deionized water (300 milliliters), then dried over anhydrous sodium sulfate. The resulting slurry was filtered through a medium fritted glass funnel. The filtrate was rotary evaporated to remove solvent, followed by further drying in the vacuum oven at 80° C. to provide 39.04 grams (apparent isolated yield exceeds 100%) of 4,4'-bis[(3-bromophenyl)acetyl]phenyl ether. HPLC analysis revealed the presence of the desired product at 76.7 area %.

C. Synthesis of 4,4'-bis[(3-bromophenyl)glyoxalyl]phenyl Ether 4,4'-bis[(3-Bromophenyl)acetyl]phenyl ether (39.04 grams, nominally 0.0692 mole) from B above and dimethylsulfoxide (750 milliliters) were added to a two liter glass three neck round bottom reactor outfitted with a glass mechanical stirring rod with teflon paddles. The reactor was additionally outfitted with a condenser (not chilled) vented into a scrubber system, a thermometer, and a thermostatically controlled heating mantle. Stirring and heating of the reactor contents commenced to give a solution at 35° C. Aqueous 48% hydrobromic acid (81.65 grams) was added dropwise over a 7 minute period to the stirred 35° C. solution in the reactor, inducing an exotherm to 49° C. Heating over a 42 minute period to 100° C. then commenced. After 2.9 hours at the 100° C. reaction temperature the hot product solution was diluted into 4 liters of deionized water, then stirred as a slurry for the next 16 hours, followed by filtration through a coarse fritted glass funnel. After washing the packed bed of light yellow powder on the filter with deionized water, it was removed and recrystallized as a damp product from boiling ethanol (allowed to cool to room temperature and held therein for 16 hours) to provide, after recovery via filtration and drying in the vacuum oven, 30.1 grams (73.5% isolated yield) of 4,4'-bis[(3-bromophenyl)glyoxalyl]phenyl ether. HPLC analysis revealed the presence of the desired product at 98.62 area %, accompanied by a single coproduct present as the balance. 1H NMR analysis confirmed the structure of the product.

D. Synthesis of 4,4'-bis[(3-phenylethynylphenyl)glyoxalyl]phenyl Ether

A portion of the 4,4'-bis[(3-bromophenyl)glyoxalyl]phenyl ether (21.56 grams, 0.0364 mole) from C. above, phenylacetylene (1.35 grams, 0.0132 mole), triethylamine (20.11 grams, 0.1987 mole) which had been sparged with dry nitrogen, triphenylphosphine (0.48 gram, 0.00183 mole), palladium (II) acetate (0.07 gram, 0.00031 mole) and N,N-dimethylformamide (231 grams), which had been sparged with dry nitrogen, were added under a dry nitrogen atmosphere to a predried two liter glass three neck round bottom reactor containing a predried magnetic stirring bar. The reactor was additionally outfitted with fan cooled spiral condenser, an addition funnel, and a thermometer with thermostatically controlled heating mantle. Additional phenylacetylene (7.64 grams, 0.0748 mole) was added to the addition funnel. Stirring and heating commenced and after 30 minutes, a temperature of 80° C. was achieved and dropwise addition of the phenylacetylene commenced and was completed after 20 minutes. After a cumulative 20.7 hours, HPLC analysis indicated that full conversion of the 4,4'-bis[(3-bromophenyl) glyoxalyl]phenyl ether reactant had been achieved, with no detectable monobromomonophenylethynyl intermediate present. The reactor contents were poured over cracked ice contained in a 4 liter beaker. After complete melting of the ice, the precipitated product was recovered via filtration through a medium fritted glass funnel. The product cake on the funnel was washed with two 200 milliliter portions of deionized water, then directly recrystallized as a damp product from boiling acetonitrile. The recrystallization solution was allowed to cool to room temperature and held therein for 16 hours to provide 13.87 grams (60% isolated yield) of 4,4'-bis [(3-phenylethynylphenyl)glyoxalyl]phenyl ether as a light tan crystalline product. HPLC analysis revealed the presence of the desired product at 98.43 area %, accompanied by a single coproduct present as the balance. 1H NMR analysis and EI MS analysis both confirmed the structure of the product.

E. Synthesis of 3,3'-(oxy-di-1,4-phenylene)-4,4'-bis[3-phenylethynylphenyl]-2,5-diphenylcyclopentadienone (Formula VIII)

A portion of the 4,4'-bis[(3-phenylethynylphenyl)glyoxalyl]phenyl ether (13.29 grams, 0.0209 mole) from D. above, 1,3-diphenylacetone (9.91 grams, 0.0471 mole), 2-propanol (177 milliliters) and toluene (133 milliliters), were added to a two liter four neck round bottom reactor. The reactor was additionally outfitted with a chilled (2° C.) condenser, a thermometer with thermostatically controlled heating mantle, a Claisen adaptor with addition funnel and nitrogen sparge tube, and a glass stirring shaft with a teflon blade stirrer which was coupled to a variable speed motor to provide mechanical stirring. The addition funnel was charged under a dry nitrogen atmosphere with 1M tetrabutylammonium hydroxide in methanol (1.11 milliliters) diluted into 2-propanol (22 milliliters). Stirring, sparging with nitrogen (0.5 liter per minute) and heating commenced, and once the stirred solution reached 80° C., the sparge tube was removed and replaced with an overhead inlet for the nitrogen. Addition of the solution in the addition funnel to the refluxing stirred solution commenced and was completed over the next 10 minutes, during which time, the yellow solution was transformed to a deep red purple solution. Fifteen minutes after the addition of the catalyst solution, the deep red purple solution became hazy. At this time, HPLC analysis indicated that full conversion of the 4,4'-bis[(3-phenylethynylphenyl)glyoxalyl]phenyl ether reactant had been achieved, concurrent with optimum formation of the desired product and minimum coproduct formation. After an additional 8 minutes, heating ceased, the heating mantle was removed from the reactor, additional 2-propanol (400 milliliters) was added to the reactor and the reaction mixture was cooled to room temperature using a cooling fan on the reactor exterior. Once the stirred slurry was at 25° C., the product was recovered via filtration through a medium fritted glass funnel. The crystalline product on the funnel was washed with 100 milliliters of 2-propanol, then loaded back into the reactor which had been rinsed with 2-propanol. After additional 2-propanol (400 milliliters) was added to the reactor, stirring for 15 minutes commenced, followed by filtration on a medium fritted glass funnel, washing with additional (50 milliliters) of 2-propanol on the funnel, and drying in a vacuum oven at 80° C. to provide 20.12 grams (97.7% isolated yield) of 3,3'-(oxy-di-1,4-phenylene)-4,4'-[3-phenylethynylphenyl]-2,5-diphenyl-cyclopentadienone as a purple colored crystalline powder. HPLC analysis demonstrated the presence of 96.3 area % of the monomer of Formula VIII with the balance comprising a single minor coproduct.

Example 19

Differential Scanning Calorimetry of Monomer of Formula VIII

Differential scanning calorimetry (DSC) was completed using a 3.8 milligram portion of the monomer of Formula VIII from Example 18 E. above. A DSC 2910 Modulated DSC (TA Instruments) was employed, using a heating rate of 7° C. per minute from 25° C. to 500° C. under a stream of nitrogen flowing at 45 cubic centimeters per minute. A minor endothermic transition was observed with a minimum at 195.3° C. (20.8 joules per gram), an onset temperature of 189.1° C. and an ending temperature of 222.1° C. This was immediately followed by a major exothermic transition, attributable to Diels Alder reaction of phenylethynyl groups with cyclopentadienone groups, with a maximum at 249.4° C. (243.4 joules per gram). The onset temperature for this exothermic transition was 222.1° C., while the ending temperature was 329.0° C. A second scanning using the aforementioned conditions revealed no glass transition temperature or any other transitions. The sample recovered from the DSC analysis was a rigid yellow colored fused transparent solid.

Example 20

Preparation of Porous Matrix from Monomer of Formula II and Star Polymers

A. Preparation of Reactive Star Polymer

A 2.5 L glass polymerization reactor, which had been washed with hot cyclohexane and dried under vacuum, was charged with 2 L of cyclohexane. The reactor was heated to 50° C. and 25.2 mL (10.86 mmoles) of 0.43 M sec-BuLi was added followed by 49.74 g of styrene and 74 mL of THF. The dark orange solution was stirred for 15 min. The polymerization was sampled (sample A) and 5.39 g (41.41 mmoles, 3.8 eq) of para-divinylbenzene, contained in cyclohexane, was added to give a very dark red solution. After 30 min, 47.5 g of styrene was added to give a dark orange solution. After 15 min, the reactor was sampled (sample B) and 4.8 g of ethylene oxide was added to give a colorless viscous solution. After 1 h, 5.44 g (22.60 mmoles, 2.1 eq) of 4-(phenylethynyl)benzoyl chloride contained in tetrahydrofuran was added. After an additional hour, the reactor was cooled and the contents were removed. An aliquot (sample C) of the final star was isolated by precipitation into MeOH. Results of the GPC analysis of the samples were as follows (data is relative to polystyrene standards except where labelled as absolute):

| Sample | $M_w$ | $M_n$ | $M_w/M_n$ |
|---|---|---|---|
| A | 4,700 | 4,100 | 1.15 |
| B | 77,400 | 69,400 | 1.12 |
| C | 96,000 | 77,400 | 1.24 |
| C (Absolute) | 345,000 | 241,000 | 1.43 |

Ultraviolet analysis showed the star contained an average of 2.25 wt % diphenylacetylene, or 22.6 diphenylacetylene units per star.

B. B-Staging of Reactive Star Polymer with Monomer Formula II

To a Schlenk tube was added 1.2857 grams of a reactive polystyrene star polymer from A. above (absolute Mn=241,000, absolute Mw=345,000, average number of diphenylacetylene moieties per star=23) and gamma-butyrolactone (8.75 g). The tube was connected to a static nitrogen source and immersed in an oil bath heated to 45° C. The mixture was stirred overnight. To the tube was then added monomer 11 (3.00 g). The mixture was stirred and degassed by the application of numerous vacuum/nitrogen cycles. The tube was left under a static nitrogen pressure and then the oil bath was heated to 200° C. and held there for 8.5 h. The tube was removed from the oil bath and allowed to cool. The mixture was diluted with cyclohexanone (8.3928 g). The mixture was analyzed by gel permeation chromatography indicating a Mn 3545 and a Mw=35,274 relative to a polystyrene standard.

C. Preparation of Porous Matrix from Monomer II and Reactive Star Polymer

The mixture from B above was spun coat onto a 4" silicon wafer, hot plate baked at 150° C. for 2 minutes to remove solvent, then heated to 430° C. at 7° C./min and held at 430° C. for 40 minutes in a nitrogen purged oven. The resultant porous film had a refractive index of 1.47 (compared to 1.64 for the fully dense polymer) and a dielectric constant of 2.13.

Example 21

Preparation of Porous Matrix from Monomer of Formula II and Hyperbranched Polymers A. Preparation of Reactive Hyperbranched Polyester To a mixture of 3.11 g of Boltorn H40 (commerical product of Perstorp Corp.) (0.439 mmol; 28.03 mmol —OH) in 40 ml of THF which had stirred for 15 min at room temperature was added 1.18 ml (0.860 g; 8.5 mmol) of $Et_3N$. The mixture was stirred for 15 min and then 2.03 g (8.41 mmol) of 4-(phenylethynyl)benzoyl chloride was added dropwise as a solution in 40 ml THF. The mixture was stirred at room temperature overnight. To the reaction mixture was then added 3.90 ml (28 mmol) of $Et_3N$ followed by 3.31 g (54 mmol; 2.7 ml) of benzoyl chloride. The mixture was stirred at room temperature overnight and then heated at gentle reflux for 4-6 hours. The reaction mixture was poured over ~200 g ice and 10 ml of conc. HCl with vigorous stirring. After 30 min the reaction mixture was taken up in 200 ml $CHCl_3$ and transferred to a separatory funnel where the aqueous layer was removed and the organic layer was washed with 10% HCl (2×100 ml); $H_2O$ (2×100 ml) and 5% $NaHCO_3$ (1×100 ml). The mixture was dried over $MgSO_4$. The mixture was filtered and concentrated to obtain a viscous liquid. The viscous liquid was further devolatilized by Kugelrohr distillation under full vacuum (Tmax=140° C.). The weight of the glassy product was 4.61 g; theoretical 6.87 g; Yield=67%.

B. B-Staging of Reactive Hyperbranched Polyester with Monomer Formula II

To a Schlenk tube was added 0.75 grams of a reactive hyperbranched polyester from A. above (Boltorn H-40 functionalized with 19.2 phenylethynylbenzoate groups and 44.8 benzoate groups) and gamma-butyrolactone (8.75 g). The tube was connected to a static nitrogen source and immersed in an oil bath heated to 45° C. The mixture was stirred overnight. To the tube was then added monomer II (3.00 g). The mixture was stirred and degassed by the application of numerous vacuum/nitrogen cycles. The tube was left under a static nitrogen pressure and then the oil bath was, heated to 200° C. and held there for 8.5 h. The tube was removed from the oil bath and allowed to cool. The mixture was diluted with cyclohexanone (6.25 g). The mixture was analyzed by gel permeation chromatography indicating a Mn=4001 and a Mw=23,838 relative to a polystyrene standard.

C. Preparation of Porous Matrix from Monomer II and Reactive Hyperbranched Polymer The mixture from B. above was spun coat onto a 4" silicon wafer, hot plate baked at 150° C. for 2 minutes to remove solvent, then heated to 430° C. at 7° C./min and held at 430° C. for 40 minutes in a nitrogen purged oven. The resultant porous film had a refractive index of 1.59 (compared to 1.64 for the fully dense polymer).

Example 22

Synthesis of a Monomer of Formula XII

A. Conversion of 3,5-dibromophenylacetic Acid to the Potassium Salt

A commercial grade (99.5 area % by HPLC analysis) of 3,5-dibromophenylacetic acid (292.95 grams, 1.0 mole) was added to a magnetically stirred solution of nominally 85% potassium hydroxide (69.3 grams) in deionized water (3.0 liters), followed by heating. At 51° C., a solution was formed and heating ceased. Rotary evaporation of the solution under vacuum at 60° C. provided a slightly damp white powder product (360.2 grams) which was recovered and then extracted sequentially with two portions (500 milliliters) of dichloromethane. The extracted powder product contained in a single neck round bottom glass flask was sealed using a Schlenk adaptor through which vaccum was introduced. The flask was additionally heated to 40° C. using a thermostatically controlled heating mantle and held on the vacuum line until a vacuum of 400 millitorr was achieved. The recovered weight of the potassium 3,5-dibromophenylacetate thus produced was 332.3 grams (contains the residual excess potassium hydroxide).

B. Synthesis of 3,5-dibromophenylacetyl Chloride

The potassium 3,5-dibromophenylacetate product from A. above (332.3 grams, nominally 1.0 mole) and anhydrous dichloromethane (2.0 liters) were added under a dry nitrogen atmosphere to a predried five liter glass three neck round bottom reactor. After sealing under dry nitrogen, the reactor was placed on a Schlenk line under slightly positive nitrogen pressure. Thionyl chloride (633.0 grams, 5.32 moles) was added under a dry nitrogen atmosphere to a predried glass addition funnel which was outfitted with a Schlenk adaptor, then sealed under dry nitrogen and placed on the Schlenk line. The reactor and addition funnel were coupled under dynamic nitrogen flow. Dynamic nitrogen flow continued to be maintained through the Schlenk adaptor on the addition funnel, so as to continuously sweep gas generated by the reaction out through a Schlenk adaptor on the reactor and into a scrubber system. Mechanical stirring (glass stirrer shaft with teflon paddle) of the reactor contents commenced to provide a stirred slurry to which thionyl chloride was added dropwise over a 64 minute period. Three minutes after the completion of the thionyl chloride addition, anhydrous N,N-dimethylformamide (2.9 grams) was injected into the stirred slurry. After stirring for an additional 2 hours, nitrogen flow to the reactor was shut off concurrent with the introduction of vacuum. Gentle heating commenced using a thermostatically controlled heating mantle set to a 75° C. surface temperature. A solid product was left in the reactor once the excess thionyl chloride distilled off. At this time, heating ceased and the vacuum was replaced by a nitrogen pad maintained under a slight positive pressure. The reactor was then sealed under nitrogen and introduced into a dry nitrogen glove box. Once inside the glove box, the reactor was reheated to 30° C. using a thermostatically controlled heating mantle and held on a vacuum line until a vacuum of 330 millitorr was achieved. The powder product recovered from the reactor was extracted sequentially with three portions (500, 300, and 300, milliliters, respectively) of anhydrous diethylether (obtained via column chromatographic drying over activated alumina under a dry nitrogen atmosphere). Each diethylether extract was decanted through a predried medium fritted glass funnel followed by addition of the combined diethylether extracts into a predried two liter glass three neck round bottom reactor containing a predried magnetic stirring bar. The stirred reactor was heated to 30° C. using a thermostatically controlled heating mantle with the application of vacuum to distill off the diethylether solvent. Once the visually observable diethylether had distilled off, the product was further held on the vacuum line for 6 hours at a vacuum ranging from 560 to 670 millitorr. The resulting 3,5-dibromophenylacetyl chloride product (304.7 grams, 97.5% isolated yield) was recovered as an off-white crystalline powder which was maintained under dry nitrogen until use.

A sample of the 3,5-dibromophenylacetyl chloride (0.1 gram) was added under a nitrogen atmosphere to a predried glass vial containing anhydrous methanol (1 milliliter). The solution was brought to a boil, then the methanol allowed to boil off. The residue left behind was dissolved into acetonitrile and analyzed by HPLC, revealing 100 area % of the methyl ester product.

Differential scanning calorimetry (DSC) was completed using a 12.2 milligram portion of the 3,5-dibromophenylacetyl chloride which had been sealed into an aluminum pan in the dry nitrogen glove box. A DSC 2910 Modulated DSC (TA Instruments) was employed, using a heating rate of 7° C. per minute from 0° C. to 100° C. under a stream of nitrogen flowing at 45 cubic centimeters per minute. A single endothermic transition was observed with a minimum at 51.4° C. and an enthalpy of 75.56 joules per gram, for the melting of the product.

C. Synthesis of 4,4'-bis[(3,5-dibromophenyl)acetyl]phenyl Ether

Anhydrous 1,2-dichloroethane (557 milliliters), aluminum chloride (66.32 grams, 0.4974 mole) and then diphenyl ether (41.09 grams, 0.2414 mole) were added under a dry nitrogen atmosphere to a predried 2 liter glass three neck round bottom reactor containing a predried magnetic stirring bar. After sealing under dry nitrogen, the reactor was placed on a Schlenk line under slightly positive nitrogen pressure. Stirring of the reactor contents commenced to provide a slurry. An ice and salt (NaCl) bath was placed under the reactor 20 minutes before starting the reaction. 3,5-Dibromophenylacetyl chloride (152.36 grams, 0.4876 mole) from B. above was dissolved in anhydrous 1,2-dichloroethane (517 milliliters) and the resultant solution added under a dry nitrogen atmosphere to a predried glass addition funnel. The addition funnel was outfitted with a Schlenk adaptor, then sealed under dry nitrogen and placed on the Schlenk line. The reactor and addition funnel were coupled under dynamic nitrogen flow which continued to be maintained through the Schlenk adaptor on the addition funnel, so as to continuously sweep gas generated by the reaction out through a Schlenk is adaptor on the reactor and into a scrubber system. The 3,5-dibromophenylacetyl chloride solution was added dropwise to the stirred reactor over a 168 minute period. During this time, the ice and salt bath was replenished as melting occurred. After 56 minutes of post reaction, the reactor was removed from the Schlenk line and the contents poured into a pair of 4 liter beakers each containing 1.5 liters of magnetically stirred deionized water which had been preheated to 40° C. The contents of the beakers exothermed to 60° C., then further heating was conducted until 90° C. was achieved and maintained until the 1,2-dichloroethane had distilled off. The resulting slurry of coarse white powder in each beaker was diluted with one liter of additional deionized water, immediately followed by vacuum filtration through a coarse fritted glass funnel. After washing the packed cake of powder on the fritted glass funnel with sufficient deionized water to cover, drying in the vacuum oven at 80° C. provided 176.87 grams (100% isolated yield) of 4,4'-bis[(3,5-dibromophenyl)acetyl] phenyl ether. HPLC analysis revealed the presence of the desired product at 96.02 area %.

D. Synthesis of 4,4'-bis[(3,5-dibromophenyl)glyoxalyl]phenyl Ether 4,4'-bis[(3,5-Dibromophenyl)acetyl]phenyl ether (175.95 grams, 0.2437 mole) from C. above and dimethylsulfoxide (3.62 liters) were added to a five liter glass three neck round bottom reactor outfitted with a glass mechanical stirring rod with teflon paddle. The reactor was additionally outfitted with a Claisen adaptor, an addition funnel, a condenser (not chilled) vented into a scrubber system, and a thermometer. Aqueous 48% hydrobromic acid (287.6 grams) was added dropwise over a 31 minute period to the stirred 25° C. slurry in the reactor, inducing an exotherm to 33.5° C. A thermostatically controlled heating mantle was then placed on the reactor and gentle heating commenced over a 107 minute period to 100° C. giving a light orange colored solution. (By "gentle heating", it is meant that heating was periodically shut off to observe for exothermicity and to allow equilibration). After 2 hours at the 100° C. reaction temperature HPLC analysis demonstrated that complete reaction had occurred. The hot product solution was diluted into four 4 liter beakers each containing 2.0 liters of magnetically stirred deionized water. The resulting stirred product slurry was maintained for the next 16 hours, followed by vacuum filtration through a medium fritted glass funnel. After washing the packed bed of light yellow powder on the filter with deionized water, it was removed and dried in the vacuum oven to provide 175.6 grams (96.1% isolated yield) of 4,4'-bis[(3,5-dibromophenyl) glyoxalyl]phenyl ether. HPLC analysis revealed the presence of the desired product at 97.0 area %, with the balance comprising a single minor coproduct present. EI MS analysis confirmed the structure of the product: The intact molecular ion was not observed due to the facile cleavage of internal bonds upon electron ionization. Ion clusters centered at m/z 487 and m/z 263 clearly reflected the isotopic pattern of 2 bromine atoms for fragment ions of the formula $C_{21}H_{11}O_4Br_2$ and of the formula $C_7H_{30}Br_2$, respectively. These fragments resulted from cleavage in one of the glyoxalyl groups. An ion cluster centered at m/z 235 was from a dibromophenyl ion. Ions at m/z 196 and m/z 139 (no bromine) arose from the center of the molecule. In order to observe the intact molecule for molecular ion confirmation, chemical ionization (CI) was performed (using isobutane at the CI reagent gas). In the positive CI mass spectrum the protonated molecular ion cluster was visible around 751 amu and possessed the isotopic pattern expected for the compound containing 4 bromine atoms.

E. Synthesis of 4,4'-bis[(3,5-bis(phenylethynyl)phenyl)glyoxalyl]phenyl Ether 4,4'-bis[(3,5-Dibromophenyl)glyoxalyl]phenyl ether (175.0 grams, 0.2333 mole) from D. above, N,N-dimethylformamide (3064 grams) which had been sparged with dry nitrogen, triethylamine (257.8 grams, 2.548 moles) which had been sparged with dry nitrogen, phenylacetylene (17.3 grams, 0.1694 mole), triphenylphosphine (6.19 grams, 0.0236 mole) and palladium (II) acetate (0.86 gram, 0.0038 mole) were added under a dry nitrogen atmosphere in the indicated order to a predried five liter glass three neck round bottom reactor outfitted with a glass mechanical stirring rod with teflon paddles. The reactor was additionally outfitted with a Claisen adaptor, a fan cooled spiral condenser, an addition funnel, and a thermometer with thermostatically controlled heating mantle. Additional phenylacetylene (97.9 grams, 0.9585 mole) was added to the addition funnel. Stirring and heating commenced and after 59 minutes, a temperature of 80° C. was achieved. Dropwise addition of the phenylacetylene to the stirred solution then commenced and was completed after 114 minutes with maintenance of temperature between 79° C. and 81° C. After an additional 24 hours at 80° C., HPLC analysis indicated that full conversion of the 4,4'-bis[(3,5-dibromophenyl)glyoxalyl]phenyl ether reactant had been achieved.

F. Palladium Removal from 4,4'-bis[(3,5-bis(phenylethynyl)phenyl)glyoxalyl]phenyl Ether Reaction Product The addition funnel previously used for the phenylacetylene addition was charged with deionized water (127 milliliters) which was added dropwise to the stirred solution from E. above, while continuing to hold the temperature at 80° C. Seven minutes after completion of this initial water addition, sodium diethyldithiocarbamate trihydrate (9.65 grams, 0.0428 mole) was added to the solution in the reactor. After 90 minutes at the 80° C. temperature, the addition funnel was charged with deionized water (477 milliliters) which was added dropwise to the stirred solution, while holding the temperature at 80° C. After completion of the water addition, heating ceased and the stirred slightly hazy solution was allowed to slowly cool and crystallize over the next 16 hours, followed by vacuum filtration on a medium fritted glass funnel. The packed bed of yellow powder was held on the filter until no further drops of filtrate were observed. The damp cake of product (303.2 grams) was removed from the filter and charged to a clean five liter glass three neck round bottom reactor outfitted with a glass mechanical stirring rod with teflon paddle. Toluene was then added to the reactor (1093 milliliters). The reactor was additionally outfitted with a chilled (2° C.) condenser, and a thermometer with thermostatically controlled heating mantle.

Stirring and heating to 85° C. commenced, then deionized water (1093 milliliters) was added to the reactor as a stream, followed by reheating to 85° C. After one hour at 85° C. (gentle reflux), heating and stirring ceased followed by transfer of the reactor contents to a separatory funnel. The aqueous layer was removed and discarded, followed by addition of the toluene solution back into the reactor, stirring and reheating to 85° C. and addition of a second portion of deionized water (1093 milliters). After one hour at 85° C., heating and stirring ceased followed by transfer of the reactor contents to a separatory funnel. The aqueous layer was removed and discarded, followed by addition of the toluene solution back into the reactor, stirring and reapplication of heat. Three minutes later, 2-propanol (1093 milliliters) was added as a stream to the stirred solution. Once all 2-propanol had been added, the solution was at 40° C. and stirring and heating ceased, with maintenance of the reactor in the heating mantle so as to provide a slow rate of cooling. The first crystals of product formed 115 minutes later when the temperature had decreased to 36° C. After standing for an additional 16 hours, the crystalline product was recovered via vacuum filtration on a medium fritted glass funnel. The product recovered on the funnel was pressed into a hard-packed cake and then sequentially rinsed on the filter with two portions (150 milliliters) of 2-propanol. After drying at 35° C. in the vacuum oven, 132.61 grams (68.9% isolated yield) of 4,4'-bis[(3,5-bis(phenylethynyl)phenyl)glyoxalyl]phenyl ether was recovered as a crystalline light yellow powder. HPLC analysis revealed the presence of the desired product at 100 area %. Neutron activation analysis of an aliquot of the product revealed the presence of 3.5+/−0.3 ppm of Pd.

G. Synthesis of 3,3'-(oxy-di-1,4-phenylene)-4,4'-bis[35-bis(phenylethynyl)phenyl]bis(2,5-diphenylcyclopentadienone) (Formula XII) with Low Palladium Content A portion of the 4,4'-bis[(3,5-bis(phenylethynyl)phenyl)glyoxalyl]phenyl ether (128.29 grams, 0.1555 mole) from F. above, 1,3-diphenylacetone (68.69 grams, 0.3267 mole), 2-propanol (1971 milliliters) and toluene (659 milliters), were added to a five liter three neck round bottom reactor. The reactor was additionally outfitted with a chilled (2° C.) condenser, a thermometer with thermostatically controlled heating mantle, a Claisen adaptor, an addition funnel, a nitrogen sparge tube, and a glass stirring shaft with a teflon blade stirrer which was coupled to a variable speed motor to provide mechanical stirring. The addition funnel was charged under a dry nitrogen atmosphere with 1M tetrabutylammonium hydroxide in methanol (10.4 milliliters) diluted into 2-propanol (204 milliliters). Stirring, sparging with nitrogen (1.0 liter per minute) and heating commenced, and at 76° C. the stirred slurry completely went into solution. Once 82° C. was achieved, a gentle reflux was observed and the sparge tube was removed and replaced with an overhead inlet for the nitrogen. Addition of the solution in the addition funnel to the refluxing stirred solution commenced and was completed over the next 12 minutes, during which time, the yellow solution was transformed to a dark red solution. After an additional minute, the dark red solution became a thin grainy slurry, progressing to a thick grainy slurry after an additional 3 minutes. After an additional 4 minutes, heating ceased, the heating mantle was removed from the reactor and HPLC analysis indicated that full conversion of the 4,4'-bis[(3,5-bis(phenylethynyl)phenyl)glyoxalyl]phenyl ether reactant had been achieved, concurrent with optimum formation of the desired product and minimum coproduct formation. After an additional 11 minutes, additional 2-propanol (1971 milliliters) was added to the reactor and the reaction mixture was cooled to 25° C. using a cooling fan on the reactor exterior. When the stirred slurry reached 25° C., the product was recovered via vacuum filtration through a medium fritted glass funnel. The crystalline product was pressed into a packed cake and then washed on the funnel with additional 2-propanol until the filtrate was clear. After drying in a vacuum oven at 30° C. for 72 hours, 176.77 grams (96.9% isolated yield) of 3,3'-(oxy-di-1,4-phenylene)-4,4'-bis[3,5-bis(phenylethynyl)phenyl]bis(2,5-diphenylcyclopentadienone) was recovered as a purple colored crystalline powder. HPLC analysis demonstrated the presence of 96.3 area % of the desired monomer (Formula XII) with the balance comprising a single minor coproduct. Neutron activation analysis of an aliquot of the product revealed the presence of non-detectable Pd at a +/−0.2 ppm limit of detection.

Example 23

Differential Scanning Calorimetry of Monomer of Formula XII

Differential scanning calorimetry (DSC) was completed using a 2.9 milligram portion of the monomer of Formula XII from Example 22 G. above. A DSC 2910 Modulated DSC (TA Instruments) was employed, using a heating rate of 7° C. per minute from 25° C. to 500° C. under a stream of nitrogen flowing at 45 cubic centimeters per minute. An exothermic transition, attributable to-Diels-Alder reaction of phenylethynyl groups with cyclopentadienone groups, was observed with a maximum at 303.0° C. (178.1 joules per gram). The onset temperature for this sharp exothermic transition was 292.1° C., while the ending temperature was 347.5° C. A second exothermic transition, attributable to reaction of phenylethynyl groups, was observed with a maximum at 424.5° C. (46.2 joules per gram). The onset temperature for this broad flat exothermic transition was 390.1° C., while the ending temperature was 484.8° C. A second scanning using the aforementioned conditions revealed no glass transition temperature or any other transitions. The sample recovered from the DSC analysis was a rigid light amber colored fused transparent solid.

Example 24

Synthesis of a Monomer of Formula XXV

A. Synthesis of 1,3-bis[(4-bromophenyl)acetyl]-5-bromobenzene

Bromobenzene (157.0 grams, 1.0 mole) and 5-bromo-1,3-phenylenediacetyl chloride (17.43 grams, 0.0562 mole, 0.1124-COCl equivalent) were added under a dry nitrogen atmosphere to a predried 500 milliliter glass single neck round bottom reactor containing a predried magnetic stirring bar. While maintaining a dry nitrogen atmosphere, stirring of the reactor contents commenced to provide a cloudy amber colored solution. Aluminum chloride (18.0 grams, 0.1350 mole) was added to the reactor in 0.50 gram aliquots every three minutes. Three minutes after the completion of the aluminum chloride additions (105 minutes total addition time), the resultant dark amber colored solution containing suspended white particulate was sampled for HPLC analysis. The HPLC analysis indicated that full conversion of the 5-bromo-1,3-phenylenediacetyl chloride had occurred to the desired product. After an additional 57 minutes, the reactor was removed from the nitrogen atmosphere and the contents poured into a 4 liter beaker containing approximately 1000 grams of ice, followed by addition of deionized water to provide a total volume of approximately 2 liters. After complete melting of the ice, methylene chloride (1 liter) was added to the product mixture, followed by addition to a separatory funnel with agitation to intermix the aqueous and organic phases. Once the aqueous layer had resolved, it was removed and discarded, followed by the washing of the solution remaining in the separatory funnel with deionized water (500 milliliters). The washed solution was dried over anhydrous sodium sulfate, followed by vacuum filtration through a medium fritted glass funnel. Rotary evaporation of the filtrate provided 30.42 grams of a powder containing 88.7 area % of the desired product. Recrystallization from boiling acetonitrile (200 milliliters used, slowly cooled boiling solution to room temperature followed by cooling to 4° C.) provided 25.03 grams (80.8% isolated yield) of light yellow golden colored 1,3-bis[(4-bromophenyl)acetyl]-5-bromobenzene. HPLC analysis revealed the presence of the desired product at 97.7 area %.

B. Synthesis of 1,3-bis[(4-bromophenyl)glyoxalyl]-5-bromobenzene 1,3-bis[(4-Bromophenyl)acetyl]-5-bromobenzene (35.72 grams, 0.0648 mole) prepared using the method of A. above and dimethylsulfoxide (1 liter) were added to a two liter glass three neck round bottom reactor outfitted with a glass mechanical stirring rod with teflon paddle. The reactor was additionally outfitted with a Claisen adaptor, an addition funnel, a condenser (not chilled) vented into a scrubber system, and a thermometer. Aqueous 48% hydrobromic acid (76.5 grams) was added dropwise over a 27 minute period to the stirred 22° C. slurry in the reactor, inducing an exotherm to 30.5° C. A thermostatically controlled heating mantle was then placed on the reactor and gentle heating commenced over an 87 minute period to 100° C., giving an amber colored solution. (By "gentle heating", it is meant that heating was periodically shut off to observe for exothermicity and to allow equilibration). After 190 minutes at the 100° C. reaction temperature HPLC analysis demonstrated that complete reaction had occurred. The hot product solution was diluted into three 4 liter beakers each containing 2 liters of magnetically stirred deionized water. The resulting stirred product slurry was maintained for the next 16 hours, followed by vacuum filtration through a medium fritted glass funnel. After washing the packed bed of light yellow powder on the filter with deionized water, it was removed and dried in the vacuum oven at 60° C. to provide 36.83 grams (98.1% isolated yield) of 1,3-bis[(4-bromophenyl)glyoxalyl]-5-bromobenzene. HPLC analysis revealed the presence of the desired product at 100.0 area %. EI MS analysis confirmed the structure of the product: The intact molecular ion (cluster around m/z 578) was very weak due to the facile cleavage of internal bonds upon electron ionization. Ion clusters around m/z 395 and m/z 183 clearly reflected the presence of bromine for fragment ions of the formula $C_{15}H_7O_3Br_2$ and of the formula $C_7H_{40}Br$, respectively. These fragments resulted from cleavage in one of the glyoxalyl groups. The ion pair at m/z 155 was from a bromophenyl ion. The molecular isotopic pattern from the EI MS spectrum provided good agreement when compared to a theoretical representation of the expected formula. In order to better observe the intact molecule for molecular ion confirmation, chemical ionization (CI) was performed (using isobutane at the CI reagent gas). In the positive CI mass spectrum the protonated molecular ion cluster was visible around 579 amu and possessed the isotopic pattern expected for the compound containing 3 bromine atoms.

C. Synthesis of 1,3-bis[(4-phenylethynylphenyl)glyoxalyl]-5-phenylethynylbenzene 1,3-bis[(4-Bromophenyl)glyoxalyl]-5-bromobenzene (36.68 grams, 0.0634 mole) from B. above, N,N-dimethylformamide (650 grams) which had been sparged with dry nitrogen, triethylamine (52.5 grams, 0.519 mole) which had been sparged with dry nitrogen, phenylacetylene (3.52 grams, 0.0345 mole), triphenylphosphine (1.26 grams, 0.0048 mole) and palladium (II) acetate (0.174 gram, 0.000775 mole), were added under a dry nitrogen atmosphere in the indicated order to a predried one liter glass three neck round bottom reactor outfitted with a glass mechanical stirring rod with teflon paddle. The reactor was additionally outfitted with a Claisen adaptor, a fan cooled spiral condenser, an addition funnel, and a thermometer with thermostatically controlled heating mantle. Additional phenylacetylene (19.94 grams, 0.1952 mole) was added to the addition funnel. Stirring and heating commenced and after 80 minutes, a temperature of 80° C. was achieved. Dropwise addition of the phenylacetylene to the stirred solution then commenced and was completed after 43 minutes with maintenance of temperature between 79° C. and 81° C. After an additional 17 hours at 80° C., HPLC analysis indicated that full conversion of the 1,3-bis[(4-bromophenyl) glyoxalyl]-5-bromobenzene reactant had been achieved. The resulting product was poured into two 4 liter beakers each containing 2.5 liters of magnetically stirred deionized water. The resulting stirred product slurry was maintained for the next 3 hours, followed by vacuum filtration through a coarse fritted glass, funnel. After washing the packed bed of light yellow powder on the filter with deionized water, it was removed as a damp cake of product (115.9 grams) and magnetically stirred as a slurry for one hour in a beaker containing 1.5 liters of boiling acetone. After cooling to room temperature, the product was recovered via vacuum filtration on a coarse fritted glass funnel and then dried in the vacuum oven at 25° C. to provide 33.52 grams (82.3% isolated yield) of 1,3-bis[(4-phenylethynylphenyl)glyoxalyl]-5-phenylethynylbenzene. HPLC analysis revealed the presence of the desired product at 99.4 area %.

D. Synthesis of 3,3'-(1,3-Phenylene-5-phenylethynyl)-4,4'-bis[(4-phenylethynylphenyl]bis(2,5-diphenylcyclopentadienone) (Formula XXV)

A portion of the 1,3-bis[(4-phenylethynylphenyl)glyoxalyl]-5-phenylethynylbenzene (17.37 grams, 0.0270 mole) from C. above, 1,3-diphenylacetone (12.79 grams, 0.0608 mole), 2-propanol (229 milliliters) and toluene (171 milliters), were added to a one liter three neck round bottom reactor. The reactor was additionally outfitted with a chilled (2° C.) condenser, a thermometer with thermostatically controlled heating mantle, a Claisen adaptor, an addition funnel, a nitrogen sparge tube, and a glass stirring shaft with a teflon blade stirrer which was coupled to a variable speed motor to provide mechanical stirring. The addition funnel was charged under a dry nitrogen atmosphere with 1M tetrabutylammonium hydroxide in methanol (1.78 milliliters) diluted into 2-propanol (7 milliliters). Stirring, sparging with nitrogen (1.0 liter per minute) and heating commenced. Once 80° C. was achieved, a gentle reflux was observed and the sparge tube was removed and replaced with an overhead inlet for the nitrogen. Addition of the solution in the addition funnel to the refluxing stirred slurry commenced and was completed over the next 15 minutes, during which time, the yellow slurry was transformed to a dark red solution. After 35 minutes at the 80° C. temperature, additional catalyst solution prepared under a dry nitrogen atmosphere by diluting 1M tetrabutylammonium hydroxide in methanol (0.45 milliliter) into 2-propanol (1.8 milliliters), was injected into the solution. After an additional 30 minutes at the 80° C. temperature, the dark red solution became a thick, grainy slurry and a sample was removed for HPLC analysis. After an additional 18 minutes, heating ceased, the heating mantle was removed from the reactor, as the HPLC analysis indicated that full conversion of the 1,3-bis[(4-phenylethynylphenyl)glyoxalyl]-5-phenylethynylbenzene reactant had been achieved, concurrent with optimum formation of the desired product and minimum coproduct formation. Additional 2-propanol (229 milliliters) was added to the reactor and the reaction mixture was cooled to 25° C. using a cooling fan on the reactor exterior. When the stirred slurry reached 25° C., the product was recovered via vacuum filtration through a coarse fritted glass funnel. The crystalline product was pressed into a cake and then washed on the funnel with additional 2-propanol until the filtrate was clear. The product recovered on the funnel was recovered and loaded into a clean reactor containing fresh 2-propanol (500 milliliters), then rapidly stirred for 30 minutes, followed by recovery on the coarse fritted glass funnel and washing with additional 2-propanol to provide a clear filtrate. After drying in a vacuum oven at 25° C. for 3 days, 24.28 grams (90.6% isolated yield) of 3,3'-(1,3-phenylene-5-phenylethynyl)-4,4'-bis[(4-phenylethynylphenyl]bis(2,5-diphenylcyclopentadienone) was recovered as a purple red colored crystalline powder. HPLC analysis demonstrated the presence of 98.0 area % of the desired monomer (Formula XXV) with the balance comprising two single minor coproducts (0.6 and 1.4 area %, respectively).

Example 25

Differential Scanning Calorimetry of Monomer of Formula XXV

Differential scanning calorimetry (DSC) was completed using a 2.5 milligram portion of the monomer of Formula XXV from Example 24 D. above. A DSC 2910 Modulated DSC (TA Instruments) was employed, using a heating rate of 7° C. per minute from 25° C. to 500° C. under a stream of nitrogen flowing at 45 cubic centimeters per minute. An exothermic transition, attributable to Diels-Alder reaction of phenylethynyl groups with cyclopentadienone groups, was observed with a maximum at 242.7° C. (120.3 joules per gram). The onset temperature for this sharp exothermic transition was 239° C., while the ending temperature was 322.5° C. The onset temperature was somewhat merged with a slight (approximate enthalpy=3 joules per gram) endothermic melting transition which possessed a minimum at 237.7° C. A second exothermic transition, attributable to reaction of phenylethynyl groups, was observed with a maximum at 453.7° C. (42.8 joules per gram). The onset temperature for this broad flat exothermic transition was 375.6° C., while the ending temperature was 497.7° C. A second scanning using the aforementioned conditions revealed no glass transition temperature or any other transitions. The sample recovered from the DSC analysis was a rigid light amber colored fused transparent solid.

Example 26

Synthesis of 3,3'-(oxy-di-1,4-phenylene)-4,4'-bis[3,5-bis(phenylethynyl)phenyl]bis[2,5-di-(4-phenylethynyl)phenylcyclopentadienone] with Low Palladium Content (Monomer XXVII)

4,4'-bis[(3,5-bis(Phenylethynyl)phenyl)glyoxalyl]phenyl ether (8.25 grams, 0.01 mole, contained 2+/−1 ppm Pd) synthesized using the method of Example 22 F., 1,3-bis(4-phenylethynylphenyl)-2-propanone (8.62 grams, 0.021 mole, contained 2+/−1 ppm Pd) synthesized using the method of Example 4 B. with the addition of treatment with sodium diethyldithiocarbamate trihydrate in the manner shown in Example 22 F., 2-propanol (191 milliliters) and toluene (63 milliters), were added to a one liter three neck round bottom reactor. The reactor was additionally outfitted with a chilled (2° C.) condenser, a thermometer with thermostatically controlled heating mantle, a Claisen adaptor, an addition funnel, a nitrogen sparge tube, and a glass stirring shaft with a teflon blade stirrer which was coupled to a variable speed motor to provide mechanical stirring. The addition funnel was charged under a dry nitrogen atmosphere with 1M tetrabutylammonium hydroxide in methanol (0.67 milliliter) diluted into 2-propanol (13 milliliters). Stirring, sparging with nitrogen (1.0 liter per minute) and heating commenced, and at 78° C. the stirred slurry completely went into solution. Additionally, at this temperature, a gentle reflux was observed and the sparge tube was removed and replaced with an overhead inlet for the nitrogen. Addition of the solution in the addition funnel to the refluxing stirred solution commenced and was completed over the next 13 minutes, during which time, the yellow solution was transformed to a dark red amber solution. After an additional 9 minutes, the dark red amber solution became a thin grainy slurry, progressing to a thick grainy slurry after an additional 15 minutes. After 3 more minutes, with the temperature now at 77° C., additional catalyst solution prepared under a dry nitrogen atmosphere by diluting 1M tetrabutylammonium hydroxide in methanol (0.34 milliliter) into 2-propanol (7 milliliters), was injected into the solution. After an additional 15 minutes, heating ceased, the heating mantle was removed from the reactor and HPLC analysis indicated that full conversion of the 4,4'-bis[(3,5-bis(phenylethynyl)phenyl)glyoxalyl]phenyl ether reactant had been achieved, concurrent with optimum formation of the desired product and minimum coproduct formation. Additional 2-propanol (400 milliliters) was added at this time to the reactor causing the reaction mixture to cool to 50° C. within 3 minutes. Product was recovered from the stirred 50° C. slurry via vacuum filtration through a medium fritted glass funnel. The crystalline product was pressed into a packed cake and then washed on the funnel with additional 2-propanol until the filtrate was clear. After air drying on the filter, 32.2 grams of damp product cake was recovered and added to a beaker containing tetrahydrofuran (300 milliliters, inhibited with butylated hydroxytoluene) and magnetically stirred to provide a solution. The resulting solution was added to an addition funnel, from which dropwise addition into a beaker containing magnetically stirred 2-propanol (1.2 liters) commenced. Product was recovered from the stirred slurry via vacuum filtration through a medium fritted glass funnel, then the packed cake was washed on the funnel with additional 2-propanol until the filtrate was clear. After drying in the vacuum oven at 30° C. for 72 hours, 14.79 grams (94.0% isolated yield) of 3,3'-(oxy-di-1,4-phenylene)-4,4'-bis[3,5-bis(phenylethynyl)phenyl]-bis[2,5-di-(4-phenylethynyl)phenylcyclopentadienone] was recovered as a dark purple red colored crystalline powder. HPLC analysis demonstrated the presence of 95.1 area % of the desired 3,3'-(oxy-di-1,4-phenylene)-4,4'-bis[3,5-bis(phenylethynyl)phenyl]-bis[2,5-di-(4-phenylethynyl)phenylcyclopentadienone] monomer with the balance comprising four minor coproducts.

Example 27

Differential Scanning Calorimetry of 3,3'-(oxy-di-1,4-phenylene)-4,4'-bis [3,5-bis(phenylethynyl)phenyl]-bis [2,5-di-(4-phenylethynyl)phenylcyclopentadienone]

Differential scanning calorimetry (DSC) was completed using a 3.8 milligram portion of the monomer of 3,3'-(oxy-di-1,4-phenylene)-4,4'-bis[3,5-bis(phenylethynyl)phenyl]-bis[2,5-di-(4-phenylethynyl)phenylcyclopentadienone] from Example 26 above. A DSC 2910 Modulated DSC (TA Instruments) was employed, using a heating rate of 7° C. per minute from 25° C. to 500° C. under a stream of nitrogen flowing at 45 cubic centimeters per minute. An exothermic transition, attributable to Diels-Alder reaction of phenylethynyl groups with cyclopentadienone groups, was observed with a maximum at 212.5° C. (81.5 joules per gram). The onset temperature for this exothermic transition was 193.5° C., while the ending temperature was 290.6° C. The onset temperature for this exothermic transition was merged with a slight (approximate enthalpy=2 joules per gram) endothermic melting transition, which possessed a minimum at 193.5° C. A second exothermic transition, attributable to reaction of phenylethynyl groups, was observed with a maximum at 395.9° C. (149.1 joules per gram). The onset temperature for this exothermic transition was 323.2° C., while the ending temperature was 493.9° C. A second scanning using the aforementioned conditions revealed no glass transition temperature or any other transitions. The sample recovered from the DSC analysis was a rigid dark amber colored fused grainy solid.

Example 28

Synthesis of 3,3'-(1,3-phenylene-5-phenylethynyl)-4,4'-bis [(4-phenylethynylphenyl]bis[2,5-di-(4-phenylethynyl)phenylcyclopentadienone] with Low Palladium Content 1,3-bis[(4-Phenylethynylphenyl)glyoxalyl]-5-phenylethynylbenzene (9.64 grams, 0.015 mole, contained 11+/−1 ppm Pd) synthesized using the method of Example 24 C. with the addition of treatment with sodium diethyldithiocarbamate trihydrate in the manner shown in Example 22 F., 1,3-bis(4-phenylethynylphenyl)-2-propanone (12.56 grams, 0.0306 mole, contained 2+/−1 ppm Pd) synthesized using the method of Example 4 B. with the addition of treatment with sodium diethyldithiocarbamate trihydrate in the manner shown in Example 22 F., 2-propanol (177 milliliters) and toluene (135 milliters), were added to a one liter three neck round bottom reactor. The reactor was additionally outfitted with a chilled (2° C.) condenser, a thermometer with thermostatically controlled heating mantle, a Claisen adaptor, an addition funnel, a nitrogen sparge tube, and a glass stirring shaft with a teflon blade stirrer which was coupled to a variable speed motor to provide mechanical stirring. The addition funnel was charged under a dry nitrogen atmosphere with 1 M tetrabutylammonium hydroxide in methanol (0.99 milliliter) diluted into 2-propanol (20 milliliters). Stirring, sparging with nitrogen (1.0 liter per minute) and heating commenced, and at 78° C. the product was a stirred slurry under gentle reflux. At this temperature, the sparge tube was removed and replaced with an overhead inlet for the nitrogen. Dropwise addition of the solution in the addition funnel to the refluxing stirred slurry commenced and was completed over a period of 7 minutes, during which time, the yellow slurry was transformed to a dark amber solution. After an additional 80 minutes, heating ceased, the heating mantle was removed from the reactor and HPLC analysis indicated that full conversion of the 1,3-bis [(4-phenylethynylphenyl)glyoxalyl]-5-phenylethynylbenzene reactant had been achieved, concurrent with optimum formation of the desired product and minimum coproduct formation. Additional 2-propanol (400 milliliters) was added at this time to the reactor causing the reaction mixture to cool to 50° C. within 4 minutes. Product was recovered from the stirred 50° C. slurry via vacuum filtration through a medium fritted glass funnel. The crystalline product was pressed into a packed cake and then washed on the funnel with additional 2-propanol until the filtrate was clear. After air drying on the filter, 23.4 grams of damp product cake was recovered and added to a beaker containing tetrahydrofuran (450 milliliters, inhibited with butylated hydroxytoluene) and magnetically stirred to provide a solution. The resulting solution was added to an addition funnel, from which dropwise addition into a beaker containing magnetically stirred 2-propanol (2.4 liters)

commenced. Product was recovered from the stirred slurry via vacuum filtration through a medium fritted glass funnel, then the packed cake was washed on the funnel with additional 2-propanol until the filtrate was clear. After drying in the vacuum oven at 30° C. for 72 hours, 17.95 grams (86.0.% isolated yield) of 3,3'-(1,3-phenylene-5-phenylethynyl)-4,4'-bis[(4-phenylethynylphenyl]bis[2,5-di-(4-phenylethynyl) phenylcyclopentadienone] was recovered as a medium purple colored crystalline powder. HPLC analysis demonstrated the presence of 97.1 area % of the desired 3,3'-(1,3-phenylene-5-phenylethynyl)-4,4'-bis[(4-phenylethynylphenyl]bis[2,5-di-(4-phenylethynyl)phenylcyclopentadienone] monomer with the balance comprising two minor coproducts.

Example 29

Differential Scanning Calorimetry of 3,3'-(1,3-phenylene-5-phenylethynyl)-4,4'-bis [(4-phenylethynylphenyl]bis [2,5-di-(4-phenylethynyl)phenylcyclopentadienone]

Differential scanning calorimetry (DSC) was completed using a 2.9 milligram portion of the monomer of 3,3'-(oxy-di-1,4-phenylene)-4,4'-bis[3,5-bis(phenylethynyl)phenyl]-bis[2,5-di-(4-phenylethynyl)phenylcyclopentadienone] from Example 28 above. A DSC 2910 Modulated DSC (TA Instruments) was employed, using a heating rate of 7° C. per minute from 25° C. to 500° C. under a stream of nitrogen flowing at 45 cubic centimeters per minute. An exothermic transition, attributable to Diels-Alder reaction of phenylethynyl groups with cyclopentadienone groups, was observed with a maximum at 215.5° C. (54.6 joules per gram). The onset temperature for this exothermic transition was 179.9° C., while the ending temperature was 284.5° C. A second exothermic transition, attributable to reaction of phenylethynyl groups, was observed with a maximum at 397.4° C. (138.2 joules per gram). The onset temperature for this exothermic transition was 308.8° C., while the ending temperature was 492.4° C. A second scanning using the aforementioned conditions revealed no glass transition temperature or any other transitions. The sample recovered from the DSC analysis was a yellow brown colored grainy solid.

Example 30

A. Synthesis of 4,4'-bis(phenoxy)benzil

Anhydrous 1,2-dichloroethane (100 milliliters), aluminum chloride (27.20 grams, 0.204 mole) and then diphenyl ether (255.3 grams, 1.5 moles) were added under a dry nitrogen atmosphere to a predried 500 milliliter glass single neck round bottom Schlenk reactor containing a predried magnetic stirring bar. After sealing under dry nitrogen, the reactor was placed on a Schlenk line under slightly positive nitrogen pressure. Stirring of the reactor contents commenced to provide a slurry. An ice bath was placed under the reactor 15 minutes before starting the reaction. Oxalyl chloride (12.7 grams, 0.10 mole) was added under a dry nitrogen atmosphere to a predried glass addition funnel. The addition funnel was outfitted with a Schlenk adaptor, then sealed under dry nitrogen and placed on the Schlenk line. The reactor and addition funnel were coupled under dynamic nitrogen flow. The oxalyl chloride was added dropwise to the stirred reactor over a 45 minute period. After 90 minutes of post reaction, the reactor was removed from the Schlenk line and the contents poured into a 4 liter beaker which was half-filled with ice. Dichloromethane (400 milliliters) was used to rinse the residual reaction product from the reactor into the beaker of ice. Once the ice had melted, the contents of the beaker were added to a separatory funnel and the aqueous layer removed and discarded. The organic layer remaining in the separatory funnel was washed with deionized water (200 milliliters), then the recovered organic layer was dried over anhydrous sodium sulfate, followed by vacuum filtration through a medium fritted glass funnel. Rotary evaporation of the filtrate provided an oil product (261.4 grams) which was added to a beaker containing magnetically stirred hexanes (700 milliliters). The resulting slurry was filtered through a medium fritted glass funnel followed by washing of the white powder on the funnel with sufficient hexanes to cover. Drying in the vacuum oven at 80° C. provided 33.24 grams (84.3% isolated yield) of 4,4'-bis(phenoxy)benzil. HPLC analysis revealed the presence of the desired product at 100 area

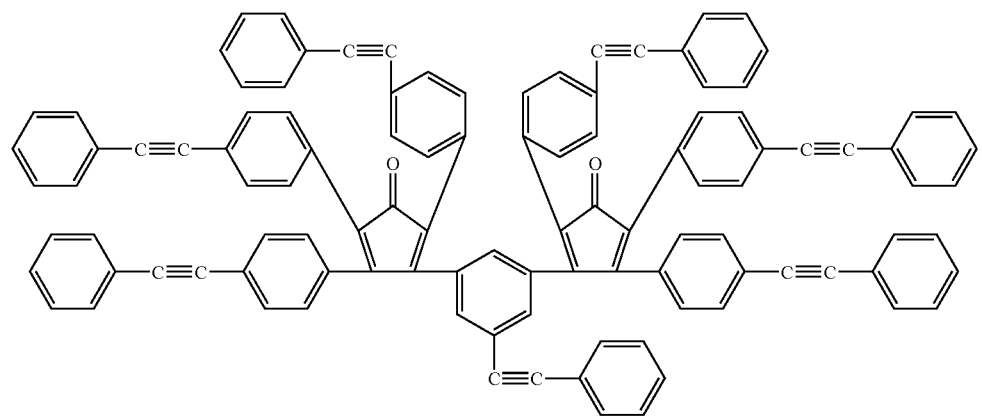

B. Synthesis of 4,4'-bis[(3,5-dibromophenyl)acetylphenoxy] benzil

Anhydrous 1,2-dichloroethane (50 milliliters) and aluminum chloride (2.93 grams, 0.022 mole) were added under a dry nitrogen atmosphere to a predried 500 milliliter glass single neck round bottom Schlenk reactor containing a predried magnetic stirring bar. After sealing under dry nitrogen, the reactor was placed on a Schlenk line under slightly positive nitrogen pressure. Stirring of the reactor contents commenced to provide a slurry. An ice bath was placed under the reactor 20 minutes before starting the reaction. 4,4'-bis(Phenoxy)benzil (1.97 grams, 0.005 mole) from A. above and 3,5-dibromophenylacetyl chloride (3.12 grams, 0.01 mole) prepared using the method of Example 22 B. were dissolved in anhydrous 1,2-dichloroethane (100 millliliters) and the resultant solution added under a dry nitrogen atmosphere to a predried glass addition funnel. The addition funnel was outfitted with a Schlenk adaptor, then sealed under dry nitrogen and placed on the Schlenk line. The reactor and addition funnel were coupled under dynamic nitrogen flow. The solution in the addition funnel was added dropwise to the stirred reactor over a 145 minute period. After an additional 40 minutes, the ice bath was removed from the reactor. After another 24 hours, the reactor was removed from the Schlenk line and the contents poured into a 4 liter beaker containing 1.5 liters of magnetically stirred deionized water, followed by the addition of dichloromethane (1 liter). The contents of the beaker were added to a separatory funnel and the aqueous layer removed and discarded. The organic layer remaining in the separatory funnel was washed with deionized water (150 milliliters), then the recovered organic layer was dried over anhydrous sodium sulfate, followed by vacuum filtration through a medium fritted glass funnel. Rotary evaporation of the filtrate provided an off-white solid (4.98 grams) which was added to a beaker along with acetonitrile (400 milliliters) and then brought to a boil and allowed to cool to room temperature to provide a crystalline product. The crystalline product was recovered via vacuum filtration, the dried in the vacuum oven at 80° C. to provided 3.23 grams (68.3% isolated yield) of 4,4'-bis[(3,5-dibromophenyl)acetylphenoxy] benzil. HPLC analysis revealed the presence of the desired product at 97.9 area %. A second crop of crystalline product (1.0 gram after drying) was recovered by rotary evaporation of the filtrate to half of original volume and holding at 4° C. HPLC analysis of this second crop product revealed the presence of 94.2 area % of the desired product. EI MS analysis using a direct insertion probe confirmed the structure of the product: The intact molecular ion was not observed due to the facile cleavage of internal bonds upon electron ionization. The ion cluster centered at m/z 473 clearly reflected the isotopic pattern of 2 bromine atoms for a fragment ion of the formula $C_{21}H_{13}O_3Br_2$. This fragment resulted from cleavage in the central glyoxalyl group, representing exactly half of the molecular structure. Ions at m/z 197 arose from the center of the molecule. In order to observe the intact molecule for molecular ion confirmation, chemical ionization (CI) was performed (using isobutane at the CI reagent gas). The sample was introduced employing a direct exposure probe. The sample coated on the probe wire was ballistically heated from ambient temperature to about 500° C. in less than one second. In the positive CI mass spectrum the intense protonated molecular ion cluster was visible around 946 amu and possessed the isotopic pattern expected for the compound containing 4 bromine atoms. The ion cluster centered at m/z 473 was again noted in the CI mass spectrum. The structure for the 4,4'-bis[(3,5-dibromophenyl)acetylphenoxy]benzil product is given below:

C. Synthesis of 4,4'-bis[(3,5-dibromophenyl)glyoxalylphenoxy]benzil 4,4'-bis[(3,5-Dibromophenyl)acetylphenoxy]benzil (6.0 grams, 0.0063 mole) from B. above and dimethylsulfoxide (400 milliliters) were added to a one liter glass three neck round bottom reactor outfitted with a glass mechanical stirring rod with teflon paddle. The reactor was additionally outfitted with a Claisen adaptor, an addition funnel, a condenser (not chilled) vented into a scrubber system, and a thermometer. Aqueous 48% hydrobromic acid (7.5 grams) was added dropwise over a one minute period to the stirred 23° C. hazy solution in the reactor, inducing an exotherm to 28° C. A thermostatically controlled heating mantle was then placed on the reactor and gentle heating-commenced over a 48 minute period to 100° C., giving a light yellow colored solution. (By "gentle heating", it is meant that heating was periodically shut off to observe for exothermicity and to allow equilibration). After 2 hours at the 100° C. reaction temperature HPLC analysis demonstrated that complete reaction had occurred. The hot product solution was diluted, after an additional 35 minutes at 100° C., into a 4 liter beaker containing 3.0 liters of magnetically stirred deionized water. The resulting stirred product slurry was maintained for the next 16 hours, followed by vacuum filtration through a medium fritted glass funnel. After washing the packed bed of powder on the filter with deionized water, it was removed and added to a beaker along with acetonitrile (250 milliliters) and then brought to a boil and allowed to cool to room temperature and filtered. After drying the product on the filter from the acetonitrile extraction in the vacuum oven at 60° C., 6.2 grams (100% isolated yield) of 4,4'-bis[(3,5-dibromophenyl)glyoxalylphenoxy]benzil was recovered as a light yellow colored powder. HPLC analysis revealed the presence of the desired product at 98.5 area %, with the balance comprising a single minor coproduct.

D. Synthesis of 4,4'-bis[(3,5-bis(phenyethynyl)phenyl)glyoxalylphenoxy]benzil 4,4'-bis[(3,5-Dibromophenyl)glyoxalylphenoxy]benzil (4.17 grams, 0.0043 mole) from C. above, N,N-dimethylformamide (125 grams) which had been sparged with dry nitrogen, triethylamine (4.73 grams, 0.0467 mole) which had been sparged with dry nitrogen, phenylacetylene (2.11 grams, 0.0207 mole), triphenylphosphine (0.114 gram, 0.0004 mole) and palladium (II) acetate (0.016 gram, 0.00007 mole) were added under a dry nitrogen atmosphere in the indicated order to a predried 250 mililiter glass three neck round bottom reactor containing a magnetic stir bar. The reactor was additionally outfitted with a fan cooled spiral condenser and a thermometer with thermostatically controlled heating mantle. Stirring and heating commenced and after 48 minutes, a temperature of 80° C. was achieved. After 17 hours at 80° C., HPLC analysis indicated that full conversion of the 4,4'-bis[(3,5-dibromophenyl)glyoxalylphenoxy]benzil reactant had been achieved. After an additional 3.5 hours at 80° C., the product was poured into a 4 liter beaker containing 3 liters of magnetically stirred deionized water. The resulting stirred product slurry was maintained for the next 20 hours, followed by vacuum filtration through a medium fitted glass funnel. After washing the packed bed of product on the filter with deionized water, it was dried in the vacuum oven for 4 hours at 60° C. to provide 4.85 grams of light golden yellow colored powder. HPLC analysis revealed the presence of the desired tetraphenylethynyl product at 96.3 area % with the balance comprising a single coproduct. Further purification was completed by dissolving the product into a boiling solution of magnetically stirred ethanol (350 milliliters) and acetone (350 milliliters) followed by addition of sufficient deionized water to induce haziness. The slight amount of tarry material that precipitated from this solution as it cooled was removed via decantation and discarded. Rotary evaporation of the solution provided 3.35 grams of product, which was further purified via chromatography on neutral silica gel using chloroform as the eluent. After rotary evaporation of the effluent from the chromatographic purification, 3.24 grams of 4,4'-bis[(3,5-bis(phenylethynyl)phenyl)glyoxalylphenoxy]benzil was recovered as a crystalline light yellow powder. HPLC analysis revealed the presence of the desired product at 98.4 area %.

E. Synthesis of the tetraphenylethynyltris(cyclopentadienone) Monomer

A portion of the 4,4,-bis[(3,5-bis(phenylethynyl)phenyl)glyoxalylphenoxy]benzil (3.22 grams, 0.00304 mole) from D. above, 1,3-diphenylacetone (2.01 grams, 0.0096 mole), 2-propanol (100 milliliters) and toluene (33 milliters), were added to a 500 milliliter three neck round bottom reactor. The reactor was additionally outfitted with a chilled (2° C.) condenser, a thermometer with thermostatically controlled heating mantle, a Claisen adaptor, an addition funnel, a nitrogen sparge tube, and a glass stirring shaft with a teflon blade stirrer which was coupled to a variable speed motor to provide mechanical stirring. The addition funnel was charged under a dry nitrogen atmosphere with 1 M tetrabutylammonium hydroxide in methanol (0.39 milliliter) diluted into 2-propanol (6 milliliters). Stirring, sparging with nitrogen (1.0 liter per minute) and heating commenced, and at 72° C. the stirred slurry completely went into solution. Once 79° C. was achieved, a gentle reflux was observed and the sparge tube was removed and replaced with an overhead inlet for the nitrogen. Addition of the solution in the addition funnel to the refluxing stirred solution commenced and was completed over the next 6 minutes, during which time, the yellow solution was transformed to a dark red amber solution. After an additional 103 more minutes of reaction at 79-80° C., additional catalyst solution prepared under a dry nitrogen atmosphere by diluting 1M tetrabutylammonium hydroxide in methanol (0.195 milliliter) into 2-propanol (0.5 milliliter), was injected into the solution. After an additional 31 minutes, the dark red solution became a thin grainy slurry. Two additional injections of catalyst solution (0.1 milliliter 1 M tetrabutylammonium hydroxide in 0.3 milliliter 2-propanol and 0.2 milliliter 1M tetrabutylammonium hydroxide in 0.5 milliliter 2-propanol, respectively) were made after an additional 65 and 41 minutes of reaction, respectively. After an additional 37 minutes, heating ceased, the heating mantle was removed from the reactor and HPLC analysis indicated that full conversion of the 4,4'-bis[(3,5-bis(phenylethynyl)phenyl)glyoxalylphenoxy]benzil reactant had been achieved, concurrent with formation of the desired product. At this time, additional 2-propanol (150 milliliters) was added to the reactor and the reaction mixture was cooled to 30° C. using a cooling fan on the reactor exterior. When the stirred slurry reached 30° C., the product was recovered via vacuum filtration through a medium fritted glass funnel. The product was pressed into a packed cake and then washed on the funnel with additional 2-propanol until the filtrate was clear. After drying in a vacuum oven at 30° C. for 72 hours, 3.80 grams of the tetraphenylethynyltris(cyclopentadienone) monomer (structural formula given below) was recovered as a medium purple colored powder. HPLC analysis demonstrated the presence of 72.5 area % of the desired monomer with the balance comprising a single coproduct present at 24.3 area % and a minor coproduct present at 3.2 area %.

Further purification was completed by dissolving the product into a minimum of dichloromethane followed by chromatography on neutral silica gel using dichloromethane as the eluent. After rotary evaporation of the various aliquots of effluent from the chromatographic purification, followed by HPLC analysis to determine purity, 0.74 gram containing 94.3 area % of the desired product was recovered, along with 1.16 grams containing 92.2 area % of the desired product.

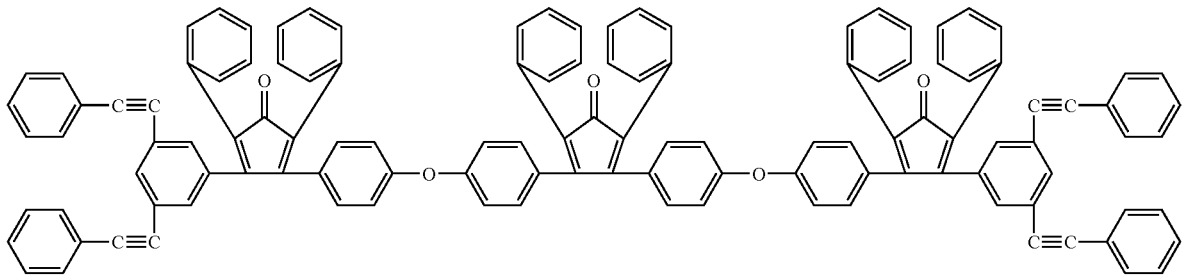

Example 31

Differential Scanning Calorimetry OF tetraphenylethynyltris(cyclopentadienone) Monomer Differential scanning calorimetry (DSC) was completed using a 3.9 milligram portion of the monomer from the 1.16 grams of chromatographically purified tetraphenylethynyltris(cyclopentadienone) monomer of Example 30 E. above. A DSC 2910 Modulated DSC (TA Instruments) was employed, using a heating rate of 7° C. per minute from 25° C. to 500° C. under a stream of nitrogen flowing at 45 cubic centimeters per minute. An exothermic transition, attributable to Diels-Alder reaction of phenylethynyl groups with cyclopentadienone groups, was observed with a maximum at 221.2° C. (160.6 joules per gram). The onset temperature for this sharp exothermic transition was 162.4° C., while the ending temperature was 346.7° C. The onset temperature for this exothermic transition was merged with a slight endothermic melting transition, which possessed a minimum at 162.4° C. A second exothermic transition, attributable to reaction of phenylethynyl groups, was observed with a maximum at 445.8° C. (6.2 joules per gram). The onset temperature for this exothermic transition was 411.2° C., while the ending temperature was 467.3° C. A second scanning using the aforementioned conditions revealed no glass transition temperature or any other transitions. The sample recovered from the DSC analysis was a rigid dark amber colored fused solid.

Example 32

Preparation of Porous Matrix from Monomer of Formula IV and a Cross-Linked Polystyrene Porogen 30% 7.2 nm Cross-Linked Polystyrene Porogen To a 25 milliter round bottom flask was added 2.0 grams of monomer of Formula IV, 0.86 grams of crosslinked polystyrene nanoparticles (average peak particle size of 7.2 nm as measured by size exclusion chromatography employing a laser light scattering detector, made from microemulsion polymerization) and 4.7 grams of γ-butyrolactone (GBL). The resulting mixture was purged under nitrogen for 15 minutes and then heated to 200° C. with an oil bath under nitrogen for 2.5 hours. The mixture was then cooled to 145° C. and diluted with an equal amount of cyclohexanone. The mixture was further cooled to room temperature to give a 17.5% polymer mixture in GBL/cyclohexanone.

The mixture was applied to a silicon wafer and cast by spin-coating to form a ~1.0 micron thick film. The film was baked on an MTI hotplate at 150° C. for 2 minutes, and the coated wafer was transferred to a vacuum oven. The oven temperature was ramped at 7° C./minute to 400° C. under nitrogen, then held for 120 minutes to allow the decomposition of polystyrene porogen before cooling. An estimate of the average spherical pore size based on small angle X-ray scattering (SAXS) measurement of the film was about 6.5 nm in diameter. The refractive index of the resulting film was 1.506.

Example 33

Preparation of Porous Matrix from Monomer of Formula XII and a Cross-Linked Polystyrene Porogen 30% 7.2 nm Cross-Linked Polystyrene Porogen To a 25 milliter round bottom flask was added 2.0 grams of monomer of Formula XII, 0.86 grams of crosslinked polystyrene nanoparticles (average peak particle size of 7.2 nm as measured by size exclusion chromatography employing a laser light scattering detector, made from microemulsion polymerization) and 4.7 grams of γ-butyrolactone (GBL). The resulting mixture was purged under nitrogen for 15 minutes and then heated to 200° C. with an oil bath under nitrogen for 2.5 hours. The mixture was then cooled to 145° C. and diluted with an equal amount of cyclohexanone. The mixture was further cooled to room temperature to give a 17.5% polymer mixture in GBL/cyclohexanone.

The mixture was applied to a silicon wafer and cast by spin-coating to form a ~1.0 micron thick film. The film was baked on an MTI hotplate at 150° C. for 2 minutes, and the coated wafer was transferred to a vacuum oven. The oven temperature was ramped at 7° C./minute to 400° C. under nitrogen, then held for 120 minutes to allow the decomposition of polystyrene porogen before cooling. An estimate of the average spherical pore size based on small angle X-ray scattering (SAXS) measurement of the film was about 6.9 nm in diameter. The refractive index of the resulting film was 1.514.

Example 34

Preparation of Porous Matrix From Monomer of Formula V and a Cross-Linked Polystyrene Porogen 30% 7.2 nm Cross-Linked Polystyrene Porogen To a 25 milliter round bottom flask was added 2.0 grams of monomer of Formula V, 0.86 grams of crosslinked polystyrene nanoparticles (average peak particle size of 7.2 nm as measured by size exclusion chromatography employing a laser light scattering detector, made from microemulsion polymerization) and 4.7 grams of γ-butyrolactone (GBL). The resulting mixture was purged under nitrogen for 15 minutes and then heated to 180° C. with an oil bath under nitrogen for 4.0 hours. The mixture was then cooled to 145° C. and diluted with an equal amount of cyclohexanone. The mixture was further cooled to room temperature to give a 17.5% polymer mixture in GBL/cyclohexanone. The mixture was applied to a silicon wafer and cast by spin-coating to form a ~1.0 micron thick film. The film was baked on an MTI hotplate at 150° C. for 2 minutes, and the coated wafer was transferred to a vacuum oven. The oven temperature was ramped at 7° C./minute to 400° C. under nitrogen, then held for 120 minutes to allow the decomposition of polystyrene porogen before cooling. The refractive index of the resulting film was 1.539.

Example 35

Preparation of Porous Matrix from Monomer of Formula XXV and a Cross-Linked Polystyrene Porogen 30% 7.2 nm Cross-Linked Polystyrene Porogen To a 25 milliter round bottom flask was added 2.0 grams of monomer of Formula XXV, 0.86 grams of crosslinked polystyrene nanoparticles (average peak particle size of 7.2 nm as measured by size exclusion chromatography employing a laser light scattering detector, made from microemulsion polymerization) and 4.7 grams of γ-butyrolactone (GBL). The resulting mixture was purged under nitrogen for 15 minutes and then heated to 200° C. with an oil bath under nitrogen for 5.0 hours. The mixture was then cooled to 145° C. and diluted with an equal amount of cyclohexanone. The mixture was further cooled to room temperature to give a 17.5% polymer mixture in GBL/cyclohexanone.

The mixture was applied to a silicon wafer and cast by spin-coating to form a ~1.0 micron thick film. The film was baked on an MTI hotplate at 150° C. for 2 minutes, and the coated wafer was transferred to a vacuum oven. The oven temperature was ramped at 7° C./minute to 400° C. under nitrogen, then held for 120 minutes to allow the decomposition of polystyrene porogen before cooling. An estimate of the average spherical pore size based on small angle X-ray scattering (SAXS) measurement of the film was about 6.1 nm in diameter. The refractive index of the resulting film was 1.510.

Example 36

Preparation of Porous Matrix from Monomer of Formula XXVI Cross-Linked Polystyrene Porogen 30% 7.2 nm Cross-Linked Polystyrene Porogen To a 25 milliter round bottom flask was added 2.0 grams of monomer of Formula XXVI 6 grams of crosslinked polystyrene nanoparticles (average peak particle size of 7.2 nm as measured by size exclusion chromatography employing a laser light scattering detector, made from microemulsion polymerization) and 11.4 grams of mesitylene. The resulting mixture was purged under nitrogen for 15 minutes and then heated to 160° C. with an oil bath under nitrogen for 12 hours. The mixture was further cooled to room temperature to give the final formulation with 20% of solid content. The mixture was applied to a silicon wafer and cast by spin-coating to form a ~1.0 micron thick film. The film was baked on an MTI hotplate at 150° C. for 2 minutes, and the coated wafer was transferred to a vacuum oven. The oven temperature was ramped at 7° C./minute to 400° C. under nitrogen, then held for 120 minutes to allow the decomposition of polystyrene porogen before cooling. The refractive index of the resulting film was 1.506.

Example 37

Preparation of Porous Matrix from Monomer of Formula IV and a Cross-Linked Polystyrene Porogen 30% 5.8 nm Cross-Linked Polystyrene Porogen To a 25 milliter round bottom flask was added 3.0 grams of monomer of Formula IV, and 7.0 grams of γ-butyrolactone (GBL). The resulting mixture was purged under nitrogen for 15 minutes and then heated to 200° C. with an oil bath under nitrogen for 1.0 hour to make an oligomer solution with a Mn of 34,000 and Mw of 72,000 g/mole relative to polystyrene standard. The mixture was then cooled to 145° C. and diluted with 5.0 grams of cyclohexanone to make a solution with 20% of solid content. 10 grams of above solution was then mixed with 0.86 grams of crosslinked polystyrene nanoparticles (average peak particle size of 5.8 nm as measured by size exclusion chromatography employing a laser light scattering detector, made from microemulsion polymerization). The mixture was further purged with 15 minutes and then heated to 100° C. for 50 minutes, diluted with 3.0 grams of cyclohexanone to make the final formulation. The above mixture was applied to a silicon wafer and cast by spin-coating to form a ~1.0 micron thick film. The film was baked on an MTI hotplate at 150° C. for 2 minutes, and the coated wafer was transferred to a vacuum oven. The oven temperature was ramped at 7° C./minute to 400° C. under nitrogen, then held for 120 minutes to allow the decomposition of polystyrene porogen before cooling. An estimate of the average spherical pore size based on small angle X-ray scattering (SAXS) measurement of the film was about 5.0 nm in diameter. The refractive index of the resulting film was 1.545.

Example 38

Synthesis of Monomer of Formula V 4,4'-Bis[(4-phenylethynylphenyl)glyoxalyl]phenyl ether (1.59 grams, 0.0025 mole) from B of example 2 and 2.26 grams (0.0055 mole) of 1,3-bis(4-phenylethynylphenyl)-2-propanone from B of example 4 were added to a reactor containing 30 ml of anhydrous toluene/2-propanol (1:1) mixture. Stirring and heating commenced, and once the mixture reached 80° C., tetrabutylammonium hydroxide (1M in methanol, 0.25 ml) was mixed with 8.0 ml of 2-propanol and added dropwise for about 10-15 minutes, immediately inducing a deep red purple color. After maintaining at 80° C. for 1 hour, HPLC analysis indicated that full conversion of the 4,4'-Bis[(4-phenylethynylphenyl)glyoxalyl]phenyl ether reactant had been achieved. At this time, the oil bath was removed from the reactor, and the reaction mixture was allowed to cool to room temperature. The product was recovered via filtration through a medium fritted glass funnel. The crystalline product on the funnel was washed with two 100 ml portions of 2-propanol, then dried in a vacuum oven to provide 3.1 grams (88% isolated yield) of the monomer of Formula V.

Example 40

A tetrafunctional monomer was prepared in which two of the pyrone functionalities as well as two of the acetylene groups were present.

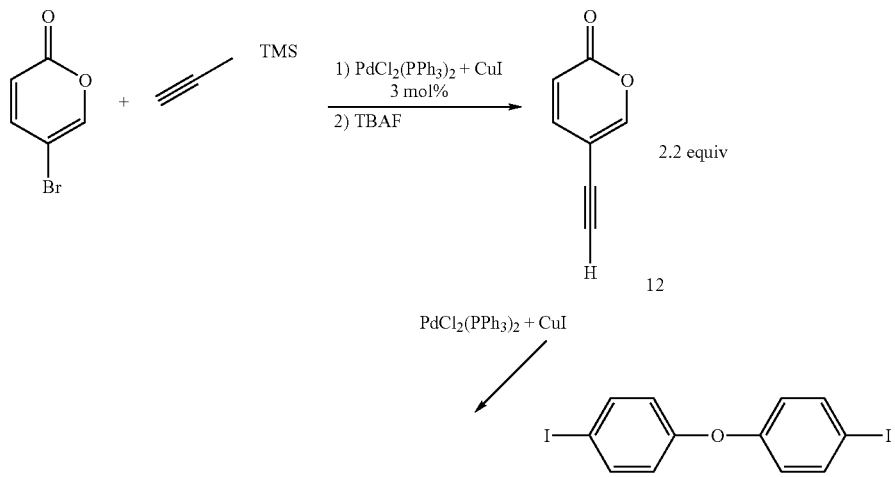

-continued

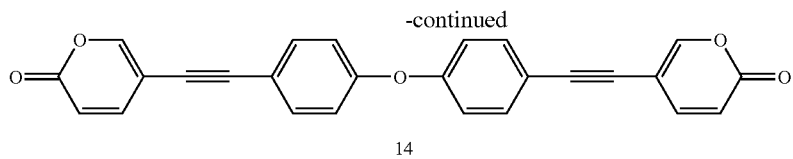

14

The synthetic sequence featured two consecutive Sonogashira couplings. An excess of trimethylsilylacetylene was reacted with 5-bromo-2-pyrone, then the product was desilylated to ethynyl-2-pyrone (12) in 81% overall yield. The 5-ethynyl-2-pyrone was reacted with 4,4'-diiododiphenyl ether (13) to give the monomer (14) in 11% yield. It is interesting to note that the mono coupling (inferred from LC and GC-MS to give 15 shown below) happens very early in the reaction with bis coupling to 14 happening slow enough that the bis coupled acetylene (16) becomes a major product.

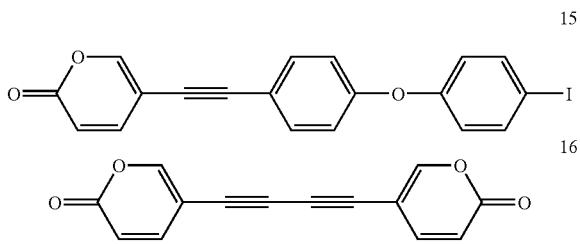

Specifically, 5-[(Trimethylsilyl)ethynyl]-2H-pyran-2-one

To a mixture of 5-bromo-2H-pyran-2-one (7.9 g, 45 mmol) and trimethylsilylacetylene (8.8 g, 100 mmol) in 1,4 dioxane (600 mL) was added, while sparging with N2, dichlorobis(triphenylphosphine)palladium(II) (1.6 g, 0.225 mmol), copper(I) iodide (0.466 g, 0.225 mmol), and triethylamine (4.5 g, 45 mmol). The mixture was stirred for 16 h at 20° C. and then filtered. The solvent was removed under reduced pressure. The residue was dissolved in ether, washed with 1N HCl, sat. NaHCO3 and brine, then dried (MgSO4). The organic phase was passed through a plug of silica gel and then concentrated under reduced pressure. Purification of the residue by silica gel chromatography (5-50% v/v EtOAc/Hexanes) gave the title compound (7.2 g, 84%) as a tan solid; mp 82-83° C. 1H NMR (CDCl3, 300 MHz): δ 7.66 (dd, 1H), 7.27 (dd, 1H), 6.25 (dd, 1H), 0.185 (s, 9H). 13C NMR (CDCl3, 300 MHz) 159.5; 155.3; 144.9; 115.8; 104.4; 98.3; 96.4; –0.44.

5-Ethynyl-2H-pyran-2-one (12)

To a solution of 5-[(trimethylsilyl)ethynyl]-2H-pyran-2-one (0.5 g, 2.6 mmol) and acetic acid (0.6 g, 10 mmol) in THF (50 mL) at 0° C. was added dropwise over 10 min tetrabutylammonium fluoride. The mixture was stirred for 1 h at 0° C. then was partitioned between sat. NaHCO3 and ether. The organic phase was washed with brine then dried (MgSO4). The solvent was passed through a plug of silica gel and then evaporated to give the title compound (0.30 g, 96%) as an off white solid; mp 99-100° C. 1H NMR (CDCl3, 300 MHz): δ 7.73 (dd, 1H), 7.33 (dd, 1H), 6.32 (dd, 1H), 3.11 (s, 1H). 13C NMR (CDCl3, 300 MHz) 159.4; 155.7; 144.6; 116.1; 103.3; 80.7; 75.7. Anal. Calc'd for C7H4O2: C, 70.00; H 3.36. Found: C, 70.09; H, 3.47.

5,5'-[Oxybis(4,1-phenylene-2,1-ethynediyl)]bis-2H-pyran-2-one (14)

To a mixture of 5-ethynyl-2H-pyran-2-one (0.3 g, 2.5 mmol) and 4,4'-diiododiphenyl ether (0.46 g, 1.1 mmol) in 1,4 dioxane was added, with N2 sparging, dichlorobis(triphenylphosphine)palladium(II) (89 mg, 0.125 mmol, ), copper(I) iodide (0.46 mg, 0.25 mmol) and triethylamine (0.25 g, 2.45 mmol). The mixture was sparged for an additional hour and then heated briefly to 50° C. then allowed to stir at 20° C. for 16 h. The mixture was filtered and the solvent was evaporated. The residue was taken up in ethyl acetate washed with 1N HCl, sat. bicarb, brine and then dried (MgSO4). The solvent was evaporated and the residue was subjected to reverse phase prep chromatography using 70: 30CH3CN/H2O as eluant. The product fractions were condensed to give the title compound (108 mg, 11%) as white crystals; mp 204-205° C. dec. 1H NMR (CDCl3, 300 MHz): δ 7.74 (dd, 2H), 7.47 (d, 4H), 7.36 (dd, 2H), 7.0 (d, 4H), 6.34 (dd, 2H). 13C NMR (CDCl3, 300 MHz) 159.6; 156.9; 154.4; 144.8; 133.2; 118.9; 117.3; 116.1; 104.5; 91.7; 80.8. Anal. Calc'd for C26H14O5: C, 76.84; H 3.47. Found: C, 76.56; H, 4.85.

Also isolated from this reaction:

1,1'-(1,3-Butadiyne-1,4-diyl)bis-2H-pyran-2-one (16)

As an off white solid, no melting point observed at 300° C. 1H NMR (D6 DMSO, 300 MHz): δ 8.35 (dd, 2H), 7.61 (dd, 2H), 6.41 (dd, 2H). 13C NMR (D6 DMSO, 300 MHz) 159.5; 158.9; 144.8; 115.8; 101.9; 75.7; 75.4.

The above monomer 14 was dispersed in gamma-butyrolactone (15% monomer) and heated to 200 degrees centigrade. Samples were withdrawn periodically and analyzed by gel permeation chromatography and visibly inspected for gel formation. After 1 hour the Mn was 696 and Mw was 1917. After 1.5 hours gellation occurred indicating that the resulting polymeric material was not soluble in the solvent.

What is claimed is:

1. A highly crosslinked polymer made by polymerizing a reaction mixture comprising a monomer of the formula

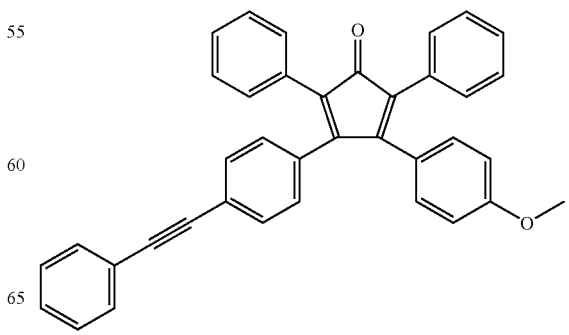

-continued

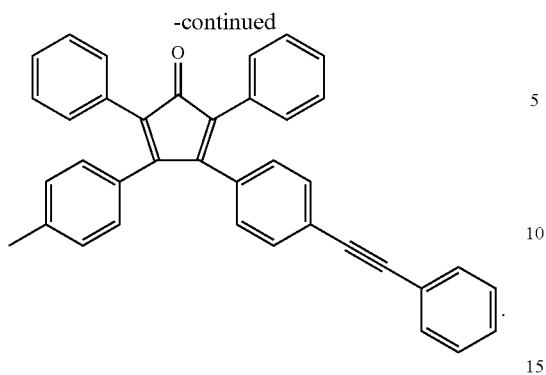

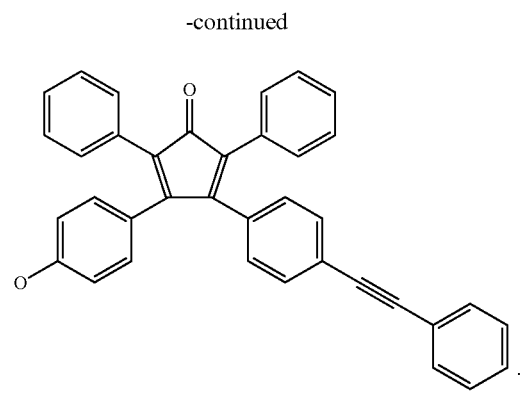

2. A composition comprising an oligomer made by partially polymerizing a monomer of the formula

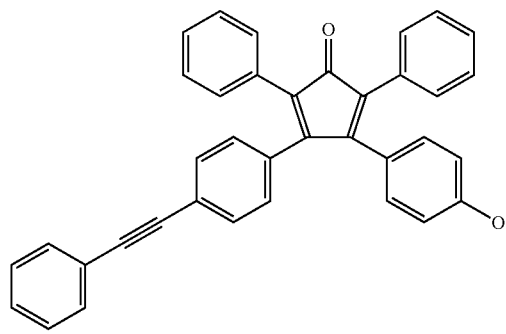

3. The composition of claim 2 further comprising a porogen.

4. The composition of claim 3 wherein the porogen is a polymer which has a molecular architecture selected from, cross-linked nanoparticle, linear, branched, hyperbranched, dendritic, star-like.

5. The composition of claim 3 wherein the porogen is a crosslinked nanoparticle comprising a styrenic polymer.

6. A partially polymerized reaction product of a reaction mixture comprising a monomer of the formula:

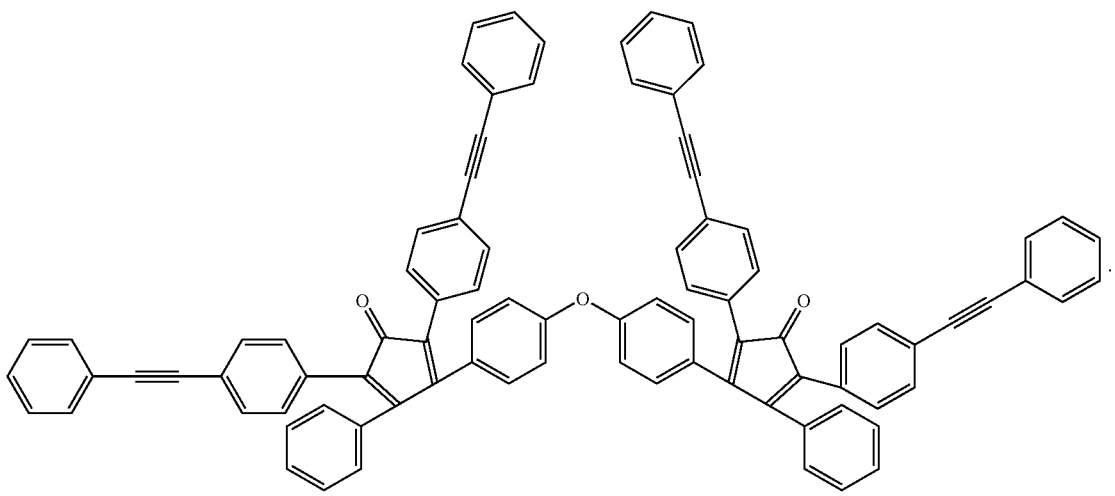

7. A highly crosslinked polymer made by polymerizing a reaction mixture comprising a monomer of the formula
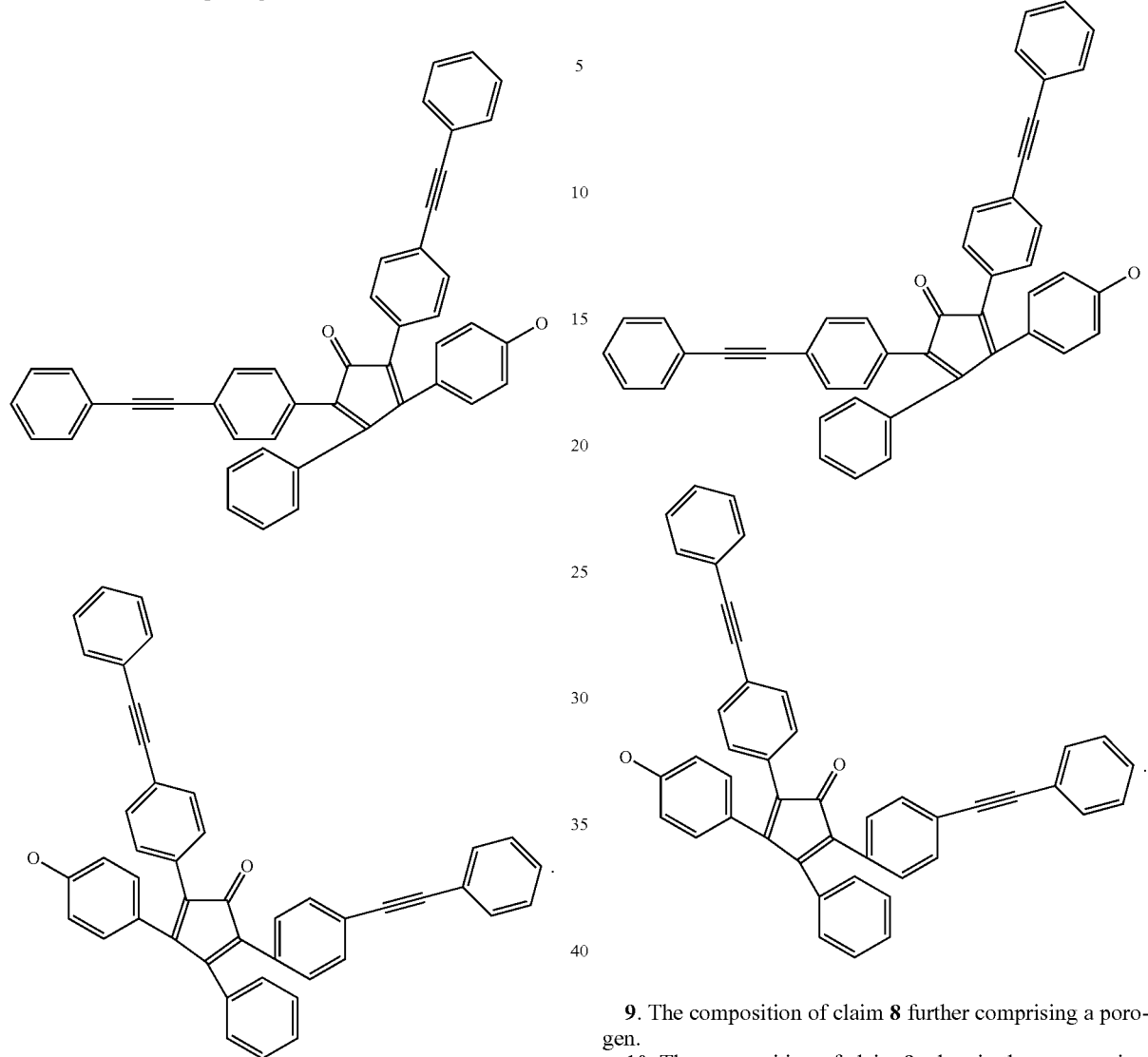
8. A composition comprising an oligomer made by partially polymerizing a monomer of the formula:
9. The composition of claim 8 further comprising a porogen.
10. The composition of claim 9 wherein the porogen is a styrenic polymer.
* * * * *

UNITED STATES PATENT AND TRADEMARK OFFICE
CERTIFICATE OF CORRECTION

| | | |
|---|---|---|
| PATENT NO. | : 7,635,741 B2 | Page 1 of 1 |
| APPLICATION NO. | : 10/365938 | |
| DATED | : December 22, 2009 | |
| INVENTOR(S) | : Q. Jason Niu et al. | |

It is certified that error appears in the above-identified patent and that said Letters Patent is hereby corrected as shown below:

The following should be added to the Front Page of the Patent:

-- Related U.S. Application Data
(63) Continuation-in-part of application No. 10/078,205, filed on February 15, 2002, now abandoned. --

The following should be added to Column 1 under the Title and before line 5:

-- This application is a continuation-in-part of prior application Ser. No. 10/078,205 filed February 15, 2002. --

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,635,741 B2  Page 1 of 1
APPLICATION NO. : 10/365938
DATED : December 22, 2009
INVENTOR(S) : Niu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 233 days.

Signed and Sealed this

Twenty-first Day of December, 2010

David J. Kappos
*Director of the United States Patent and Trademark Office*